(12) United States Patent
Yoon et al.

(10) Patent No.: US 12,329,030 B2
(45) Date of Patent: Jun. 10, 2025

(54) ORGANIC COMPOUND, ORGANIC LIGHT EMITTING DIODE AND ORGANIC LIGHT EMITTING DEVICE HAVING THE COMPOUND

(71) Applicant: LG DISPLAY CO., LTD, Seoul (KR)

(72) Inventors: Dae Wi Yoon, Paju-si (KR); Seon Keun Yoo, Paju-si (KR); Shin Han Kim, Paju-si (KR); Min Gi Hong, Paju-si (KR); Seong Su Jeon, Paju-si (KR); Ji Cheol Shin, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 853 days.

(21) Appl. No.: 17/617,905

(22) PCT Filed: Jun. 15, 2021

(86) PCT No.: PCT/KR2021/007427
§ 371 (c)(1),
(2) Date: Dec. 9, 2021

(87) PCT Pub. No.: WO2022/124502
PCT Pub. Date: Jun. 16, 2022

(65) Prior Publication Data
US 2022/0231236 A1    Jul. 21, 2022

(30) Foreign Application Priority Data
Dec. 8, 2020   (KR) .................. 10-2020-0170430

(51) Int. Cl.
*H10K 85/60*    (2023.01)
*C07D 471/04*   (2006.01)
(Continued)

(52) U.S. Cl.
CPC ....... *H10K 85/6576* (2023.02); *C07D 471/04* (2013.01); *C09K 11/06* (2013.01);
(Continued)

(58) Field of Classification Search
CPC .......... H10K 85/6562; H10K 85/6574; H10K 85/6576; C07D 307/91; C07D 333/76; C07D 471/04
See application file for complete search history.

(56) References Cited

U.S. PATENT DOCUMENTS 9,871,206 B2    1/2018  Mizutani et al.
10,510,964 B2   12/2019 Mizutani et al.
(Continued)

FOREIGN PATENT DOCUMENTS

CN    104603137 A    5/2015
CN    108218858 A    6/2018
(Continued)

OTHER PUBLICATIONS

Machine-generated English-language translation of CN-110642724-A.*
(Continued)

*Primary Examiner* — Vu A Nguyen
(74) *Attorney, Agent, or Firm* — Fenwick & West LLP

(57) ABSTRACT

The present disclosure relates to an organic compound having the following structure of Formula 1, an organic light emitting diode (OLED) where an electron transport layer and/or a charge generation layer includes the organic compound and an organic light emitting device including the organic light emitting diode. While only the specific moiety in the organic compound is deuterated, the organic compound can implement excellent luminous efficiency and luminous lifespan as a compound where all the carbon atoms are deuterated. The OLED can maximize its luminous efficiency and luminous lifespan with minimizing utilization of expensive deuterium.

(Continued)

[Formula 1]

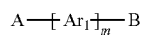

22 Claims, 5 Drawing Sheets

(51) Int. Cl.
  *C09K 11/06* (2006.01)
  *H10K 50/16* (2023.01)
  *H10K 50/19* (2023.01)
(52) U.S. Cl.
  CPC ....... *H10K 85/615* (2023.02); *H10K 85/6572* (2023.02); *H10K 85/6574* (2023.02); *C07B 2200/05* (2013.01); *C09K 2211/1018* (2013.01); *H10K 50/16* (2023.02); *H10K 50/166* (2023.02); *H10K 50/19* (2023.02)

(56) References Cited

U.S. PATENT DOCUMENTS

| | | |
|---|---|---|
| 10,937,984 B2 | 3/2021 | Shin et al. |
| 2014/0077191 A1* | 3/2014 | Mizutani ............ H10K 85/6574 546/88 |
| 2018/0102484 A1 | 4/2018 | Mizutani et al. |
| 2018/0166647 A1 | 6/2018 | Shin et al. |

FOREIGN PATENT DOCUMENTS

| | | | |
|---|---|---|---|
| CN | 110642724 A | * 1/2020 | ........... C07C 211/61 |
| CN | 111410655 A | 7/2020 | |
| KR | 10-2019-0112243 A | 10/2019 | |
| KR | 10-2020-0132290 A | 11/2020 | |

OTHER PUBLICATIONS

China National Intellectual Property Administration, Office Action, Chinese Patent Application No. 202180003839.9, Sep. 29, 2023, 12 pages.

PCT International Search Report, PCT/KR2021/007427, Oct. 1, 2021, 4 Pages.

* cited by examiner

ORGANIC COMPOUND, ORGANIC LIGHT EMITTING DIODE AND ORGANIC LIGHT EMITTING DEVICE HAVING THE COMPOUND

TECHNICAL FIELD

The present disclosure relates to an organic compound, and more specifically, to an organic compound having excellent luminous efficiency and luminous lifespan and an organic light emitting diode and an organic light emitting device including the organic compound.

BACKGROUND ART

An organic light emitting diode (OLED) among a flat display device used widely has come into the spotlight as a display device replacing rapidly a liquid crystal display device (LCD). The OLED can be formed as a thin organic film less than 2000 Å and can implement unidirectional or bidirectional images by electrode configurations. Also, the OLED can be formed even on a flexible transparent substrate such as a plastic substrate so that a flexible or a foldable display device can be realized with ease using the OLED. In addition, the OLED can be driven at a lower voltage and the OLED has excellent high color purity compared to the LCD.

Since fluorescent material uses only singlet exciton energy in the luminous process, the related art fluorescent material shows low luminous efficiency. On the contrary, phosphorescent material can show high luminous efficiency since it uses triplet exciton energy as well as singlet exciton energy in the luminous process. However, metal complex, representative phosphorescent material, has short luminous lifespan for commercial use. Particularly, the blue luminous materials have shown unsatisfactory luminous lifespan and luminous efficiency compared to other luminous materials. Therefore, there remains a need to develop a new compound that can enhance luminous efficiency and luminous lifespan.

DISCLOSURE OF INVENTION

Technical Problem

Accordingly, embodiments of the present disclosure are directed to an organic compound, an organic light emitting diode and an organic light emitting device have substantially obviates one or more of the problems due to the limitations and disadvantages of the related art.

An object of the present disclosure is to provide an organic compound having excellent luminous efficiency and luminous lifespan, an organic light emitting diode and an organic light emitting device including the organic compound.

Another object of the present disclosure is to provide an organic compound having excellent durable properties to external stress such as heat with minimizing the utilization of expensive deuterium, an organic light emitting diode and an organic light emitting device including the organic compound.

Addition features and aspect will be set forth in the description that follows, and in part will be apparent from the description, or can be learned by practice of the inventive concepts provided herein. Other features and aspect of the inventive concept can be realized and attained by the structure practically pointed out in the written description, or derivatives therefrom, and the claims hereof as well as the appended drawings.

Solution to Problem

The achieve these and other aspects of the inventive concepts, as embodied and broadly descried, in one aspect, the present disclosure provides an organic compound having the following structure of Formula 1:

[Formula 1]

wherein $Ar_1$ is $C_6$-$C_{30}$ arylene or $C_3$-$C_{30}$ hetero arylene, each of the $C_6$-$C_{30}$ arylene or the $C_3$-$C_{30}$ hetero arylene is independently unsubstituted or substituted with at least one of a $C_1$-$C_{10}$ alkyl group, a $C_6$-$C_{20}$ aryl group and a $C_3$-$C_{20}$ hetero aryl group; A has the following structure of Formula 2; B has the following structure of Formula 3; and m is 0 or 1;

[Formula 2]

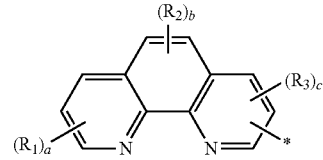

wherein each of $R_1$ to $R_3$ is independently protium, halogen, a cyano group, a $C_1$-$C_{20}$ alkyl group, a $C_1$-$C_{20}$ halo alkyl group, a $C_1$-$C_{20}$ alkoxy group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, the $C_1$-$C_{20}$ alkoxy group is unsubstituted or substituted with halogen, and each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group; each of a, b and c is a number of a substituent, a is an integer of 0 to 3, each of b and c is independently an integer of 0 to 2;

[Formula 3]

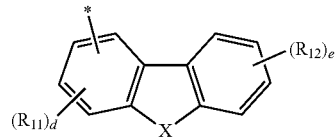

wherein X is O, S or —O═S═O; each of $R_{11}$ and $R_{12}$ is independently protium, deuterium, halogen, a cyano group, a $C_1$-$C_{20}$ alkyl group, a $C_1$-$C_{20}$ halo alkyl group, a $C_1$-$C_{20}$ alkoxy group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group, at least one of $R_{11}$ and $R_{12}$ is deuterium, $R_{11}$ is identical to or different from each other when d is two or more and $R_{12}$ is identical to or different from each other when e is two or more; each of d and e is a number of a substituent, d is an integer of 0 to 3 and e is an integer of 0 to 4, at least one of d and e is not 0.

In another aspect, the present disclosure provides an organic light emitting diode, which comprises a first electrode; a second electrode facing the first electrode; and an emissive layer disposed between the first electrode and the second electrode, wherein the emissive layer includes at least one emitting material layer and at least one electron transport layer disposed between the at least one emitting material layer and the second electrode, and wherein the at least one electron transport layer includes an organic compound having the structure of Formula 1.

In still another aspect, the present disclosure provides an organic light emitting diode which comprises a first electrode; a second electrode; and an emissive layer disposed between the first electrode and the second electrode, wherein the emissive layer includes a first emitting part disposed between the first electrode and the second electrode, a second emitting part disposed between the first emitting part and the second electrode and a charge generation layer disposed between the first emitting part and the second emitting part, wherein the first emitting part includes a first emitting material layer and a first electron transport layer disposed between the first emitting material layer and the charge generation layer, and wherein at least one of the first electron transport layer and the charge generation layer includes an organic compound having the following structure of Formula 1.

In further still another aspect, the present disclosure provides an organic light emitting device which comprises a substrate; and the organic light emitting diode over the substrate.

In the organic light emitting device, the substrate may define a red pixel region, a green pixel region and a blue pixel region and the organic light emitting diode may be located correspondingly to the red pixel region, the green pixel region and the blue pixel region, and the organic light emitting device may further include a color filter layer disposed between the substrate and the organic light emitting diode or over the organic light emitting diode correspondingly to the red pixel region, the green pixel region and the blue pixel region.

In the organic light emitting device, the substrate may define a red pixel region, a green pixel region and a blue pixel region and the organic light emitting diode may be located correspondingly to the red pixel region, the green pixel region and the blue pixel region, and the organic light emitting device may further include a color conversion layer disposed between the substrate and the organic light emitting diode or over the organic light emitting diode correspondingly to the red pixel region and the green pixel region.

Advantageous Effects of Invention

The organic compound of the present disclosure is deuterated in a specific moiety. Since deuterium has good resistance to external stress such as heat, the organic compound where only a specific moiety that can easily undergo thermal decomposition is deuterated shows excellent luminous efficiency and luminous lifespan similar to a compound where all protium atoms within the entire molecule are substituted with deuterium atoms. An organic light emitting diode (OLED) and an organic light emitting device having improved luminous efficiency and luminous lifespan can be manufactured by introducing the organic compound substituted deuterium in only the specific moiety without substituting with deuterium atoms in the entire molecule. It is possible to have an advantage of economically utilizing expensive deuterium, and thereby reducing the manufacturing cost of the light emitting diode with great.

BRIEF DESCRIPTION OF DRAWINGS

The accompanying drawings, which are included to provide a further understanding of the present disclosure, are incorporated in and constitute a part of this application, illustrate embodiments of the disclosure and together with the description serve to explain principles of the disclosure.

MODE FOR INVENTION

Figure 1:
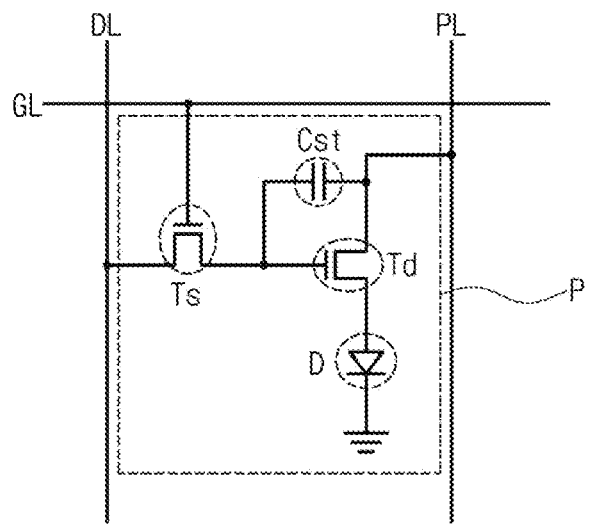
FIG. 1 is a schematic circuit diagram illustrating an organic light emitting display device in accordance with the present disclosure.

Reference will now be made in detail to aspects of the disclosure, examples of which are illustrated in the accompanying drawings.

An emissive layer of an organic light emitting diode (OLED) includes an organic compound having proper energy level and excellent charge mobility property. The present disclosure relates to an organic compound that includes a phenanthroline moiety having excellent electron transport property and electron injection property and at least one nuclear atom within a fused hetero aromatic moiety including O and/or S is deuterated. The organic compound of the present disclosure may have the following structure of Formula 1:

[Formula 1]

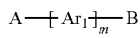

wherein $Ar_1$ is $C_6$-$C_{30}$ arylene or $C_3$-$C_{30}$ hetero arylene, each of the $C_6$-$C_{30}$ arylene or the $C_3$-$C_{30}$ hetero arylene is independently unsubstituted or substituted with at least one of a $C_1$-$C_{10}$ alkyl group, a $C_6$-$C_{20}$ aryl group and a $C_3$-$C_{20}$ hetero aryl group; A has the following structure of Formula 2; B has the following structure of Formula 3; and m is 0 or 1;

[Formula 2]

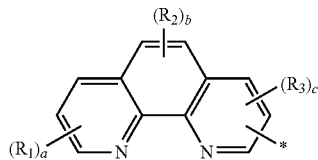

wherein each of $R_1$ to $R_3$ is independently protium, halogen, a cyano group, a $C_1$-$C_{20}$ alkyl group, a $C_1$-$C_{20}$ halo alkyl group, a $C_1$-$C_{20}$ alkoxy group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, the $C_1$-$C_{20}$ alkoxy group is unsubstituted or substituted with halogen, and each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group; each of a, b and c is a number of a substituent, a is an integer of 0 to 3, each of b and c is independently an integer of 0 to 2;

[Formula 3]

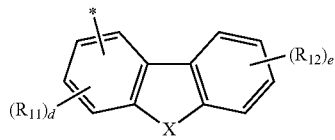

wherein X is O, S or —O=S=O; each of $R_{11}$ and $R_{12}$ is independently protium, deuterium, halogen, a cyano group, a $C_1$-$C_{20}$ alkyl group, a $C_1$-$C_{20}$ halo alkyl group, a $C_1$-$C_{20}$ alkoxy group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group, at least one of $R_{11}$ and $R_{12}$ is deuterium, $R_{11}$ is identical to or different from each other when d is two or more and $R_{11}$ is identical to or different from each other when e is two or more; each of d and e is a number of a substituent, d is an integer of 0 to 3 and e is an integer of 0 to 4, at least one of d and e is not 0.

As used herein, substituent in the term "substituted" comprises, but is not limited to, deuterium, unsubstituted or deuterium or halogen-substituted $C_1$-$C_{20}$ alkyl, unsubstituted or deuterium or halogen-substituted $C_1$-$C_{20}$ alkoxy, halogen, cyano, —$CF_3$, a hydroxyl group, a carboxylic group, a carbonyl group, an amino group, a $C_1$-$C_{10}$ alkyl amino group, a $C_6$-$C_{30}$ aryl amino group, a $C_3$-$C_{30}$ hetero aryl amino group, a $C_6$-$C_{30}$ aryl group, a $C_3$-$C_{30}$ hetero aryl group, a nitro group, a hydrazyl group, a sulfonate group, a $C_1$-$C_{20}$ alkyl silyl group, a $C_6$-$C_{30}$ aryl silyl group and a $C_3$-$C_{30}$ hetero aryl silyl group.

As used herein, the term 'hetero" in such as "hetero aromatic group", "hetero alicyclic group", "hetero aryl group", "hetero aryl alkyl group", "hetero aryloxy group", "hetero aryl amino group" and the like means that at least one carbon atom, for example 1-5 carbons atoms, constituting an alicyclic group or ring or an aromatic group or ring is substituted with at least one hetero atom selected from the group consisting of N, O, S, P and combination thereof.

In one exemplary aspect, when each of $R_1$ to $R_3$ in Formula 2 and each of $R_{11}$ and $R_{12}$ in Formula 3 is independently a $C_6$-$C_{30}$ aromatic group, each of $R_1$ to $R_3$, $R_{11}$ and $R_{12}$ may comprise independently, but is not limited to, a $C_6$-$C_{30}$ aryl group, a $C_7$-$C_{30}$ aryl alkyl group, a $C_6$-$C_{30}$ aryloxy group and a $C_6$-$C_{30}$ aryl amino group. As an example, when each of Ru to $R_3$, $R_{11}$ and $R_{12}$ is independently a $C_6$-$C_{30}$ aryl group, each of $R_1$ to $R_3$, $R_{11}$ and $R_{12}$ may independently comprise, but is not limited to, an unfused or fused aryl group such as phenyl, biphenyl, terphenyl, naphthyl, anthracenyl, pentalenyl, indenyl, indeno-indenyl, heptalenyl, biphenylenyl, indacenyl, phenalenyl, phenanthrenyl, benzophenanthrenyl, dibenzophenanthrenyl, azulenyl, pyrenyl, fluoranthenyl, triphenylenyl, chrysenyl, tetraphenylenyl, tetracenyl, pleiadenyl, picenyl, pentaphenylenyl, pentacenyl, fluorenyl, indenofluorenyl and spiro-fluorenyl.

Alternatively, when each of $R_1$ to $R_3$ in Formula 2 and each of $R_{11}$ and $R_{12}$ in Formula 3 is independently a $C_3$-$C_{30}$ hetero aromatic group, each of $R_1$ to $R_3$, $R_{11}$ and $R_{12}$ may comprise independently, but is not limited to, a $C_3$-$C_{30}$ hetero aryl group, a $C_4$-$C_{30}$ hetero aryl alkyl group, a $C_3$-$C_{30}$ hetero aryl oxy group and a $C_3$-$C_{30}$ hetero aryl amino group. As an example, when each of $R_1$ to $R_3$, $R_{11}$ and $R_{12}$ $R_1$ to $R_6$ is independently a $C_3$-$C_{30}$ hetero aryl group, each of $R_1$ to $R_3$, $R_{11}$ and $R_{12}$ $R_1$ to $R_6$ may independently comprise, but is not limited to, an unfused or fused hetero aryl group such as pyrrolyl, pyridinyl, pyrimidinyl, pyrazinyl, pyridazinyl, triazinyl, tetrazinyl, imidazolyl, pyrazolyl, indolyl, iso-indolyl, indazolyl, indolizinyl, pyrrolizinyl, carbazolyl, benzocarbazolyl, dibenzocarbazolyl, indolo-carbazolyl, indeno-carbazolyl, benzofuro-carbazolyl, benzothieno-carbazolyl, carbolinyl, quinolinyl, iso-quinolinyl, phthlazinyl, quinoxalinyl, cinnolinyl, quinazolinyl, quinolizinyl, purinyl, benzoquinolinyl, benzoiso-quinolinyl, benzoquinazolinyl, benzoquinoxalinyl, acridinyl, phenazinyl, phenoxazinyl, phenothiazinyl, phenanthrolinyl, perimidinyl, phenanthridinyl, pteridinyl, naphthyridinyl, furanyl, pyranyl, oxazinyl, oxazolyl, oxadiazolyl, triazolyl, dioxinyl, benzofuranyl, dibenzofuranyl, thiopyranyl, xanthenyl, chromenyl, iso-chromenyl, thioazinyl, thiophenyl, benzothiophenyl, dibenzothiophenyl, difuro-pyrazinyl, benzofuro-dibenzofuranyl, benzothieno-benzothiophenyl, benzothieno-dibenzothiophenyl, benzothieno-benzofuranyl, benzothieno-dibenzofuranyl, xanthene-linked spiro acridinyl, dihydroacridinyl substituted with at least one $C_1$-$C_{10}$ alkyl and N-substituted spiro fluorenyl.

As an example, when each of $R_1$ to $R_3$, $R_{11}$ and $R_{12}$ is independently the aromatic group or the hetero aromatic group, each of $R_1$ to $R_3$, $R_{11}$ and $R_{12}$ may comprise independently, but is not limited to, phenyl, biphenyl, pyrrolyl, triazinyl, imidazolyl, pyrazolyl, pyridinyl, pyrazinyl, pyrimidinyl, pyridazinyl, furanyl, benzofuranyl, dibenzofuranyl, thiophenyl, benzothiophenyl, dibenzothiophenyl and carbazolyl.

When $Ar_1$ is $C_6$-$C_{30}$ arylene, $Ar_1$ may comprise, but is not limited to, phenylene, biphenylene, terphenylene, tetraphenylene, indenylene, napthylene, azulenylene, indacenylene, acenaphthylene, fluorenylene, spiro-fluorenylene, phenalenylene, phenanthrenylene, anthracenylene, fluoranthenylene, triphenylenylene, naphthacenylene, picenylene, perylenylene, pentaphenylene and hexacenylene, each of which may be unsubstituted or substituted with at least one of a $C_1$-$C_{10}$ alkyl group, a $C_6$-$C_{20}$ aryl group and a $C_3$-$C_{20}$ hetero aryl group Alternatively, when $Ar_1$ is $C_3$-$C_{30}$ hetero arylene, $Ar_1$ may comprise, but is not limited to, pyrrolylene, imidazolylene, pyrazolylene, pyridinylene, pyrazinylene, pyrimidinylene, pyridazinylene, isoindolylene, indolylene, indazolylene, purinylene, quinolinylene, isoquinolinylene, benzoquinolinylene, phthalazinylene, naphthyridinylene, quinoxalinylene, quinazolinylene, benzoisoquinolinylene, benzoquinazolinylene, benzoquinoxalinylene, cinnolinylene, phenanthridinylene, acridinylene, phenanthrolinylene, phenazinylene, benzoxazolylene, benzimidazolylene, furanylene, benzofuranylene, thiophenylene, benzothiophenylene, thiazolylene, isothiazolylene, benzothiazolylene, isoxazolylene, oxazolylene, triazolylene, tetrazolylene, oxadiazolylene, triazinylene, dibenzofuranylene, benzofurodibenzofuranylene, benzothienobenzofuranylene, benzothienodibenzofurnalylene, dibenzothiophenylene, benzothienobenzothiophenylene, benzothienodibenzothiophenylene, carbazolylene, benzocarbazolylene, dibenzocarbazolylene, indolocarbazolylene, indencocarbazolylene, benzofurocarbazoloyene, benzothienocarbazolylene, imidazopyrimidinylene and imidazopyridinylene, each of which may be unsubstituted or substituted with at least one of a $C_1$-$C_{10}$ alkyl group, a $C_6$-$C_{20}$ aryl group and a $C_3$-$C_{20}$ hetero aryl group In one exemplary aspect, when the number of the aromatic and/or the hetero aromatic ring constituting $Ar_1$ is becomes larger, the conjugated structure in the whole organic molecules becomes too long, and thus, the organic compound may have too much narrow energy level bandgap. Therefore, $Ar_1$ may have one or two aromatic and/or hetero aromatic ring, for example, one aromatic and/or hetero aromatic ring. With regard to charge injection and charge mobility property, $Ar_1$ may be a 5-membered ring, 6-membered ring or a 7-membered ring, for example, a 6-membered ring. For example, $Ar_1$ may comprise, but is not limited to, phenylene, biphenylene, pyrrolylene, imidazolylene, pyrazolylene, pyridinylene, pyrazinylene, pyrimidinylene, pyridazinylene, furanylene and thiophenylene.

Since the organic compound defined by Formulae 1 to 3 includes a phenanthroline moiety, that is, Formula 2, including nitrogen atoms with enough electrons, the organic compound has excellent electron transport property. In addition, the nitrogen atoms of the phenanthroline moiety can be combined with an alkali metal and/or an alkaline earth metal to form a gap state.

In addition, the organic compound includes a fused hetero aromatic moiety, that is, Formula 3, linked to the phenanthroline moiety directly or through a liner moiety, that is, Ar moiety. Since the organic compound includes the fused hetero aromatic moiety with rigid chemical conformation, the organic compound has improved thermal stability.

At least one of the nuclear carbon atoms constituting the fused hetero aromatic moiety is deuterated. Hydrogen atom of the fused hetero aromatic moiety is positioned adjacently to oxygen or sulfur atom with relatively high electron affinity. Accordingly, the hydrogen atom linked to the nuclear atoms constituting the fused hetero aromatic moiety has high acidity.

Generally, when an organic compound is deuterated, unsubstituted compound with the entire carbon skeleton of the molecule is reacted with deuterium raw material such as $d^6$-benzene or $D_2O$ using acid or base catalysts. However, in this case, a large amount of expensive deuterium raw materials must be used, and results in environmental pollution problem in the deuteration of the whole molecule.

On the contrary, it is possible to delay the dissociation of deuterium from the molecule and improve the electrochemical stability of the molecule by only substituting for at least one protium, which has relatively high acidity, linked to the nuclear carbon atoms constituting the fused hetero aromatic moiety, rather than substituting all the protium within the entire molecule. Accordingly, the organic compound where at least one protium linked to the nuclear carbon atoms constituting the fused hetero aromatic moiety can secure as high luminous efficiency and luminous lifespan as an organic compound where all the nuclear carbon atoms of the aromatic and hetero aromatic rings constituting the skeleton of entire molecule.

In one exemplary aspect, $Ar_1$ is a divalent aromatic bridging group or a divalent hetero aromatic bridging group, $Ar_1$ may be selected from, but is not limited to, the following moieties:

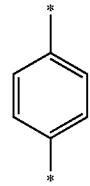

A-1

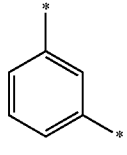

A-2

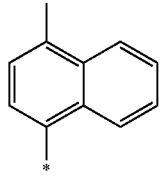

A-3

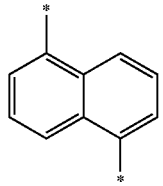

A-4

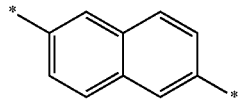

A-5

A-6 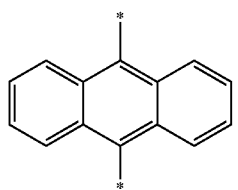
A-7 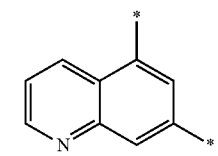
A-8 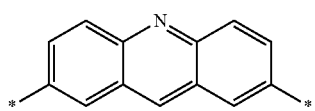
A-9 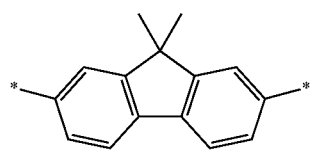
A-10 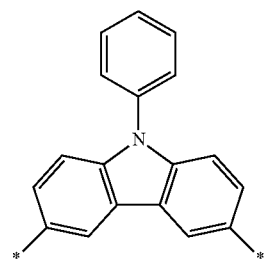
A-11 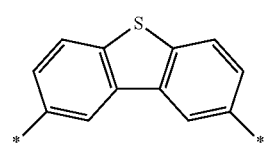
A-12 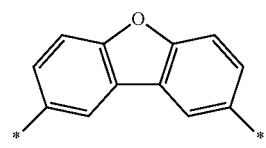
A-13 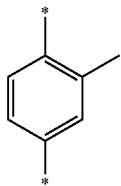
A-14 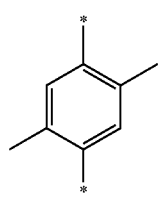
A-15 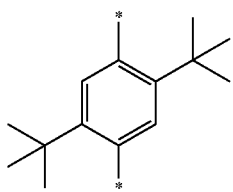
A-16 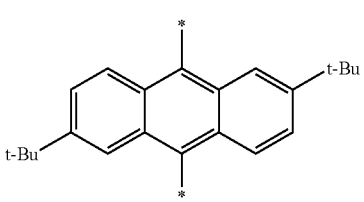
A-17 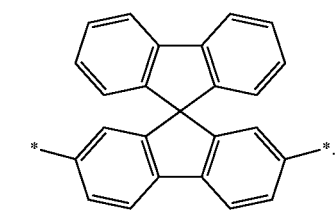
In another exemplary aspect, A in Formula 1 of a phenanthroline moiety having electron transport property, may be selected from, but is not limited to, the following moieties
B-1 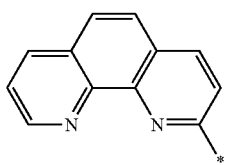
B-2 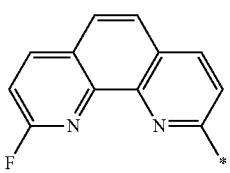
B-3 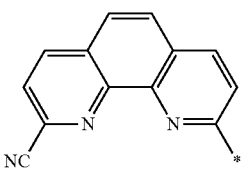
B-4 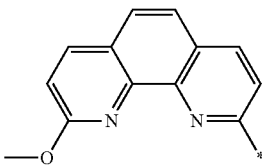

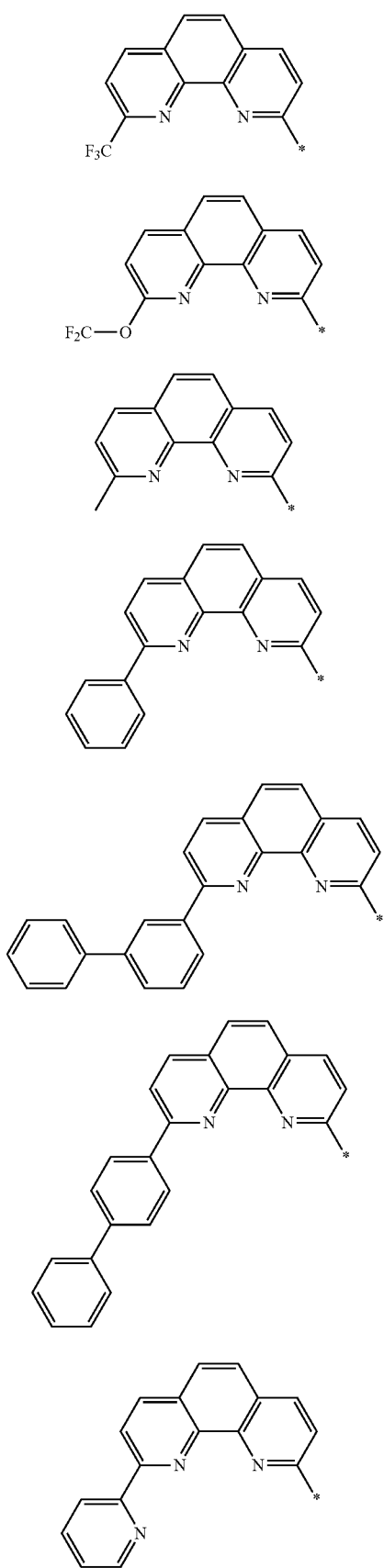
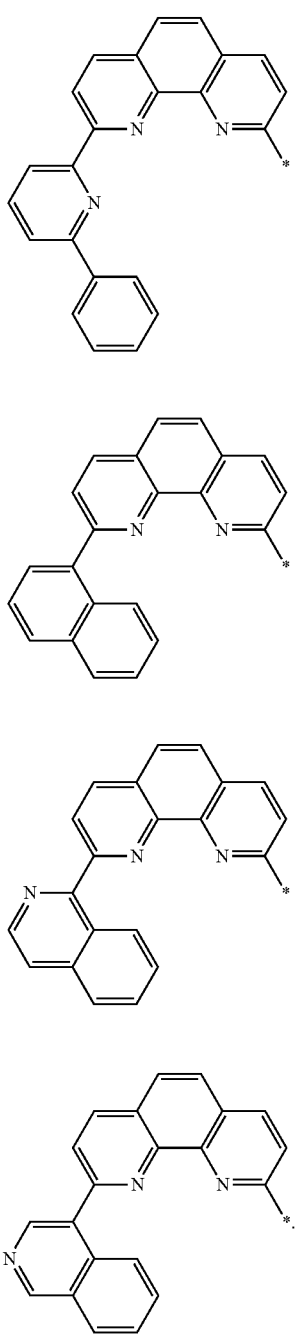
In still another exemplary aspect, B in Formula 1 of the fused hetero aromatic moiety where at least one protium linked to the nuclear carbon atoms may be selected from, but is not limited to, the following moieties:
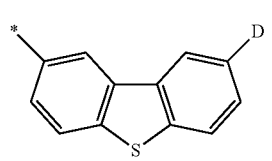

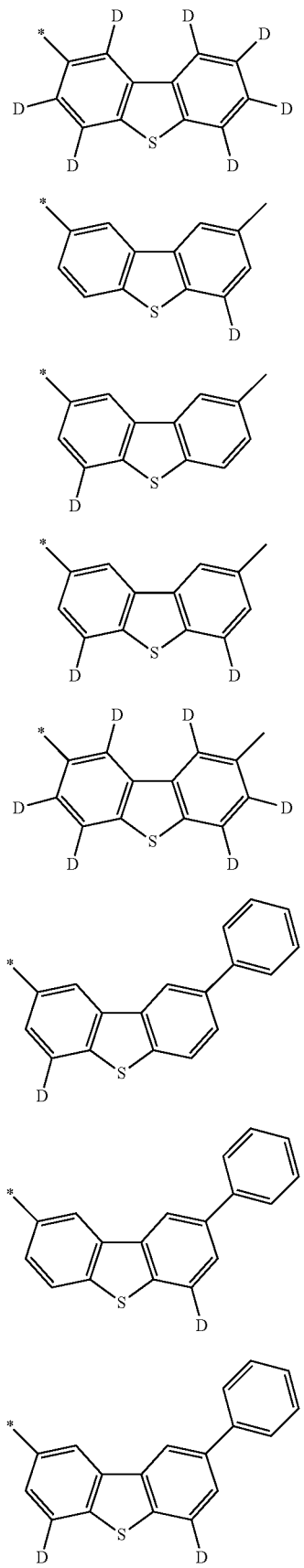

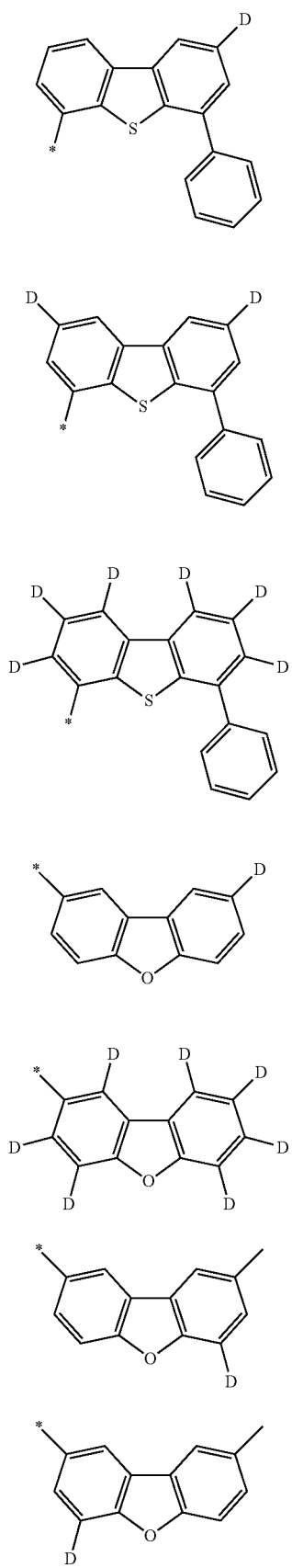

C-32
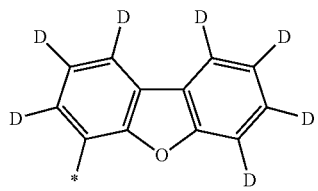
C-33
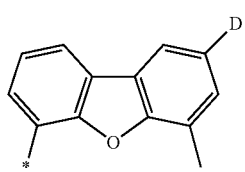
C-34
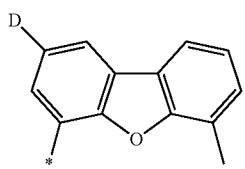
C-35
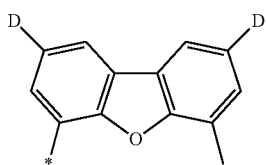
C-36
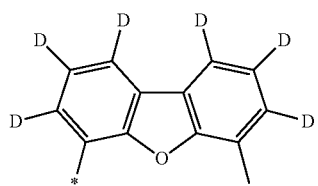
C-37
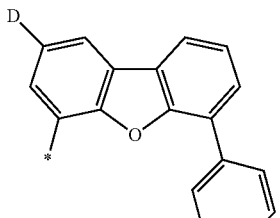
C-38
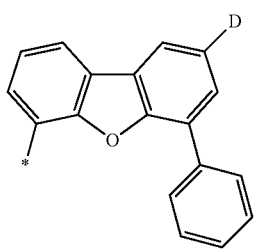
C-39
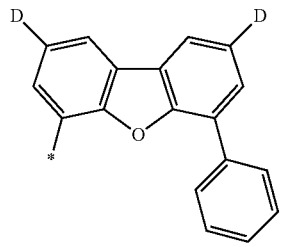
C-40
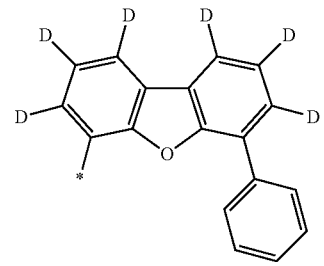
C-41
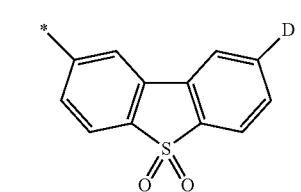
C-42
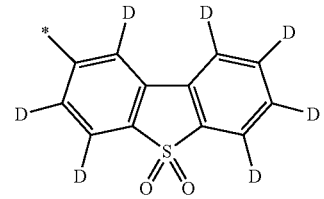
C-43
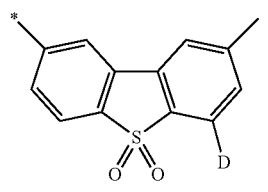
C-44
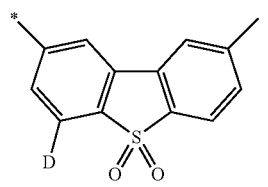
C-45
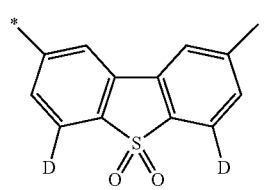

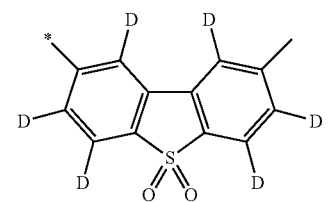
C-46
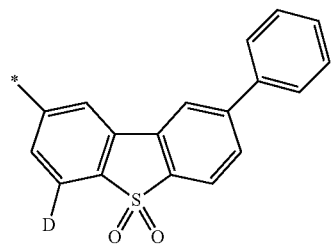
C-47
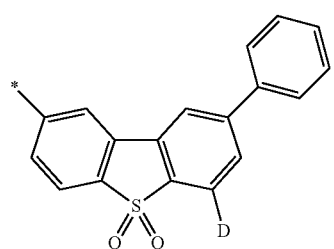
C-48
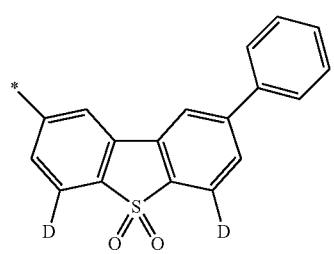
C-49
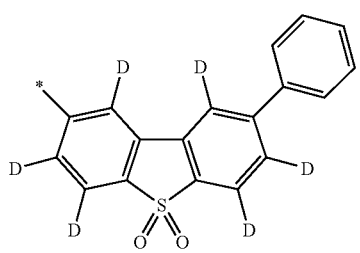
C-50
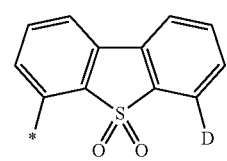
C-51
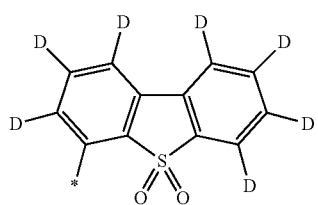
C-52
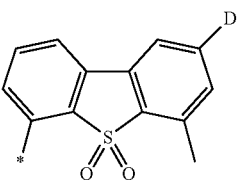
C-53
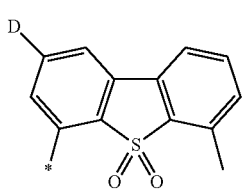
C-54
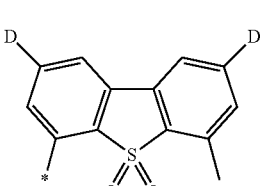
C-55
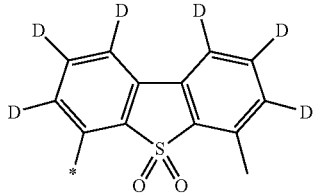
C-56
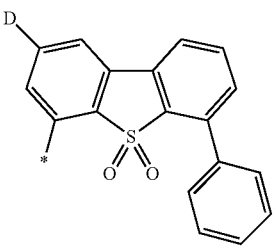
C-57
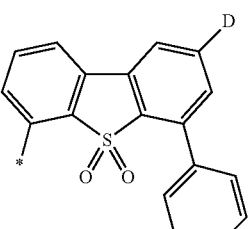
C-58
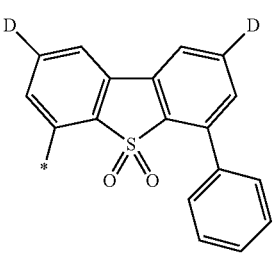
C-59

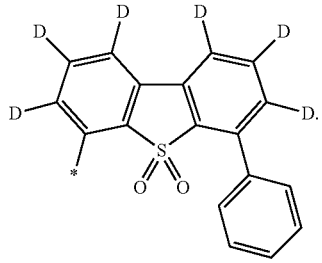
C-60
As an example, the organic compound having the structure of Formula 1 may be selected from, but is not limited to, the following compounds having the structure of Formula 4:
[Formula 4]
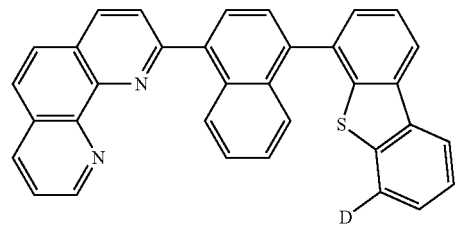
D1
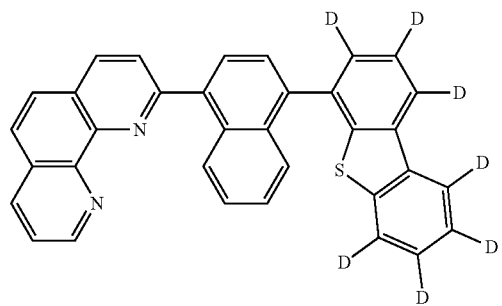
D2
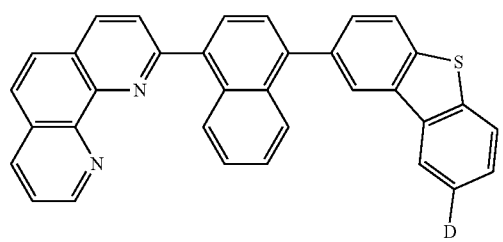
D3
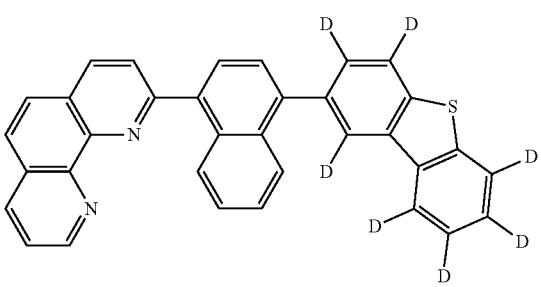
D4
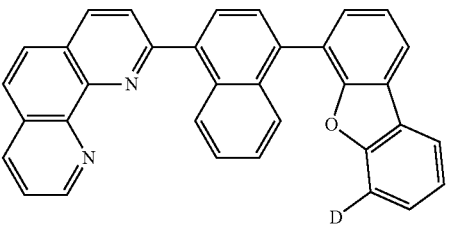
D5
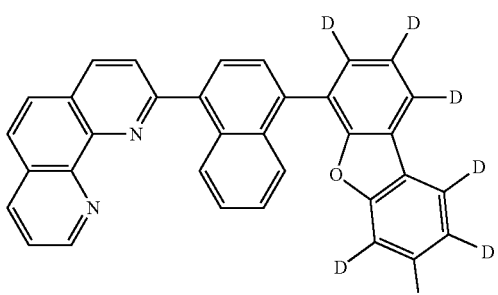
D6
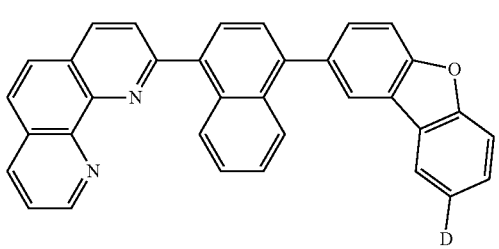
D7
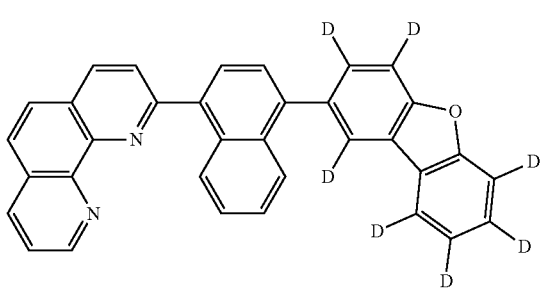
D8
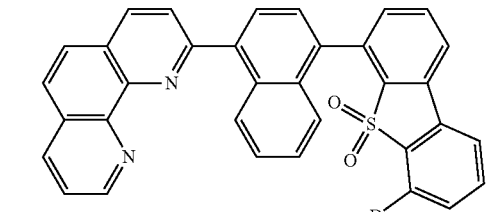
D9
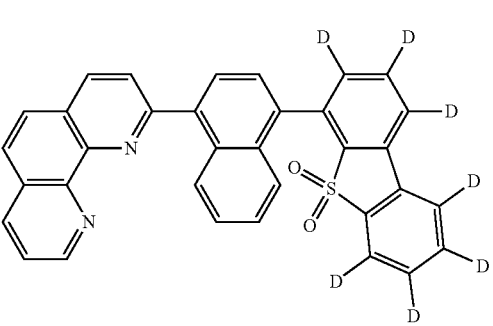
D10

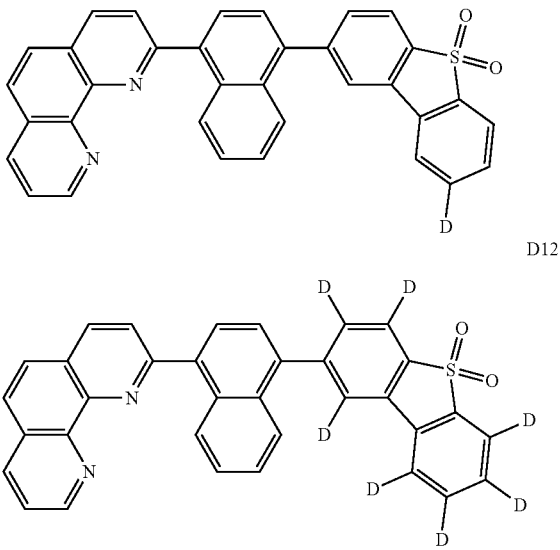

[Organic Light Emitting Diode and Organic Light Emitting Device]

Since the organic compound having the structure of Formulae 1 to 4 has excellent electron transport property and electron injection property, it can be applied into an electron transport layer and/or a charge generation layer of an organic light emitting diode (OLED). The OLED may be applied to an organic light emitting device such as an organic light emitting display device and an organic light emitting illumination device. An organic light emitting display device including the OLED will be explained.

FIG. 1 is a schematic circuit diagram illustrating an organic light emitting display device in accordance with present disclosure. As illustrated in FIG. 1, a gate line GL, a data line DL and power line PL, each of which cross each other to define a pixel region P, in the organic light display device. A switching thin film transistor Ts, a driving thin film transistor Td, a storage capacitor Cst and an organic light emitting diode D are formed within the pixel region P. The pixel region P may include a red (R) pixel region, a green (G) pixel region and a blue (B) pixel region.

The switching thin film transistor Ts is connected to the gate line GL and the data line DL, and the driving thin film transistor Td and the storage capacitor Cst are connected between the switching thin film transistor Ts and the power line PL. The organic light emitting diode D is connected to the driving thin film transistor Td. When the switching thin film transistor Ts is turned on by a gate signal applied into the gate line GL, a data signal applied into the data line DL is applied into a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the organic light emitting diode D through the driving thin film transistor Td. And then, the organic light emitting diode D emits light having a luminance proportional to the current flowing through the driving thin film transistor Td. In this case, the storage capacitor Cst is charged with a voltage proportional to the data signal so that the voltage of the gate electrode in the driving thin film transistor Td is kept constant during one frame. Therefore, the organic light emitting display device can display a desired image.

Figure 2:
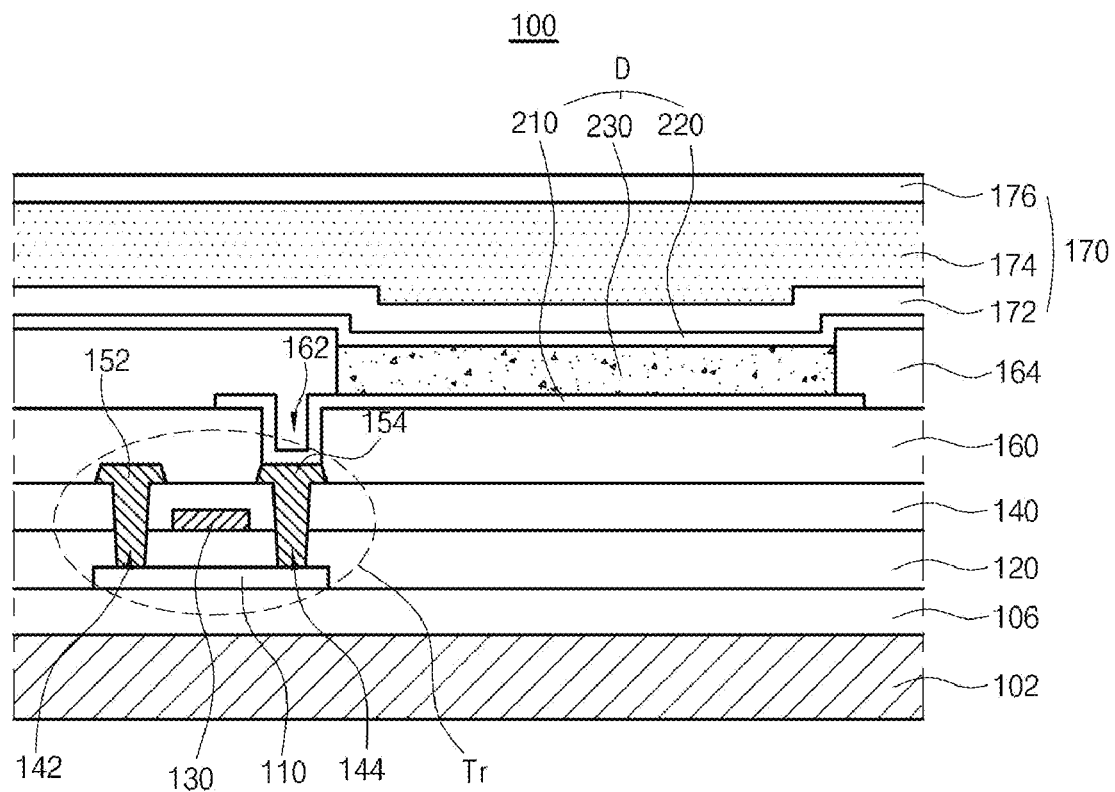
FIG. 2 is a schematic cross-sectional view illustrating an organic light emitting display device as an example of an organic light emitting device in accordance with an exemplary aspect of the present disclosure.

FIG. 2 is a schematic cross-sectional view illustrating an organic light emitting display device in accordance with an exemplary aspect of the present disclosure. As illustrated in FIG. 2, the organic light emitting display device 100 comprises a substrate 102, a thin-film transistor Tr over the substrate 102, and an organic light emitting diode D connected to the thin film transistor Tr. As an example, the substrate 102 defines a red (R) pixel region, a green (G) pixel region and a blue (B) pixel region and the organic light emitting diode D is located in each pixel region. In other words, the organic light emitting diode D, each of which emits red, green or blue light, is located correspondingly in the red (R) pixel region, the green (G) pixel region and the blue (B) pixel region. As an example, the OLED D may be located in the blue (B) pixel region.

The substrate 102 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The substrate 102, over which the thin film transistor Tr and the organic light emitting diode D are arranged, forms an array substrate.

A buffer layer 106 may be disposed over the substrate 102, and the thin film transistor Tr is disposed over the buffer layer 106. The buffer layer 106 may be omitted.

A semiconductor layer 110 is disposed over the buffer layer 106. In one exemplary aspect, the semiconductor layer 110 may include, but is not limited to, oxide semiconductor materials. In this case, a light-shield pattern may be disposed under the semiconductor layer 110, and the light-shield pattern can prevent light from being incident toward the semiconductor layer 110, and thereby, preventing the semiconductor layer 110 from being deteriorated by the light. Alternatively, the semiconductor layer 110 may include polycrystalline silicon. In this case, opposite edges of the semiconductor layer 110 may be doped with impurities.

A gate insulating layer 120 including an insulating material is disposed on the semiconductor layer 110. The gate insulating layer 120 may include, but is not limited to, an inorganic insulating material such as silicon oxide ($SiO_x$) or silicon nitride ($SiN_x$).

A gate electrode 130 made of a conductive material such as a metal is disposed over the gate insulating layer 120 so as to correspond to a center of the semiconductor layer 110. While the gate insulating layer 120 is disposed over a whole area of the substrate 102 in FIG. 2, the gate insulating layer 120 may be patterned identically as the gate electrode 130.

An interlayer insulating layer 140 including an insulating material is disposed on the gate electrode 130 with covering over an entire surface of the substrate 102. The interlayer insulating layer 140 may include an inorganic insulating material such as silicon oxide ($SiO_x$) or silicon nitride ($SiN_x$), or an organic insulating material such as benzocyclobutene or photo-acryl.

The interlayer insulating layer 140 has first and second semiconductor layer contact holes 142 and 144 that expose both sides of the semiconductor layer 110. The first and second semiconductor layer contact holes 142 and 144 are disposed over opposite sides of the gate electrode 130 with spacing apart from the gate electrode 130. The first and second semiconductor layer contact holes 142 and 144 are formed within the gate insulating layer 120 in FIG. 2.

Alternatively, the first and second semiconductor layer contact holes 142 and 144 are formed only within the interlayer insulating layer 140 when the gate insulating layer 120 is patterned identically as the gate electrode 130.

A source electrode 152 and a drain electrode 154, which are made of conductive material such as a metal, are disposed on the interlayer insulating layer 140. The source electrode 152 and the drain electrode 154 are spaced apart from each other with respect to the gate electrode 130, and contact both sides of the semiconductor layer 110 through the first and second semiconductor layer contact holes 142 and 144, respectively.

The semiconductor layer 110, the gate electrode 130, the source electrode 152 and the drain electrode 154 constitute the thin film transistor Tr, which acts as a driving element. The thin film transistor Tr in FIG. 2 has a coplanar structure in which the gate electrode 130, and the source electrode 152 and the drain electrode 154 are disposed over the semiconductor layer 110. Alternatively, the thin film transistor Tr may have an inverted staggered structure in which a gate electrode is disposed under a semiconductor layer and a source and drain electrodes are disposed over the semiconductor layer. In this case, the semiconductor layer may include amorphous silicon.

Although not shown in FIG. 2, a gate line and a data line, which cross each other to define a pixel region, and a switching element, which is connected to the gate line and the data line, is may be further formed in the pixel region. The switching element is connected to the thin film transistor Tr which is a driving element. In addition, a power line is spaced apart in parallel from the gate line or the data line, and the thin film transistor Tr may further include a storage capacitor configured to constantly keep a voltage of the gate electrode for one frame.

A passivation layer 160 is disposed on the source and drain electrodes 152 and 154 with covering the thin film transistor Tr over the whole substrate 102. The passivation layer 160 has a flat top surface and a drain contact hole 162 that exposes the drain electrode 154 of the thin film transistor Tr. While the drain contact hole 162 is disposed on the second semiconductor layer contact hole 144, it may be spaced apart from the second semiconductor layer contact hole 144.

The organic light emitting diode (OLED) D includes a first electrode 210 that is disposed on the passivation layer 160 and connected to the drain electrode 154 of the thin film transistor Tr. The organic light emitting diode D further includes an emissive layer 230 and a second electrode 220 each of which is disposed sequentially on the first electrode 210.

The first electrode 210 is disposed in each pixel region. The first electrode 210 may be an anode and include conductive material having relatively high work function value. For example, the first electrode 210 may include, but is not limited to, a transparent conductive oxide (TCO) such as indium tin oxide (ITO), indium zinc oxide (IZO), indium tin zinc oxide (ITZO), SnO, ZnO, indium cerium oxide (ICO), aluminum doped zinc oxide (AZO), and the like.

In one exemplary aspect, when the organic light emitting display device 100 is a bottom-emission type, the first electrode 201 may have a single-layered structure of the TCO. Alternatively, when the organic light emitting display device 100 is a top-emission type, a reflective electrode or a reflective layer may be disposed under the first electrode 210. For example, the reflective electrode or the reflective layer may include, but is not limited to, silver (Ag) or aluminum-palladium-copper (APC) alloy. In the OLED D of the top-emission type, the first electrode 210 may have a triple-layered structure of ITO/Ag/ITO or ITO/APC/ITO.

In addition, a bank layer 164 is disposed on the passivation layer 160 in order to cover edges of the first electrode 210. The bank layer 164 exposes a center of the first electrode 210 corresponding to each pixel region. The bank layer 164 may be omitted.

An emissive layer 230 is disposed on the first electrode 210. In one exemplary aspect, the emissive layer 230 may have a multiple-layered structure of a hole injection layer (HIL), a hole transport layer (HTL), an electron blocking layer (EBL), an emitting material layer (EML), a hole blocking layer (HBL), an electron transport layer (ETL), an electron injection layer (EIL) and/or a charge generation layer (CGL) (see, FIGS. 3 and 4). In one aspect, the emissive layer 230 may have single emitting part. Alternatively, the emissive layer 230 may have multiple emitting parts to form a tandem structure.

In one exemplary aspect, the emissive layer 230 may comprise at least one EML including an anthracene-based host and a boron-based dopant when the OLED D emits blue light. At least one of the ETL and the CGL may include the organic compound having the structure of Formulae 1 to 4.

The second electrode 220 is disposed over the substrate 102 above which the emissive layer 230 is disposed. The second electrode 220 may be disposed over a whole display area, and may include a conductive material with a relatively low work function value compared to the first electrode 210, and may be a cathode. For example, the second electrode 220 may include, but is not limited to, aluminum (Al), magnesium (Mg), calcium (Ca), silver (Ag), alloy thereof or combination thereof such as aluminum-magnesium alloy (Al—Mg) and Ag:Mg. For example, when the second electrode is made of Ag:Mg, Ag and Mg can be admixed with, but is not limited to, a weight ratio of about 5:1 to about 10:1, for example, about 8:1 to about 10:1. When the organic light emitting display device 100 is a top-emission type, the second electrode 220 is thin so as to have light-transmissive (semi-transmissive) property.

In addition, an encapsulation film 170 may be disposed over the second electrode 220 in order to prevent outer moisture from penetrating into the organic light emitting diode D. The encapsulation film 170 may have, but is not limited to, a laminated structure of a first inorganic insulating film 172, an organic insulating film 174 and a second inorganic insulating film 176. The encapsulation film 170 may be omitted.

A polarizing plate may be formed to reduce reflection of external light. For example, the polarizing plate may be a circular polarizing plate. When the organic light emitting display device 100 is a bottom-emission type, the polarizing plate may be disposed under the substrate 102. Alternatively, when the organic light emitting display device 100 is a top-emission type, the polarizing plate may be disposed over the encapsulation film 170. In addition, a cover window may be attached to the encapsulation film 170 or the polarizer. In this case, the substrate 110 and the cover window may have a flexible property, thus the organic light emitting display device 100 may be a flexible display device.

Figure 3:
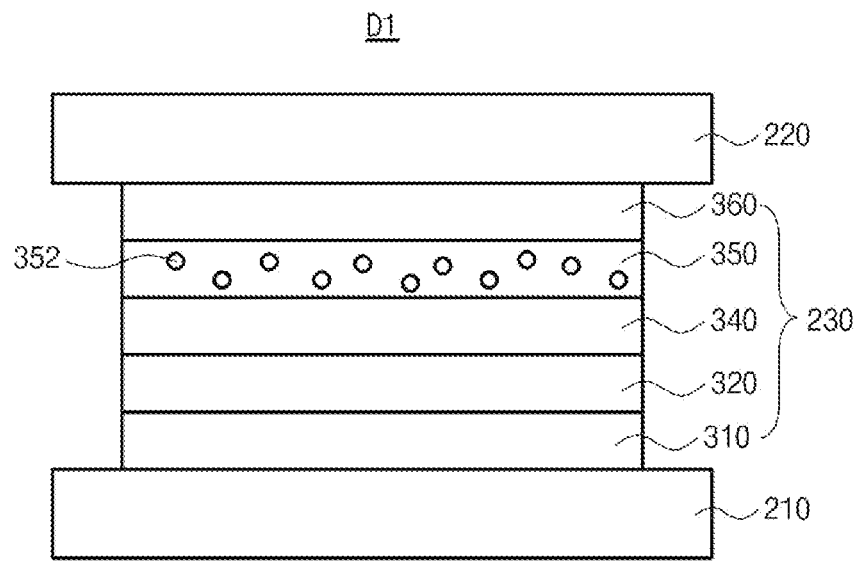
FIG. 3 is a schematic cross-sectional view illustrating an organic light emitting diode having a single emitting part in accordance with one exemplary aspect of the present disclosure.

Now, we will describe the OLED D including the organic compound in more detail. FIG. 3 is a schematic cross-sectional view illustrating an organic light emitting diode having a single emitting part in accordance with an exemplary embodiment of the present disclosure. As illustrated in FIG. 3, the organic light emitting diode (OLED) D1 in accordance with the present disclosure includes first and second electrodes 210 and 220 facing each other and an emissive layer 230 disposed between the first and second electrodes 210 and 220. The organic light emitting display device 100 includes a red (R) pixel region, a green (G) pixel region and a blue (B) pixel region, and the OLED D1 may be disposed in the blue (B) pixel region.

One of the first and second electrodes 210 and 220 is an anode and the other of the first and second electrodes 210 and 220 is a cathode. As an example, the first electrode 210 may be a cathode injecting holes and the second electrode 220 may be a cathode injecting electrons. In addition, one of the first and second electrodes 210 and 220 is a reflective electrode and the other of the first and second electrodes 210 and 220 is a transmissive (semi-transmissive) electrode. As an example, each of the first and second electrodes 210 and 220 may have a thickness of, but is not limited to, about 100 Å to about 2000 Å, for example, about 100 Å to about 1000 Å.

The emissive layer 230 includes an EML 340 disposed between the first and second electrodes 210 and 220. Also, the emissive layer 230 may comprise at least one of an HTL 320 disposed between the first electrode 210 and the EML 340 and an ETL 350 disposed between the second electrode 220 and the EML 340. In addition, the emissive layer 230 may further comprise at least one of an HIL 310 disposed between the first electrode 210 and the HTL 320 and an EML 360 disposed between the second electrode 220 and the ETL 350. Alternatively, the emissive layer 230 may further comprise an EBL disposed between the HTL 320 and the EML 340 and/or an HBL 350 disposed between the EML 340 and the ETL 350.

The HIL 310 is disposed between the first electrode 210 and the HTL 320 and improves an interface property between the inorganic first electrode 210 and the organic HTL 320. In one exemplary embodiment, the HIL 310 may include, but is not limited to, 4,4'4''-Tris(3-methylphenylamino)triphenylamine (MTDATA), 4,4',4''-Tris(N,N-diphenyl-amino)triphenylamine (NATA), 4,4',4''-Tris(N-(naphthalene-1-yl)-N-phenyl-amino)triphenylamine (1T-NATA), 4,4',4''-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4''-diamine (NPB; NPD), 1,4,5,8,9,11-Hexaazatriphenylenehexacarbonitrile (Dipyrazino[2,3-f:2',3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS), 2,3,5,6-tetrafluoro-7,7,8,8-tetracyanoquinodimethane (F4TCNQ), N-(biphenyl-4-yl)-9, 9-dimethyl-N-(4-(9-phenyl-9H-carbazol-3-yl)phenyl)-9H-fluoren-2-amine, N,N'-diphenyl-N,N'-di[4-(N,N'-diphenyl-amino)phenyl]benzidine (NPNPB) and combination thereof. The HIL 310 may be omitted in compliance of the OLED D1 property.

The HTL 320 disposed between the HIL 310 and the EML 340 may include, but is not limited to, N,N'-Diphenyl-N, N'-bis(3-methylphenyl-1,1'-biphenyl-4,4'-diamine (TPD), NPB (NPD), N,N'-bis[4-[bis(3-methylphenyl)amino]phenyl]-N,N'-diphenyl-[1,1'-biphenyl]-4,4'-diamine (DNTPD), 4,4'-bis(N-carbazolyl)-1,1'-biphenyl (CBP), Poly[N,N'-bis (4-butylphenyl)-N,N'-bis(phenyl)-benzidine] (Poly-TPD), Poly [(9, 9-dioctylfluorenyl-2, 7-diyl)-co-(4,4'-(N-(4-sec-butylphenyl)diphenylamine))] (TFB), 1,1-bis(4-(N,N'-di(p-tolyl)amino)phenyl)cyclohexane (TAPC), 3,5-Di(9H-carbazol-9-yl)-N,N-diphenylaniline (DCDPA), N-(biphenyl-4-yl)-9, 9-dimethyl-N-(4-(9-phenyl-9H-carbazol-3-yl) phenyl)-9H-fluoren-2-amine, N-(biphenyl-4-yl)-N-(4-(9-phenyl-9H-carbazol-3-yl)phenyl)biphenyl-4-amine, N-([1, 1'-Biphenyl]-4-yl)-9,9-dimethyl-N-(4-(9-phenl-9H-carbazol-3-yl)phenyl)-9H-fluoren-2-amine and combination thereof.

The EML 340 may comprise a host (first host) and a dopant (first dopant) where substantial emission is occurred. The EML 340 may emit red, green and/or blue light. In one exemplary aspect, the EML 340 may emit blue light.

When the EML 340 emits blue light, the first host may include an anthracene-based organic compound. As an example, the anthracene-based organic compound may have the following structure of Formula 5:

[Formula 5]

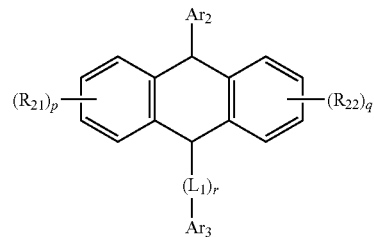

wherein each of $R_{21}$ and $R_{22}$ is independently protium or deuterium; each of $Ar_2$ and $Ar_3$ is independently a $C_6$-$C_{30}$ aryl group or a $C_4$-$C_{30}$ hetero aryl group; $L_1$ is a $C_6$-$C_{30}$ arylene group; each of p and q is a number of deuterium substituent and is independently an integer of 0 to 4; and r is 0 or 1.

For example, $Ar_2$ in Formula 5 may be phenyl or naphthyl, $Ar_3$ in Formula 5 may be naphthyl, dibenzofuranyl or fused dibenzofuranyl and $L_1$ in Formula 5 may be phenylene. As an example, the anthracene-based organic compound used as the first host may be selected from, but is not limited to, the following compounds having the structure of Formula 6:

[Formula 6]

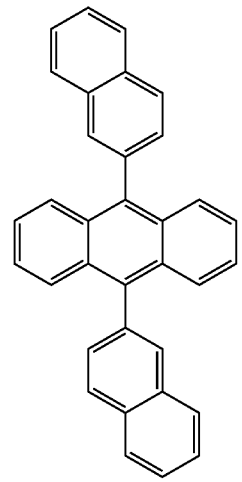

Host 1

Host 2
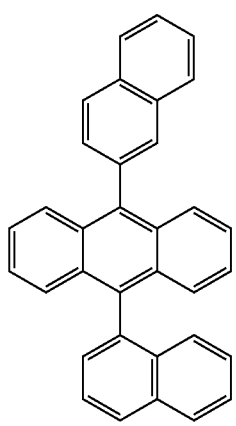
Host 6
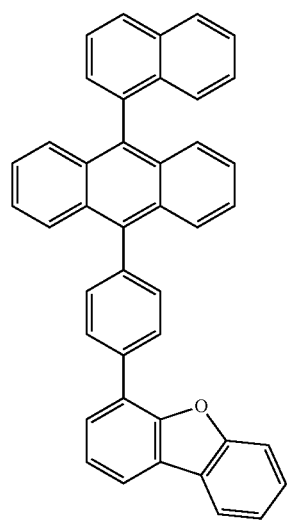
Host 3
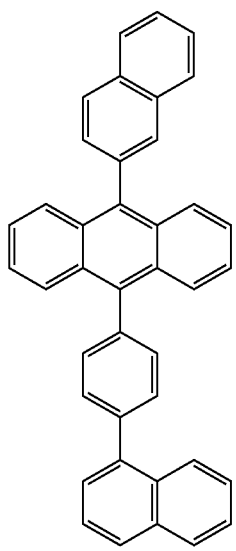
Host 7
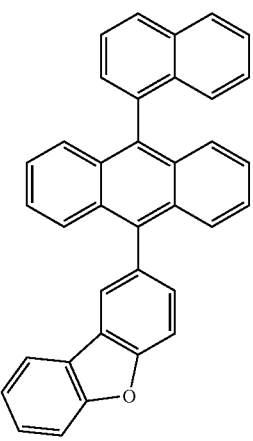
Host 4
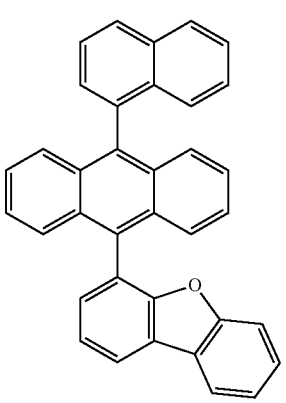
Host 8
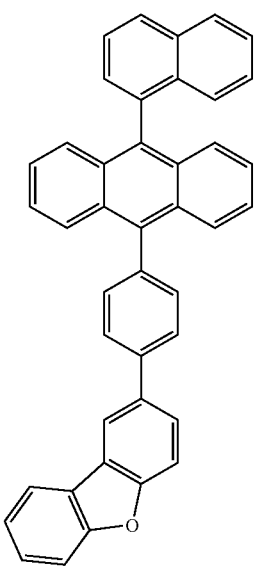

Host 9
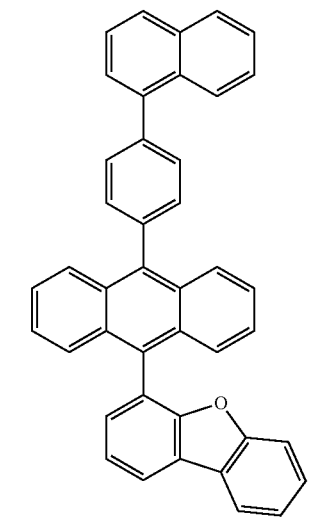
Host 9
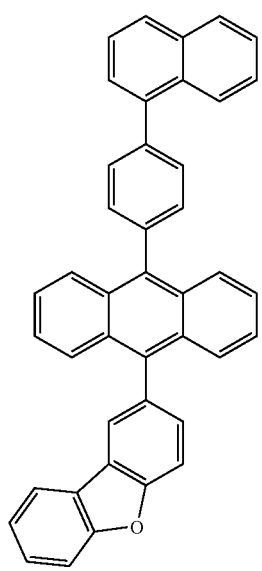
Host 10
Host 11
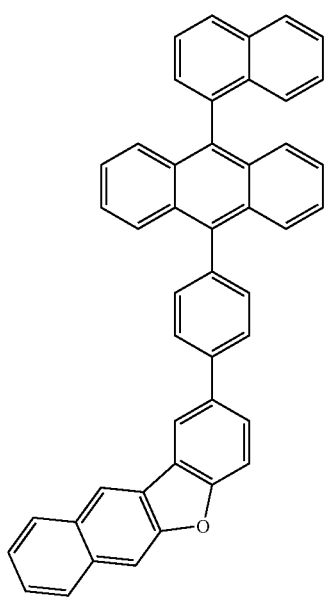
Host 12
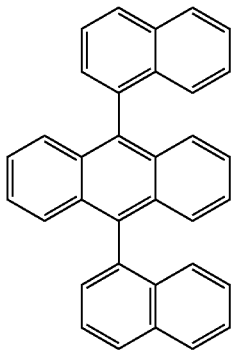
Host 13
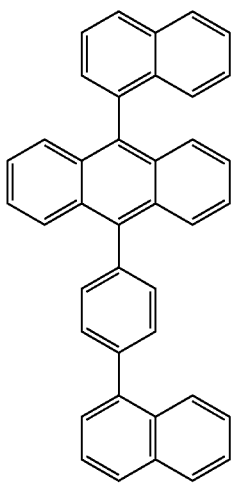

Host 14
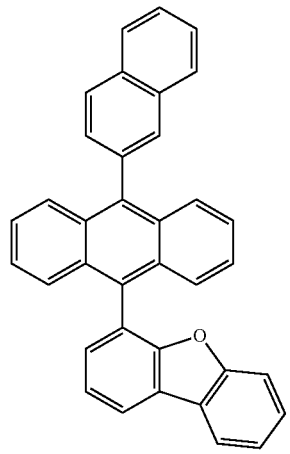
Host 15
Host 17
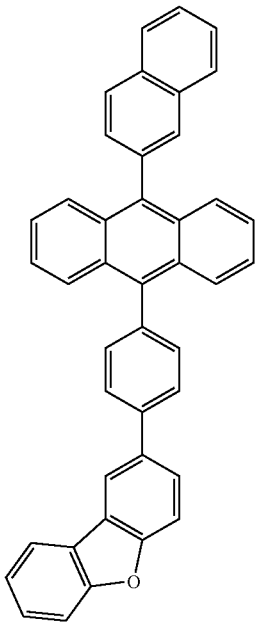
Host 16
Host 18
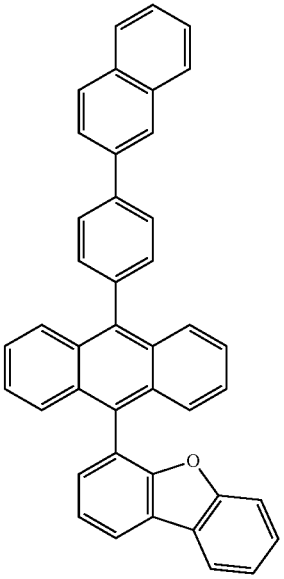

Host 19
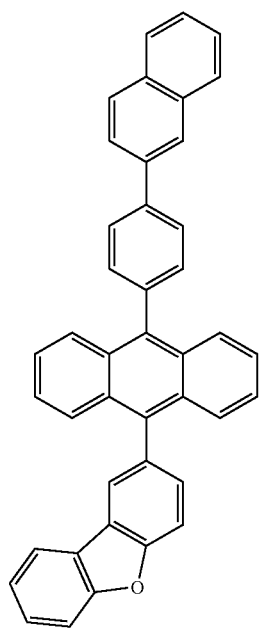
Host 20
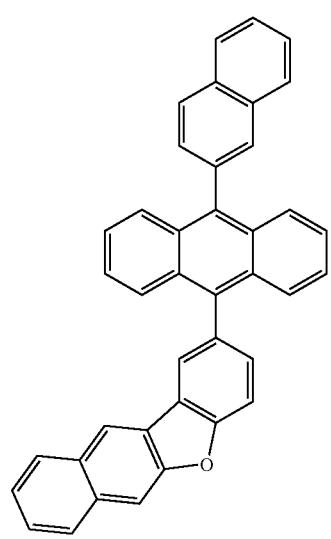
Host 21
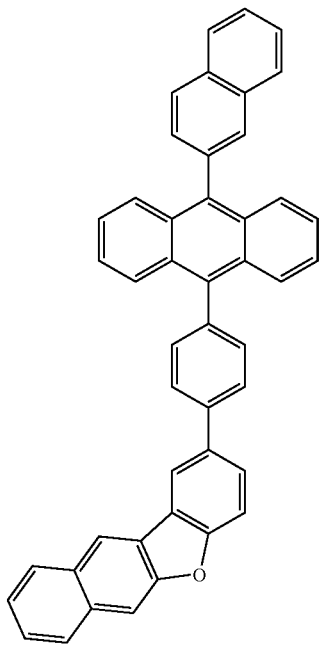
Host 22
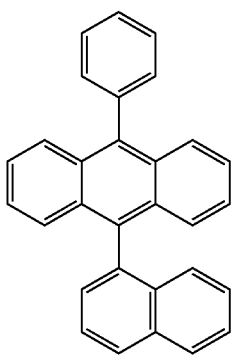
Host 23
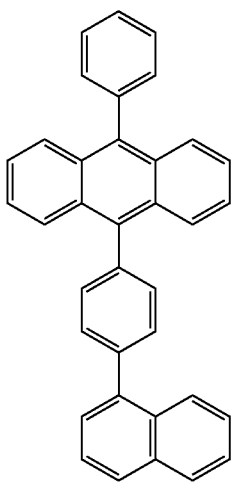

Host 24
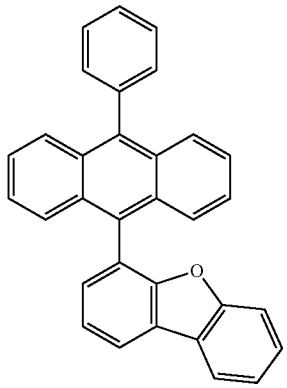
Host 25
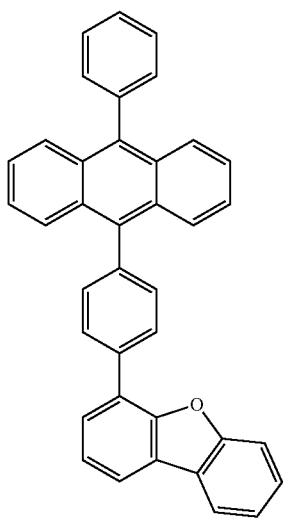
Host 26
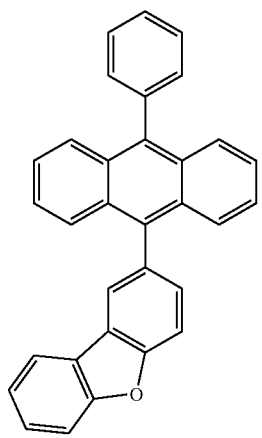
Host 27
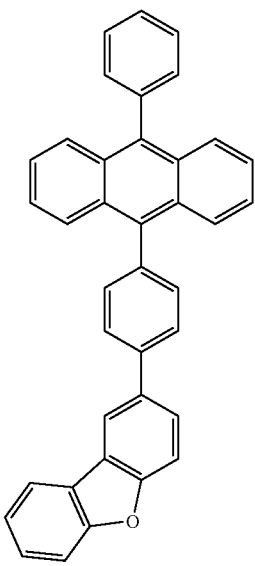
Host 28
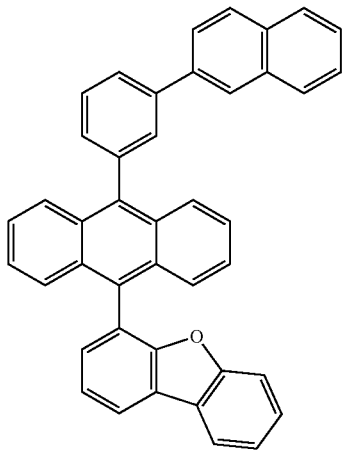
Host 29
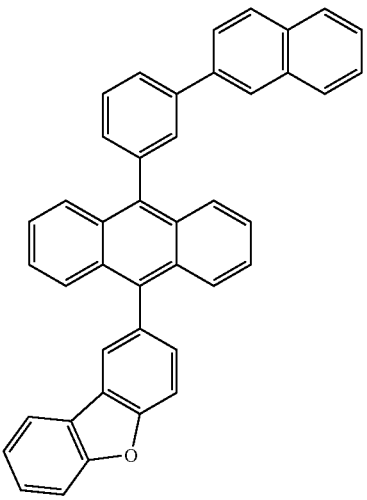

Host 30

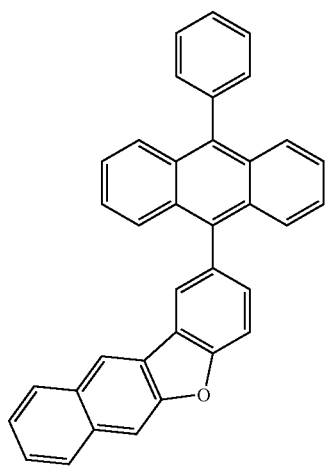

Host 31

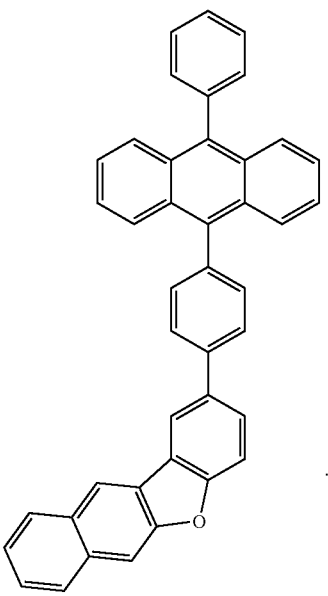

The first dopant emitting blue light may include a boron-based organic compound. The boron-based organic compound may have the following structure of Formula 7:

[Formula 7]

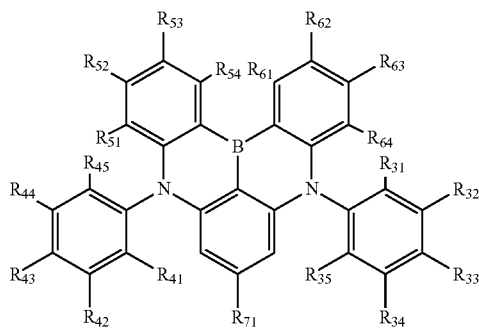

wherein each of $R_{31}$ to $R_{34}$, each of $R_{41}$ to $R_{44}$, each of $R_{51}$ to $R_{55}$ and each of $R_{61}$ to $R_{65}$ is independently selected from the group consisting of protium, deuterium, $C_1$-$C_{10}$ alkyl, $C_6$-$C_{30}$ aryl, $C_6$-$C_{30}$ aryl amino and $C_5$-$C_{30}$ hetero aryl, $R_{11}$ to $R_{14}$, $R_{21}$ to $R_{24}$, $R_{31}$ to $R_{35}$ and $R_{41}$ to $R_{45}$ may be identical to or different from each other, wherein each of the $C_6$-$C_{30}$ aryl and the $C_5$-$C_{30}$ hetero aryl may optionally be substituted with another $C_1$-$C_{10}$ alkyl, or each of two of $R_{31}$ to $R_{55}$ and two of $R_{41}$ to $R_{45}$ may form independently a $C_6$-$C_{10}$ aromatic ring or a $C_5$-$C_{10}$ hetero aromatic ring; and $R_{71}$ is selected from the group consisting of protium, deuterium, $C_1$-$C_{10}$ alkyl and $C_3$-$C_{15}$ cyclo alkyl, $C_6$-$C_{30}$ aryl and $C_5$-$C_{30}$ hetero aryl and $C_6$-$C_{30}$ aryl amino, wherein the $C_6$-$C_{30}$ aryl amino may be optionally substituted with at least one of another $C_1$-$C_{10}$ alkyl and another $C_6$-$C_{20}$ aryl.

When the aryl, the hetero aryl and/or the aryl amino, which may be each of $R_{31}$ to $R_{34}$, each of $R_{41}$ to $R_{44}$, each of $R_{51}$ to $R_{55}$, each of $R_{61}$ to $R_{65}$ and $R_{71}$, is substituted, the substituent may be, but is not limited to, $C_1$-$C_{10}$ alkyl, for example, $C_1$-$C_5$ alkyl such as methyl, tert-butyl and tert-pentyl.

For example, the aryl amino may comprise diphenyl amino and phenyl-naphthyl amino, the aryl may comprise phenyl and naphthyl each of which may be unsubstituted or at least one, for example, one or two $C_1$-$C_{10}$ alkyls, and the hetero aryl may comprise carbazolyl. The alkyl, which may be each of $R_{31}$ to $R_{34}$, each of $R_{41}$ to $R_{44}$, each of $R_{51}$ to $R_{55}$, each of $R_{61}$ to $R_{65}$ and $R_{71}$, may comprise $C_1$-$C_{10}$ alkyl, for example, $C_1$-$C_5$ alkyl such as methyl, ethyl, propyl, butyl (e.g. tert-butyl) and pentyl (e.g. tert-pentyl). As an example, each of the aryl amino, the aryl, the hetero aryl and the alkyl, which may be each of $R_{31}$ to $R_{34}$, each of $R_{41}$ to $R_{44}$, each of $R_{51}$ to $R_{55}$, each of $R_{61}$ to $R_{65}$ and $R_{71}$, may independently optionally further substituted with deuterium.

The aromatic ring or the hetero aromatic ring, which may be formed by each of two of $R_{31}$ to $R_{35}$ and two of $R_{41}$ to $R_{45}$, may comprise, but is not limited to, a benzofuran ring and a benzothiophene ring each of which may be independently unsubstituted or substituted with one to three $C_1$-$C_5$ alkyls.

The boron-based organic compound used as the first dopant may be selected from, but is not limited to, the following compounds having the structure of Formula 8:

[Formula 8]

Dopant 1

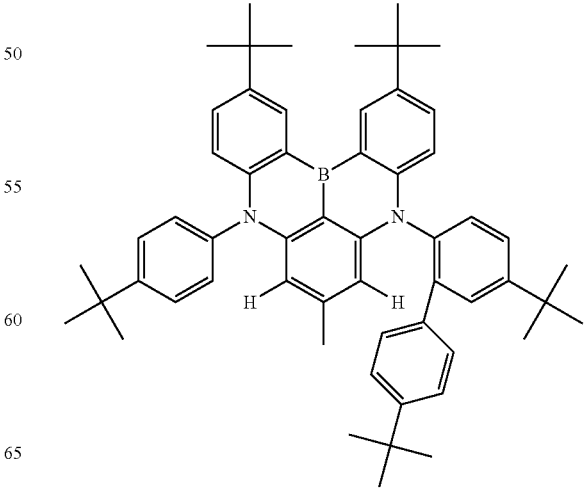

Dopant 2
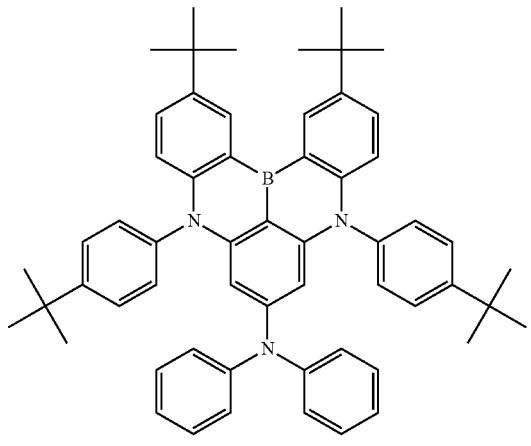
Dopant 5
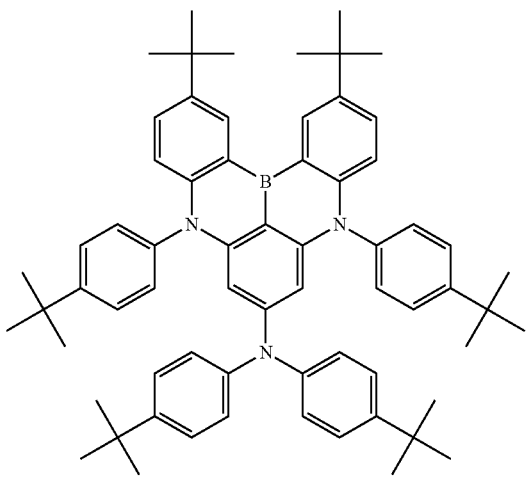
Dopant 3
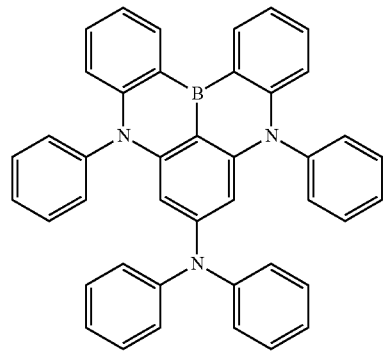
Dopant 6
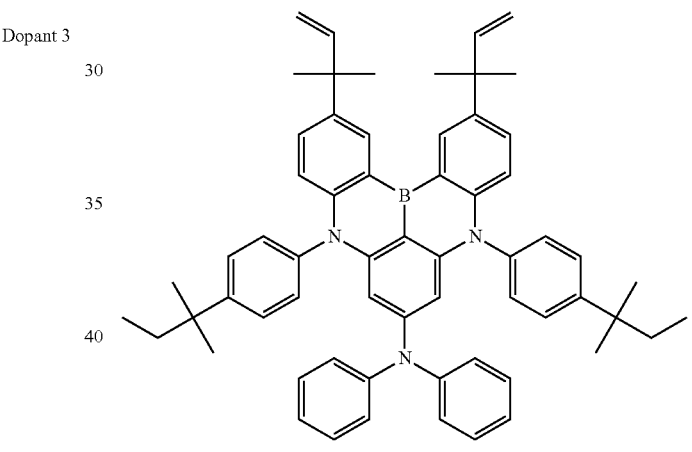
Dopant 4
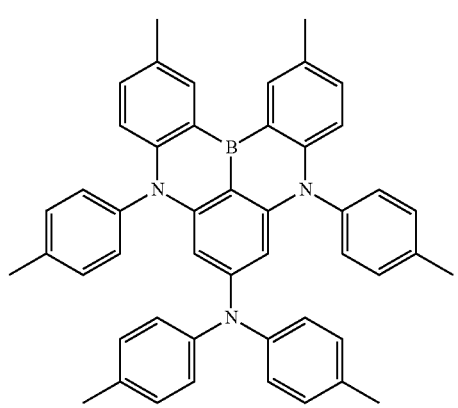
Dopant 7
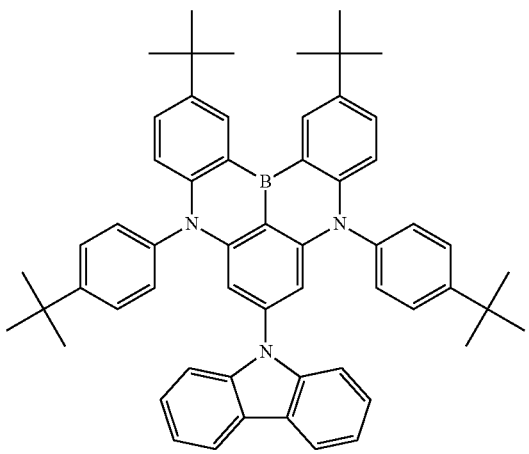

Dopant 8
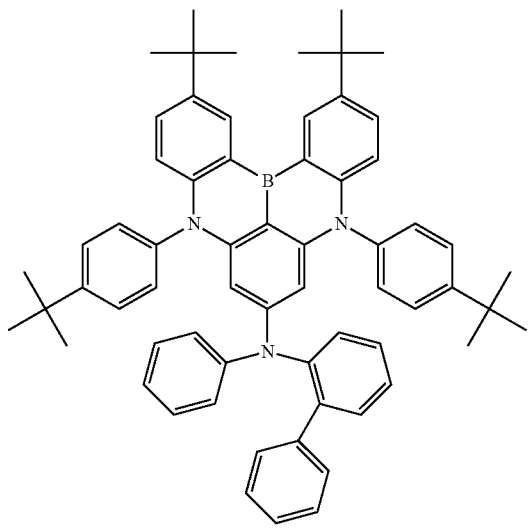
Dopant 9
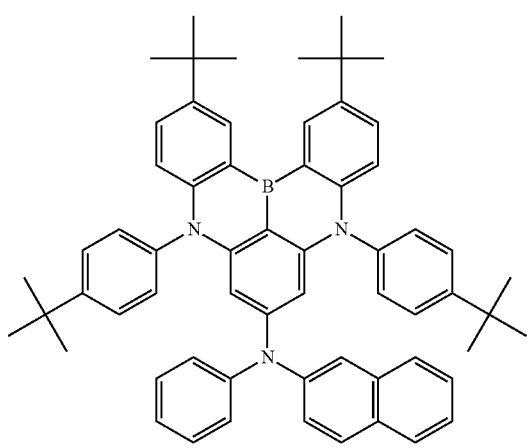
Dopant 10
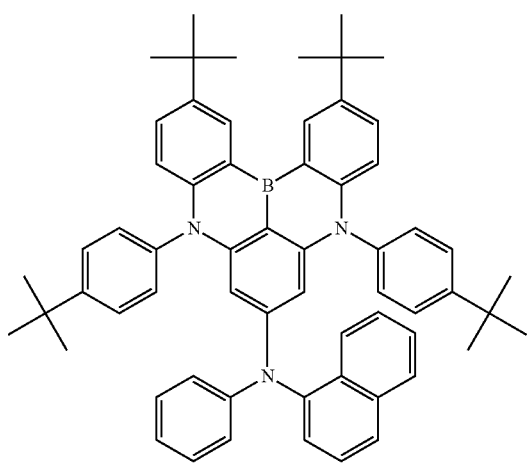
Dopant 11
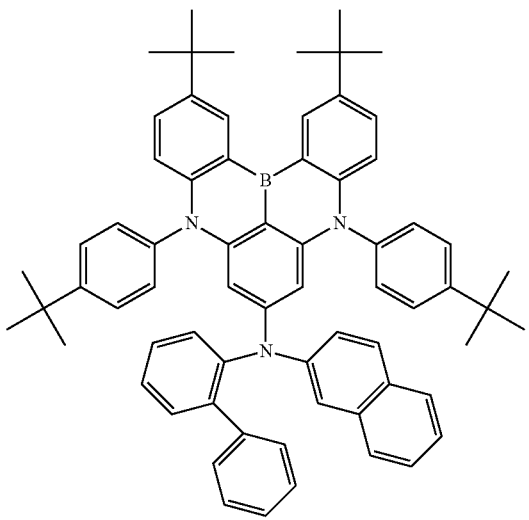
Dopant 12
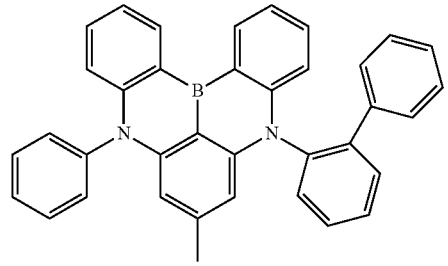
Dopant 13
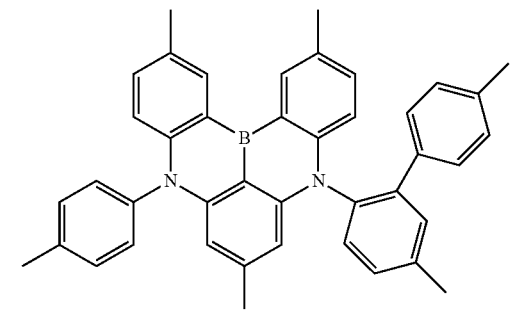
Dopant 14
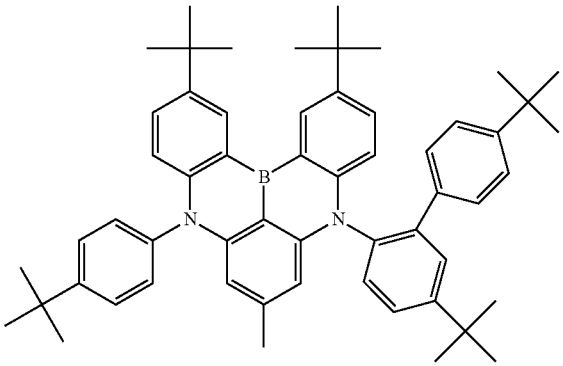

Dopant 15
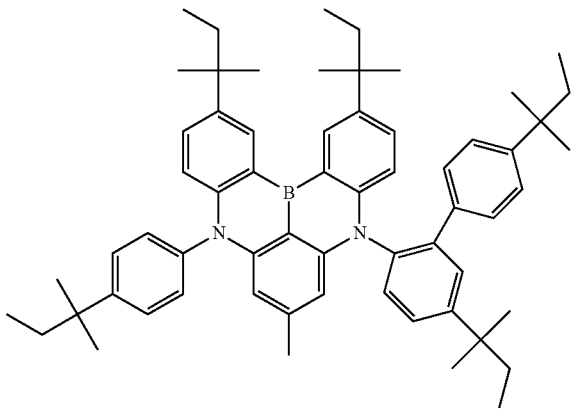

Dopant 16
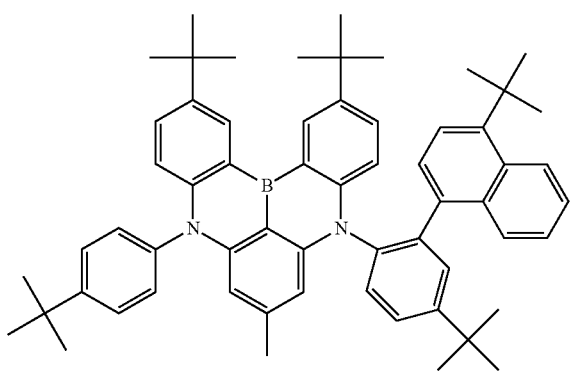

Dopant 17
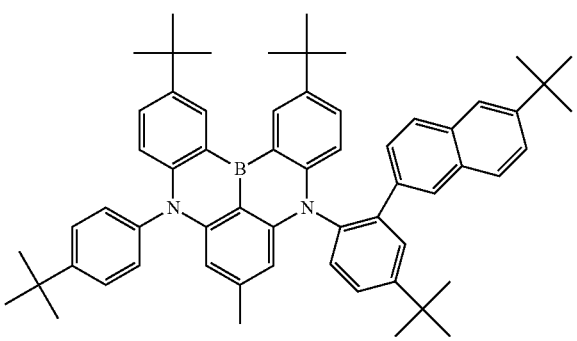

Dopant 18
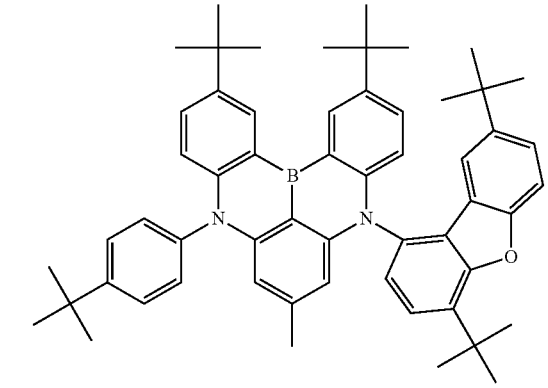

Dopant 19
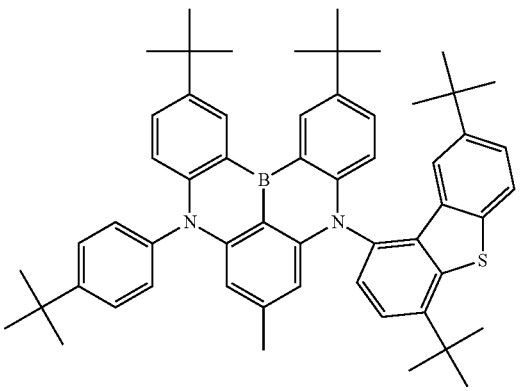

For example, the contents of the first dopant in the EML 340 may be, but is not limited to, about 1 wt % to about 10 wt %, for example, about 1 wt % to about 5 wt %.

The ETL 350 provides electrons stably to the EML 340 via facilitate electron transportations. The ETL 350 may include an electron transport material 352 that is the organic compound having the structure of Formulae 1 to 4.

Alternatively, the ETL 350 may include an alkali metal and/or an alkaline earth metal doped with the electron transport material 352 that is the organic compound having the structure of Formulae 1 to 4. The alkali metal and the alkaline earth metal as the dopant of the ETL 350 may include, but is not limited to, Li, Na, K, Cs, Mg, Sr, Ba, Ra and combination thereof. The contents of the alkali metal and/or the alkaline earth metal in the ETL 350 may be, but is not limited to, about 1 wt % to about 20 wt %, for example, about 1 wt % to about 5 wt %.

The EIL 360 is disposed between the second electrode 220 and the ETL 350, and can improve physical properties of the second electrode 220 and therefore, can enhance the lifetime of the OLED D1. In one exemplary aspect, the EIL 360 may comprise, but is not limited to, an alkali metal halide or an alkaline earth metal halide such as NaF, LiF, CsF, $BaF_2$, $MgF_2$ and the like, and/or an organic metal compound such as lithium quinolate (Liq), lithium benzoate, sodium stearate, and the like.

Alternatively, the EIL 360 may include an alkali metal such as Li, Na and Cs, an alkaline earth metal such as Mg, Sr, Ba and Ra and/or a lanthanide metal such as Yb doped with the alkali metal halide, the alkaline earth metal halide and the organic metal compound. In this case, the alkali metal halide/alkaline earth metal halide/organic compound as the host and the alkali metal/alkaline earth metal/lanthanide metal as the dopant may be admixed with a weight ratio of, but is not limited to, about 4:1 to about 1:4, for example, about 2:1 to about 1:2.

Since the organic compound having the structure of Formulae 1 to 4 includes the fused hetero aromatic moiety substituted with at least one deuterium, it has excellent thermal stability. In addition, since the organic compound includes the phenanthroline moiety having relatively electron-rich nitrogen atoms, it has excellent electron transport property. Accordingly, the ETL 340 includes the organic compound having the structure of Formulae 1 to 4 so that the OLED D1 can lower its driving voltage as well as maximize its luminous efficiency and luminous lifespan.

Figure 4:
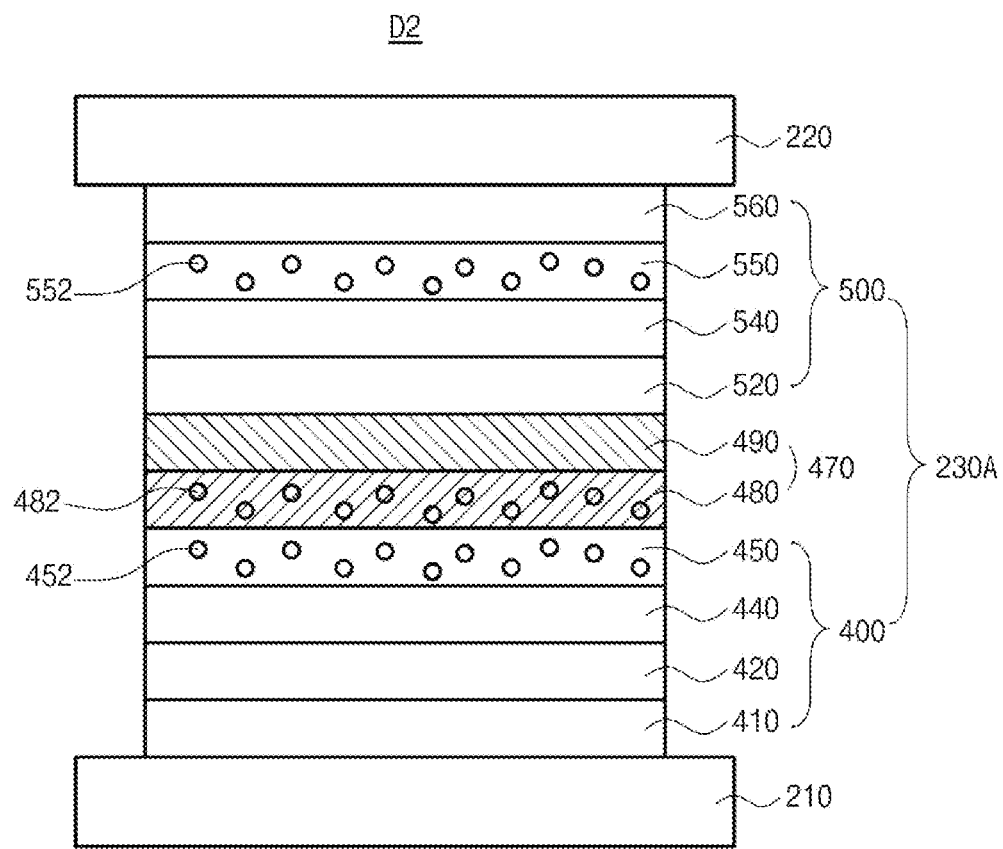
FIG. 4 is a schematic cross-sectional view illustrating an organic light emitting diode having two emitting parts in accordance with another exemplary aspect of the present disclosure.

FIG. 4 is a schematic cross-sectional view illustrating an organic light emitting diode having two emitting parts in accordance with another exemplary aspect of the present disclosure. As illustrated in FIG. 4, the OLED D2 includes first and second electrodes 210 and 220 facing each other and an emissive layer 230A disposed between the first and second electrodes 210 and 220. The organic light emitting display device 100 (FIG. 2) includes a red (R) pixel region, a green (G) pixel region and a blue (B) pixel region, and the OLED D2 may be located in any pixel region. For example, the OLED D2 may be located in the blue (B) pixel region.

One of the first and second electrodes 210 and 220 is an anode and the other of the first and second electrodes 210 and 220 is a cathode. As an example, the first electrode 210 may be a cathode injecting holes and the second electrode 220 may be a cathode injecting electrons. In addition, one of the first and second electrodes 210 and 220 is a reflective electrode and the other of the first and second electrodes 210 and 220 is a transmissive (semi-transmissive) electrode.

The emissive layer 230A includes a first emitting part 400 and a second emitting part 500 and a charge generation layer (CGL) 470 disposed between the first emitting part 400 and the second emitting part 500. Accordingly, the first emitting part 400, the CGL 470 and the second emitting part 500 are sequentially formed over the first electrode 210. In other words, the first emitting part 400 is disposed between the first electrode 210 and the CGL 470 and the second emitting part 500 is disposed between the second electrode 220 and the CGL 470.

The first emitting part 400 includes a first EML (lower EML, EML1) 440. The first emitting part 400 may further include at least one of an HIL 410 disposed between the first electrode 210 and the EML1 440, a first HTL (lower HTL, HTL1) 420 disposed between the HIL 410 and the EML1 440 and a first ETL (lower ETL, ETL1) 450 disposed between the EML1 440 and the CGL 470. Alternatively, the first emitting part 400 may further include a first EBL (lower EBL, EBL1) disposed between the HTL1 420 and the EML1 440.

The second emitting part 500 includes a second EML (upper EML, EML2) 540. The second emitting part 400 may further include at least one of a second HTL (upper HTL, HTL2) 520 disposed between the CGL 470 and the EML2 540, a second ETL (upper ETL, ETL2) 550 disposed between the second electrode 220 and the EML2 540 and an EIL 560 disposed between the second electrode 220 and the ETL2 550. Alternatively, the second emitting part 500 may further include a second EBL (upper EBL, EBL2) disposed between the HTL2 520 and the EML2 540.

The HIL 410, the HTL1 420, the HTL2 520 and the EIL 560 may have substantially the same structure and components as described above.

The EML1 440 may include a first host and a first dopant, and the EML2 540 may include a second host and a second dopant. In one exemplary aspect, each of the first host and the second host may comprise independently the anthracene-based organic compound having the structure of Formulae 5 to 6 and each of the first dopant and the second dopant may comprise independently the boron-based organic compound having the structure of Formulae 7 to 8. The first host may be identical to or different from the second host and the first dopant may be identical to or different from the second dopant. The contents of the first dopant and the second dopant in each of the EML1 440 and the EML2 540 may be, but is not limited to, about 1 wt % to about 10 wt %, for example, about 1 wt % to about 5 wt %.

In one exemplary aspect, each of the ETL1 450 and the ETL2 550 may include independently, but is not limited to, at least one of oxadiazole-based compounds, triazole-based compounds, phenanthroline-based compounds, benzoxazole-based compounds, benzothiazole-based compounds, benzimidazole-based compounds, triazine-based compounds, and the like.

As an example, each of the ETL1 450 and the ETL2 550 may include independently, but is not limited to, tris-(8-hydroxyquinoline aluminum ($Alq_3$), Bis(2-methyl-8-quinolinolato-N1, O8)-(1,1'-biphenyl-4-olato)aluminum (BAlq), Liq, 2-biphenyl-4-yl-5-(4-t-butylphenyl)-1,3,4-oxadiazole (PBD), spiro-PBD, 1,3,5-Tris(N-phenylbenzimidazol-2-yl)benzene (TPBi), 4,7-diphenyl-1,10-phenanthroline (Bphen), 2,9-Bis(naphthalene-2-yl)4,7-diphenyl-1,10-phenanthroline (NBphen), 2,9-Dimethyl-4,7-diphenyl-1,10-phenaathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)] (PFNBr), tris(phenylquinoxaline) (TPQ), diphenyl-4-triphenysilyl-phenylphosphine oxide (TSPO1), 2-[4-(9,10-di-2-naphthalen-2-yl-2-anthracen-2-yl)phenyl]1-phenyl-1H-benzimidazole (ZADN) and combination thereof.

Alternatively, each of the ETL1 450 and the ETL2 550 may include a first electron transport material 452 and a second electron transport material 552, respectively, each of which is independently the organic compound having the structure of Formulae 1 to 4.

In still another alternative aspect, each of the ETL1 450 and the ETL2 550 may further include independently the alkali metal and/or the alkaline earth metal doped to each of the first and second electron transport materials 452 and 552. The contents of the alkali metal and/or the alkaline earth metal in each of the ETL1 450 and the ETL2 550 may be, but is not limited to, about 1 wt % to about 10 wt %, for example, about 1 wt % to about 5 wt %.

The CGL 470 is disposed between the first emitting part 400 and the second emitting part 500. The CGL 470 includes an N-type CGL (N-CGL) 480 disposed between the ETL1 450 and the HTL2 520 and a P-type CGL (P-CGL) 490 disposed between the N-CGL 480 and the HTL2 520. The N-CGL 480 transports electrons to the EML1 440 of the first emitting part 400 and the P-CGL 490 transport holes to the EML2 540 of the second emitting part 500.

The N-CGL 480 may be an organic layer including an N-type host, and optionally an N-type dopant. For example, the N-type host may include an N-type charge generation material 482 that may be the organic compound having the structure of Formulae 1 to 4.

As an example, the N-type dopant may include an alkali metal such as Li, Na, K and Cs and/or an alkaline earth metal such as Mg, Sr, Ba and Ra. The N-type dopant allows the N-CGL 480 to have excellent electron generation and electron injection. When the N-CGL 480 includes the alkali metal and/or the alkaline earth metal, the alkali metal and/or the alkaline earth metal as the N-type dopant binds to the N-type charge generation material 482, which may be the organic compound having the structure of Formulae 1 to 4, in order to form a gap state. Accordingly, as energy level bandgap between the N-CGL 480 and the P-CGL 490 becomes small, electron injection property from the N-CGL 480 to the ETL1 450 may be improved. For example, the contents of the N-type dopant in the N-CGL 480 may be, but is not limited to, about 1 wt % to about 10 wt %, for example, about 1 wt % to about 5 wt %.

The P-type CGL 490 may be an organic layer including a P-type host, and optionally a P-type dopant. For example, the P-type host may include the organic compound used in the HIL 420 and/or the HTL1 and HTL2 420 and 520.

As an example, the P-type host may include, but is not limited to, NPB, TPD, N,N,N',N'-tetraphenylenyl-benzidine (TNB), HAT-CN and combination thereof. The P-type dopant may include, but is not limited to, F4-TCNQ, 1,3,4,5,7,8-hexafluorotetracyanonaphthoquiodimethane (F6-TCNNQ), FeCl3, FeF3, SbCl5 and combination thereof. When the P-CGL 490 includes the P-type dopant, the contents of the P-type dopant in the P-CGL 490 may be, but is not limited to, about 1 wt % to about 40 wt %, for example, about 3 wt % to about 30 wt %.

In this aspect, each of the ETL1 450, the ETL2 550 and the N-CGL 480 includes the first electron transport material 452, the second electron transport material 552 and the N-type charge generation material 482, respectively, at least one of which may be the organic compound having the structure of Formulae 1 to 4. Accordingly, the OLED D2 can lower its driving voltage and improve its luminous property.

Figure 5:
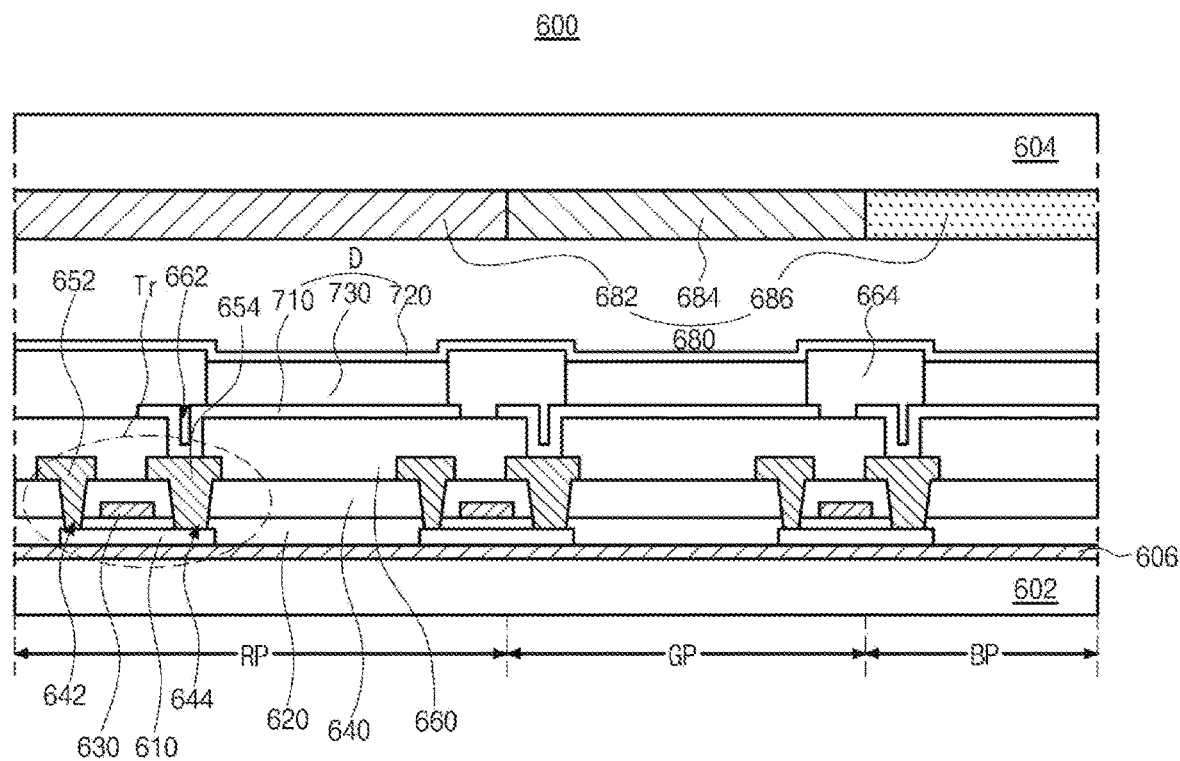
FIG. 5 is a schematic cross-sectional view illustrating an organic light emitting display device as an example of an organic light emitting device in accordance with another exemplary aspect of the present disclosure.

In the above aspect, an OLED and an organic light emitting display device including one or two emitting part emitting blue light. In another exemplary aspect, an organic light emitting display device can implement full-color including white color. Now, we will explain the white OLED and an organic light emitting device including the white OLED. FIG. 5 is a schematic cross-sectional view illustrating an organic light emitting display device in accordance with another exemplary aspect of the present disclosure.

As illustrated in FIG. 5, the organic light emitting display device 600 comprises a first substrate 602 that defines each of a red pixel region RP, a green pixel region GP and a blue pixel region BP, a second substrate 604 facing the first substrate 602, a thin film transistor Tr over the first substrate 602, an organic light emitting diode (OLED) D disposed between the first and second substrates 602 and 604 and emitting white (W) light and a color filter layer 680 disposed between the OLED D and the second substrate 604.

Each of the first and second substrates 602 and 604 may include, but is not limited to, glass, flexible material and/or polymer plastics. For example, each of the first and second substrates 602 and 604 may be made of PI, PES, PEN, PET, PC and combination thereof. The first substrate 602, over which a thin film transistor Tr and an organic light emitting diode D are arranged, forms an array substrate.

A buffer layer 606 may be disposed over the first substrate 602, and the thin film transistor Tr is disposed over the buffer layer 606 correspondingly to each of the red pixel region RP, the green pixel region GP and the blue pixel region BP. The buffer layer 606 may be omitted.

A semiconductor layer 610 is disposed over the buffer layer 606. As an example, the semiconductor layer 610 may be made of oxide semiconductor material or polycrystalline silicon.

A gate insulating layer 620 including an insulating material, for example, inorganic insulating material such as silicon oxide ($SiO_x$) or silicon nitride ($SiN_x$) is disposed on the semiconductor layer 610.

A gate electrode 630 made of a conductive material such as a metal is disposed over the gate insulating layer 620 so as to correspond to a center of the semiconductor layer 610. An interlayer insulting layer 640 including an insulating material, for example, inorganic insulating material such as silicon oxide ($SiO_x$) or silicon nitride ($SiN_x$), or an organic insulating material such as benzocyclobutene or photo-acryl, is disposed on the gate electrode 630.

The interlayer insulating layer 640 has first and second semiconductor layer contact holes 642 and 644 that expose both sides of the semiconductor layer 610. The first and second semiconductor layer contact holes 642 and 644 are disposed over opposite sides of the gate electrode 630 with spacing apart from the gate electrode 630.

A source electrode 652 and a drain electrode 654, which are made of a conductive material such as a metal, are disposed on the interlayer insulating layer 640. The source electrode 652 and the drain electrode 654 are spaced apart from each other with respect to the gate electrode 630, and contact both sides of the semiconductor layer 610 through the first and second semiconductor layer contact holes 642 and 644, respectively.

The semiconductor layer 610, the gate electrode 630, the source electrode 652 and the drain electrode 654 constitute the thin film transistor Tr, which acts as a driving element.

Although not shown in FIG. 5, a gate line and a data line, which cross each other to define a pixel region, and a switching element, which is connected to the gate line and the data line, is may be further formed in the pixel region. The switching element is connected to the thin film transistor Tr, which is a driving element. In addition, a power line is spaced apart in parallel from the gate line or the data line, and the thin film transistor Tr may further include a storage capacitor configured to constantly keep a voltage of the gate electrode for one frame.

A passivation layer 660 is disposed on the source and drain electrodes 652 and 654 with covering the thin film transistor Tr over the whole first substrate 602. The passivation layer 660 has a drain contact hole 662 that exposes the drain electrode 654 of the thin film transistor Tr.

The OLED D is located over the passivation layer 660. The OLED D includes a first electrode 710 that is connected to the drain electrode 654 of the thin film transistor Tr, a second electrode 720 facing from the first electrode 710 and an emissive layer 730 disposed between the first and second electrodes 710 and 720.

One of the first electrode 710 formed for each pixel region and the second electrode 720 disposed integrally over a whole display area may be an anode, and the other of the first electrode 710 and the second electrode 720 may be a cathode. In addition, one of the first and second electrodes 710 and 720 may be a transmissive (semi-transmissive) electrode, and the other of the first and second electrodes 710 and 720 may be a reflective electrode.

For example, the first electrode 710 may be an anode and may include a conductive material having relatively high work function value. For example, the first electrode 710 may include ITO, IZO, ITZO, SnO, ZnO, ICO, AZO, and the like.

The second electrode 720 is disposed over the first substrate 602 above which the emissive layer 730 is disposed. The second electrode 720 may be a cathode and may include a conductive material with a relatively low work function value, for example, low resistance metal. As an example, the second electrode 720 may include, but is not limited to, Al, Mg, Ca, Ag, alloy thereof or combination thereof such as Al—Mg or Ag:Mg.

When the organic light emitting display device 600 is a bottom-emission type, the first electrode 710 may have a single layered structure of conductive oxide. Alternatively, when the organic light emitting display device 600 is a top-emission a reflective electrode or a reflective layer may be formed under the first electrode 710. For example, the reflective electrode or the reflective layer may include, but is not limited to, Ag or APC alloy. In the OLED D of the top-emission type, the first electrode 710 may have a triple-layered structure of ITO/Ag/ITO or ITO/APC/ITO. The second electrode 720 is thin so as to have light-transmissive (semi-transmissive) property.

A bank layer 664 is disposed on the passivation layer 660 in order to cover edges of the first electrode 710. The bank layer 664 exposes a center of the first electrode 710 corresponding to each of the red pixel RP, the green pixel GP and the blue pixel BP. The bank layer 664 may be omitted.

Figure 6:
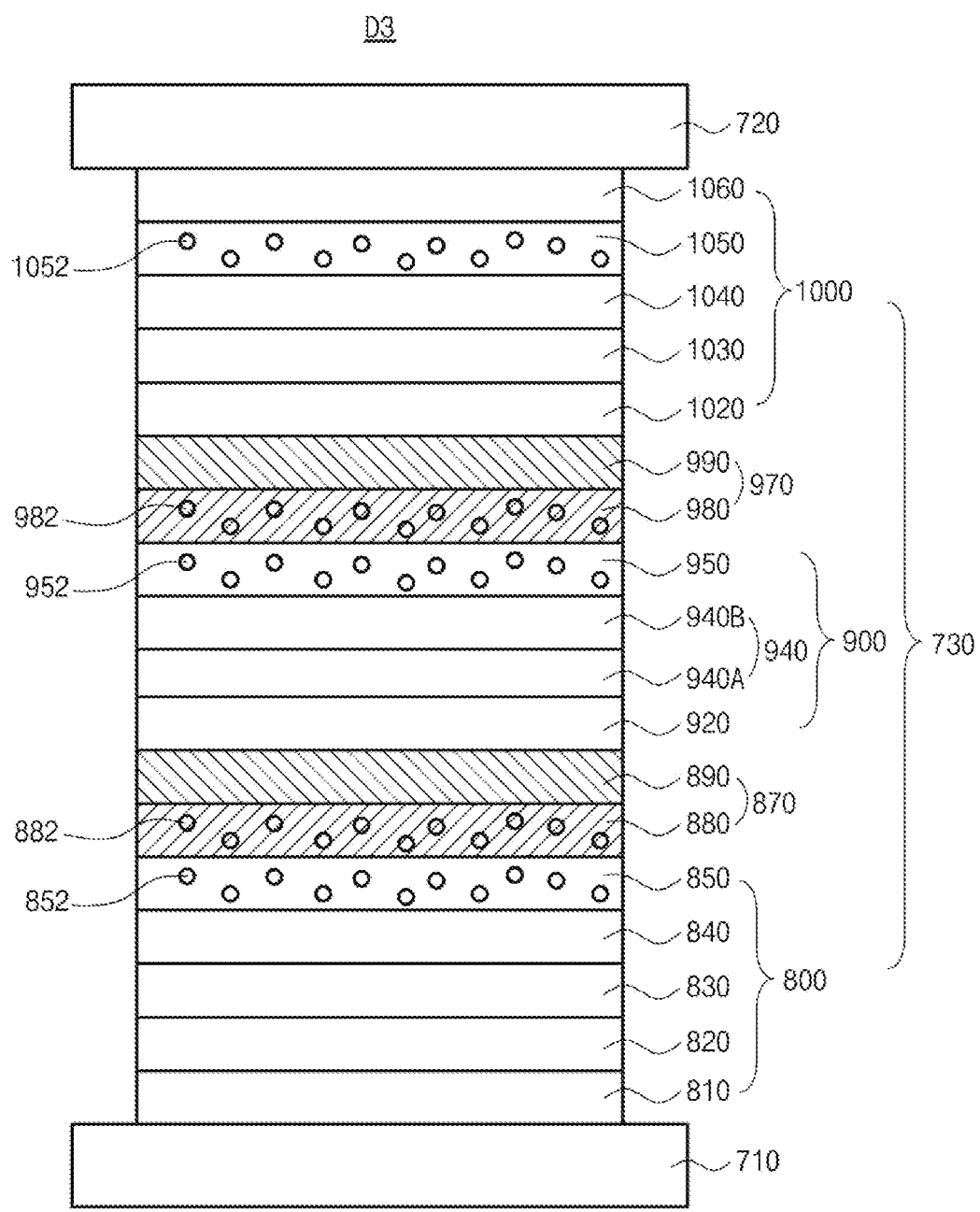
FIG. 6 is a schematic cross-sectional view illustrating an organic light emitting diode having three emitting parts in accordance with still another exemplary aspect of the present disclosure.

An emissive layer 730 is disposed on the first electrode 710. As illustrated in FIG. 6, the emissive layer 730 may include multiple emitting parts 800, 900 and 1000. Each emitting part may comprise respective EML. In addition, each emitting part may further include at least one of a HIL, a HTL, an EBL, an ETL and an EIL.

The color filter layer 680 is disposed over the OLED D and includes a red color filter 682, a green color filter 684 and a blue color filter 686 each of which is disposed correspondingly to the red pixel region RP, the green pixel region GP and the blue pixel region BP, respectively. Although not shown in FIG. 5, the color filter layer 680 may be attached to the OLED D through an adhesive layer. Alternatively, the color filter layer 680 may be disposed directly on the OLED D.

In addition, an encapsulation film may be disposed over the second electrode 520 in order to prevent outer moisture from penetrating into the OLED D. The encapsulation film may have, but is not limited to, a laminated structure of a first inorganic insulating film, an organic insulating film and a second inorganic insulating film (see, 170 in FIG. 2).

In addition, the organic light emitting display device 600 may further include a polarizing plate to reduce reflection of external light. For example, the polarizing plate may be a circular polarizing plate. When the organic light emitting display device 600 is a bottom-emission type, the polarizing plate may be disposed under the first substrate 602. Alternatively, when the organic light emitting display device 600 is a top-emission type, the polarizing plate may be disposed over the encapsulation film, for example, over the second substrate 604.

In FIG. 5, the light emitted from the OLED D is transmitted through the second electrode 720 and the color filter layer 680 is disposed over the OLED D. Alternatively, the light emitted from the OLED D is transmitted through the first electrode 710 and the color filter layer 680 may be disposed between the OLED D and the first substrate 602. In addition, a color conversion layer may be formed between the OLED D and the color filter layer 680. The color conversion layer may include a red color conversion layer, a green color conversion layer and a blue color conversion layer each of which is disposed correspondingly to each pixel region (RP, GP and BP), respectively, so as to covert the white (W) color light to each of a red, green and blue color lights, respectively. Alternatively, the organic light emitting display device 600 may comprise the color conversion film instead of the color filter layer 680.

As described above, the white (W) color light emitted from the OLED D is transmitted through the red color filter 682, the green color filter 684 and the blue color filter 686 each of which is disposed correspondingly to the red pixel region RP, the green pixel region GP and the blue pixel region BP, respectively, so that red, green and blue color lights are displayed in the red pixel region RP, the green pixel region GP and the blue pixel region BP.

Now, we will explain an OLED that can be applied into the organic light emitting display device 600 in detail. FIG. 6 is a schematic cross-sectional view illustrating an OLED in accordance with another exemplary aspect of the present disclosure. As illustrated in FIG. 6, the OLED D3 includes first and second electrodes 710 and 720 facing each other and an emissive layer 730 disposed between the first and second electrodes 710 and 720.

One of the first and second electrodes 710 and 720 is an anode and the other of the first and second electrodes 710 and 720 is a cathode. As an example, the first electrode 710 may be a cathode injecting holes and the second electrode 720 may be a cathode injecting electrons. In addition, one of the first and second electrodes 710 and 720 is a reflective electrode and the other of the first and second electrodes 710 and 720 is a transmissive (semi-transmissive) electrode.

The emissive layer 730 includes a first emitting part 800, a second emitting part 900 and a third emitting part 1000. The emissive layer 730 further includes a first charge generation layer (CGL1) 870 disposed between the first emitting part 800 and the second emitting part 900 and a second charge generation layer (CGL2) 970 disposed between the second emitting part 900 and the third emitting part 1000. Accordingly, the first emitting part 800, the CGL1 870, the second emitting part 900, the CGL2 970 and the third emitting part 1000 are sequentially formed over the first electrode 710. In other words, the first emitting part 800 is disposed between the first electrode 710 and the CGL1 870, the second emitting part 900 is disposed between the CGL1 870 and the CGL2 970 and the third emitting part 1000 is disposed between the second electrode 720 and the CGL2 970.

The first emitting part 800 includes a first EML (lower EML, EML1) 840. The first emitting part 800 may further includes at least one of an HIL 810 disposed between the first electrode 710 and the EML1 840, a first HTL (lower HTL, HTL1) 820 disposed between the HIL 810 and the EML1 840 and a first ETL (lower ETL, ETL1) 850 disposed between the EML1 840 and the CGL1 870. In addition, the first emitting part 800 may further include a first EBL (lower EBL, EBL1) 830 disposed between the HTL1 820 and the EML1 840.

The second emitting part 900 includes a second EML (middle EML, EML2) 940. The second emitting part 900 may further include at least one of a second HTL (middle HTL, HTL2) 920 disposed between the CGL1 870 and the EML2 940 and a second ETL (middle ETL, ETL2) 950 disposed between the EML2 940 and the CGL2 970.

The third emitting part 1000 includes a third EML (upper EML, EML3) 1040. The third emitting part 1000 may further include a third HTL (upper HTL, HTL3) 1020 disposed between the CGL2 970 and the EML3 1040, a third ETL (upper ETL, ETL3) 1050 disposed between the second electrode 720 and the EML3 1040 and an EIL 1060 disposed between the second electrode 720 and the ETL3 1050. In addition, the third emitting part 1000 may further include a second EBL (upper EBL, EBL2) 1030 disposed between the HTL3 1020 and the EML3 1040.

The HIL 810, the HTL1 820, the HTL2 920, the HTL3 1020 and the EIL 1060 may have substantially the same structure and components as described above.

In one exemplary aspect, each of the EML1 840 and the EML3 1040 may emit blue light, respectively. The EML1 840 may include a first host and a first dopant and the EML3 840 may include a second host and a second dopant. In one exemplary aspect, each of the first host and the second host may comprise independently the anthracene-based organic compound having the structure of Formulae 5 to 6 and each of the first dopant and the second dopant may comprise independently the boron-based organic compound having the structure of Formulae 7 to 8. The first host may be identical to or different from the second host and the first dopant may be identical to or different from the second dopant. The contents of the first dopant and the second dopant in each of the EML1 840 and the EML2 1040 may be, but is not limited to, about 1 wt % to about 10 wt %, for example, about 1 wt % to about 5 wt %.

The EBL1 830 prevents electrons from transporting to the first electrode 710 through the EML1 840 and the EBL2 1030 prevent electrons from transporting to the CGL2 870 through the EML3 1040. In one exemplary aspect, each of the EBL1 830 and the EBL2 1030 may be selected from independently, but is not limited to, the following spirofluorene-based organic compound having the structure of Formula 9:

[Formula 9]

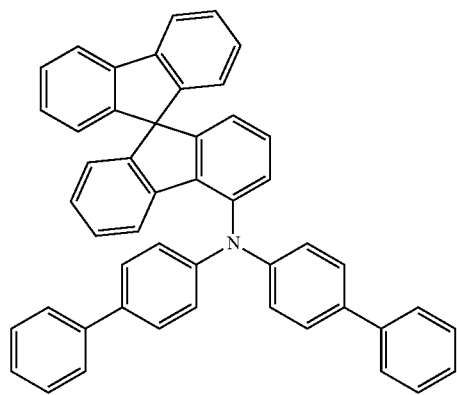

K1

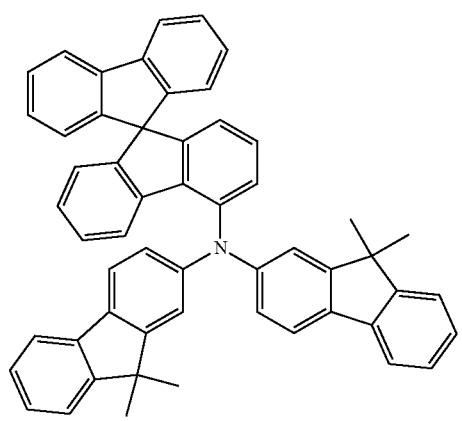

K2

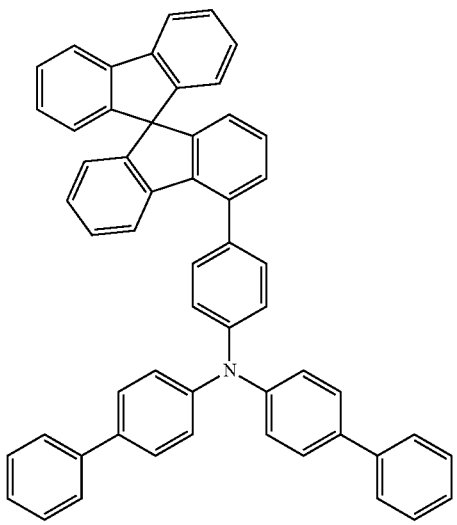

K3

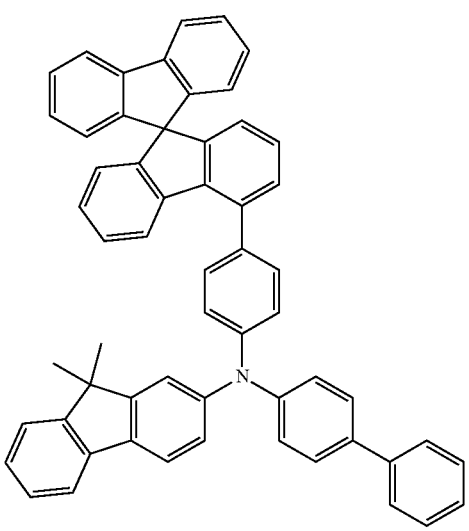

K4

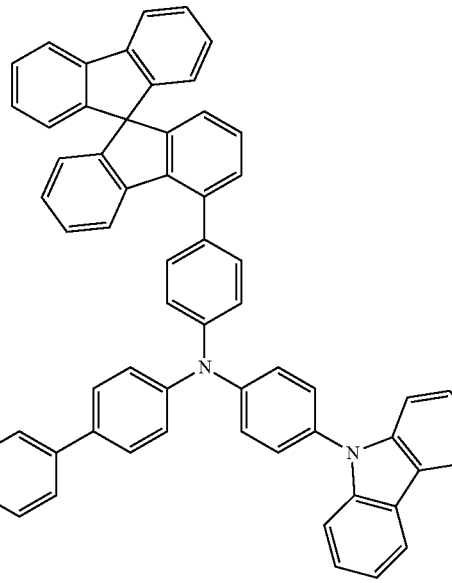

K5

K6
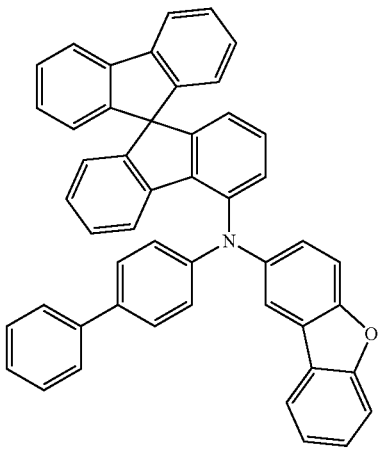

K7
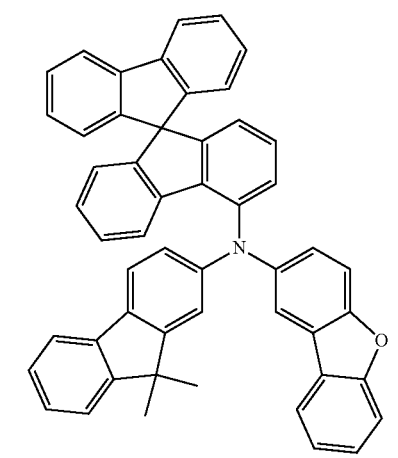

K8
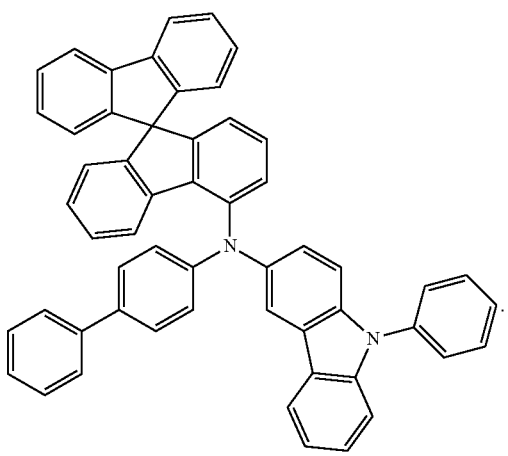

In one exemplary aspect, each of the ETL1 850, the ETL2 950 and the ETL3 1050 may include independently, but is not limited to, at least one of oxadiazole-based compounds, triazole-based compounds, phenanthroline-based compounds, benzoxazole-based compounds, benzothiazole-based compounds, benzimidazole-based compounds, triazine-based compounds, and the like.

As an example, each of the ETL1 850, the ETL2 950 and the ETL3 1050 may include, but is not limited to, Alq$_3$, BAlq, Liq, PBD, spiro-PBD, TPBi, Bphen, NBphen, BCP, TAZ, NTAZ, TpPyPB, TmPPPyTz, PFNBr, TPQ, TSPO1, (ZADN and combination thereof Alternatively, each of the ETL1 850, the ETL2 950 and the ETL3 1050 may include a first electron transport material 852, a second electron transport material 952 and a third electron transport material 1052, respectively, each of which is independently the organic compound having the structure of Formulae 1 to 4.

In still another alternative aspect, each of the ETL1 850, the ETL2 950 and the ETL3 1050 may further include independently the alkali metal and/or the alkaline earth metal doped to each of the first to third electron transport materials 852, 952 and 1052. The contents of the alkali metal and/or the alkaline earth metal in each of the ETL1 850 to the ETL3 1050 may be, but is not limited to, about 1 wt % to about 10 wt %, for example, about 1 wt % to about 5 wt %.

The CGL1 870 is disposed between the first emitting part 800 and the second emitting part 900. The CGL1 870 includes a first N-type CGL (N-CGL1) 880 disposed between the ETL1 850 and the HTL2 920 and a first P-type CGL (P-CGL1) 890 disposed between the N-CGL1 880 and the HTL2 920. The N-CGL1 880 transports electrons to the EML1 840 of the first emitting part 800 and the P-CGL1 890 transport holes to the EML2 940 of the second emitting part 900.

The CGL2 970 is disposed between the second emitting part 900 and the third emitting part 1000. The CGL2 970 includes a second N-type CGL (N-CGL2) 980 disposed between the ETL2 950 and the HTL3 1020 and a second P-type CGL (P-CGL2) 990 disposed between the N-CGL1 980 and the HTL3 1020. The N-CGL1 980 transports electrons to the EML2 940 of the second emitting part 900 and the P-CGL2 990 transport holes to the EML3 1040 of the third emitting part 1000.

Each of the N-CGL1 880 and the N-CGL2 980 may be an organic layer including an N-type host, and optionally an N-type dopant, respectively. For example, each of the N-CGL 1 880 and the N-CGL2 980 may include a first N-type charge generation material 882 and a second N-type charge generation material 982, respectively, each of which may be independently the organic compound having the structure of Formulae 1 to 4, as the N-type host. The N-type dopant may include an alkali metal such as Li, Na, K and Cs and/or an alkaline earth metal such as Mg, Sr, Ba and Ra. In this case, the N-type dopant binds to the N-type host in order to form a gap state. Accordingly, as energy level bandgap between the N-CGL1 880 or the N-CGL2 980 and the P-CGL1 890 or the P-CGL2 990 becomes small, electron injection property from the N-CGL1 880 and the N-CGL2 980 to the ETL1 850 and the ETL2 950 may be improved. For example, the contents of the N-type dopant in each of the N-CGL1 880 and the N-CGL2 980 may be, but is not limited to, about 1 wt % to about 10 wt %, for example, about 1 wt % to about 5 wt %.

The P-type CGL 490 may be an organic layer including a P-type host, and optionally a P-type dopant. The kinds and contents of the P-type host and the P-type dopant may be substantially identical to the P-type host and the P-type dopant as described in the P-type dopant 490.

The EML2 940 may include a lower middle EML (first layer) 940A and an upper milled EML (second layer) 940B. The lower middle EML 940A is located adjacently to the HTL2 920 and the upper middle EML 940B is located adjacently to the ETL2 950. One of the lower middle EML 940A and the upper middle EML 940B may be a green EML and the other of the lower middle EML 940A and the upper middle EML 940B may be a red EML. In other words, a red EML and a green EML is sequentially laminated to form the EML2 940.

For example, the lower middle EML 940A may be the red EML. In this case, the lower middle EML 940A may include red host (third host) and red dopant (third dopant). In one exemplary aspect, the third host may include a P-type red host (hole-type red host) and an N-type red host (electron-type red host).

As an example, the P-type red host may be selected from, but is not limited to, the following spirofluorene-based organic compounds having the structure of Formula 10, and the N-type red host may be selected from, but is not limited to, the following quinazoline-carbazole-based organic compounds having the structure of Formula 11:

[Formula 10]

E1

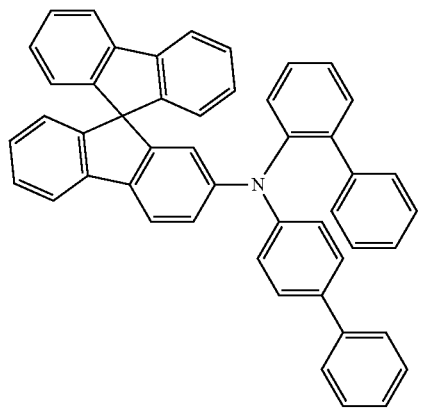

-continued

E3

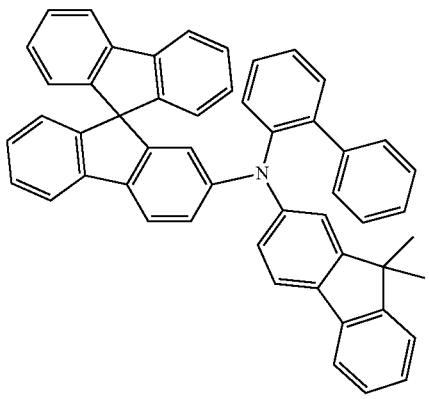

E4

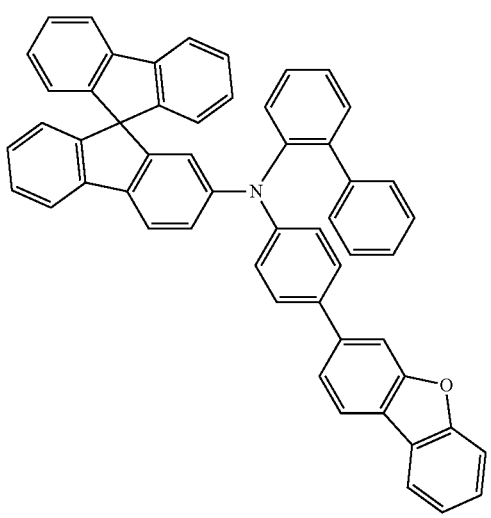

E2

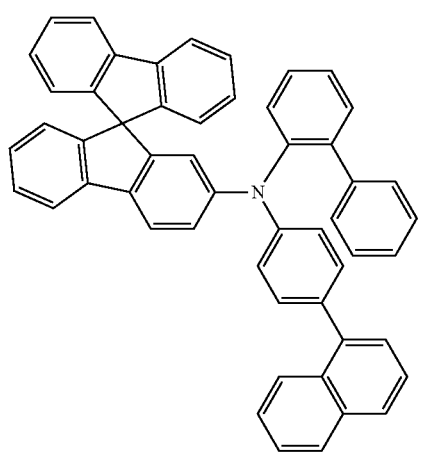

E5

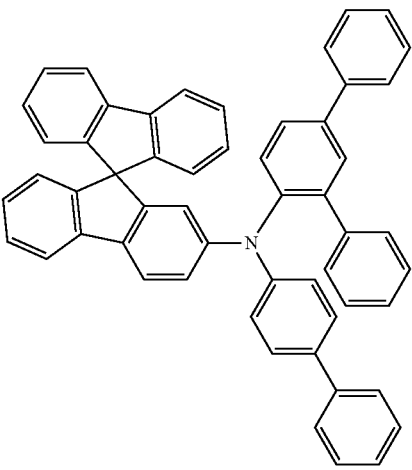

-continued
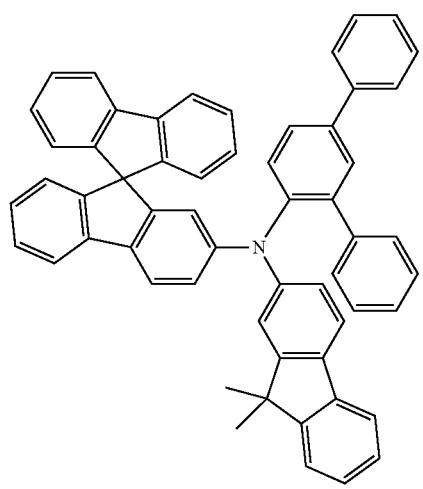
E6
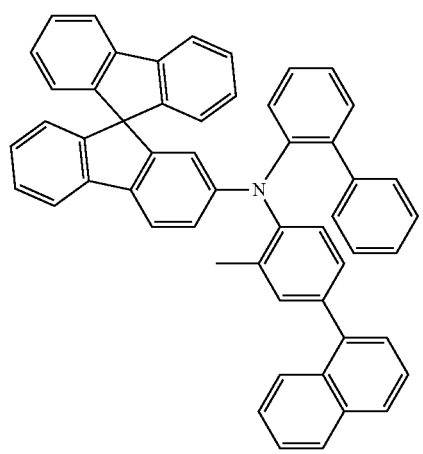
E7
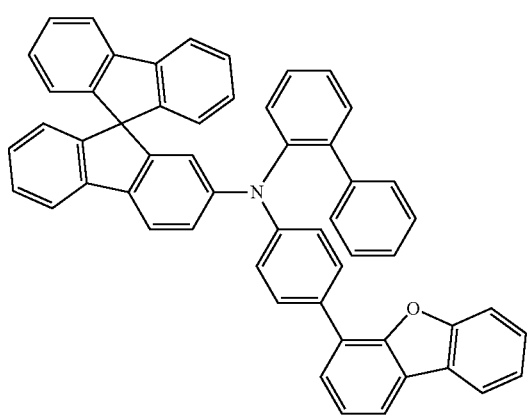
E8
-continued
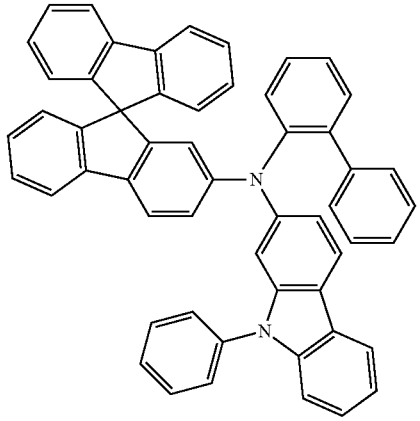
E9
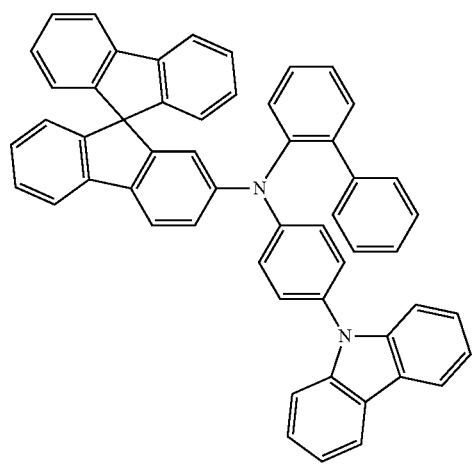
E10
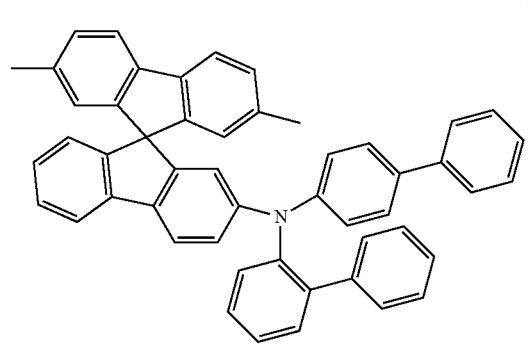
E11

E12
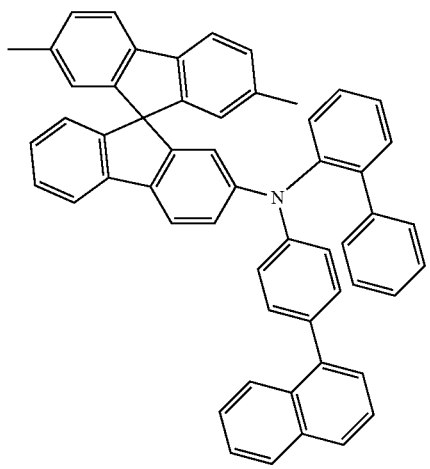
E13
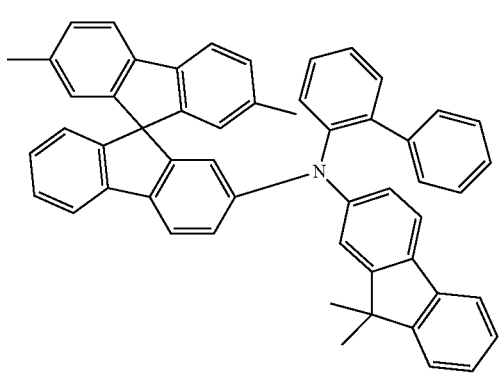
E14
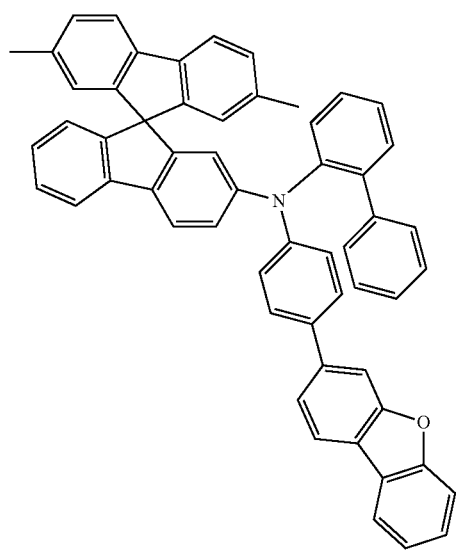
E15
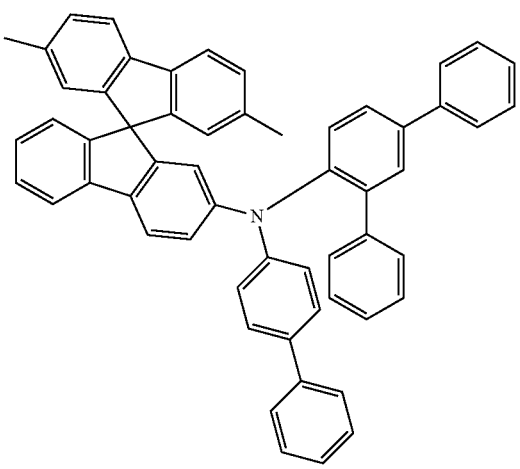
E16
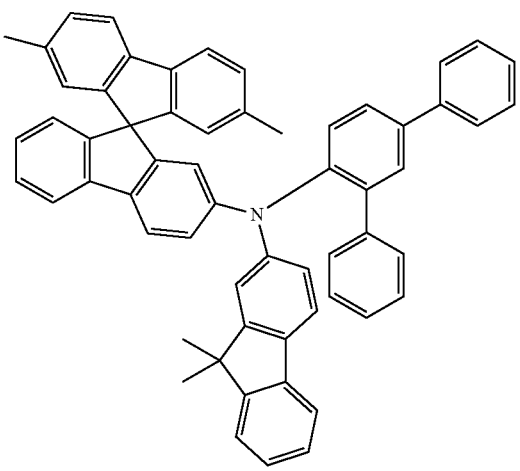
E17
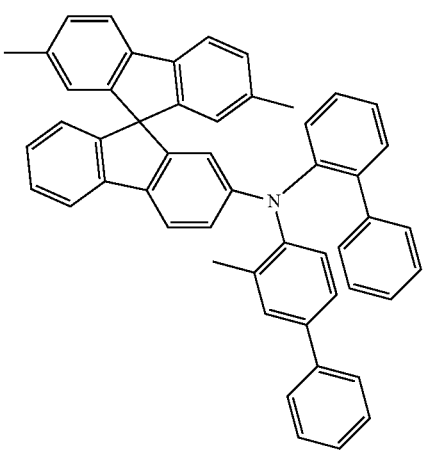

E18
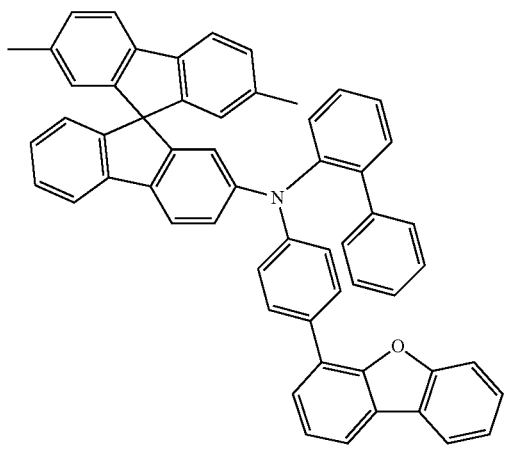
[Formula 11]
L1
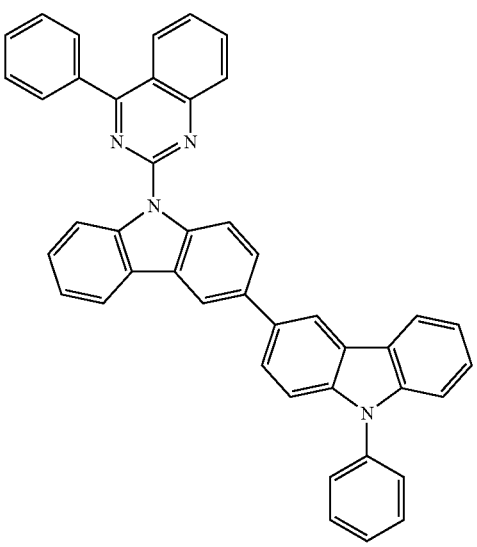
E19
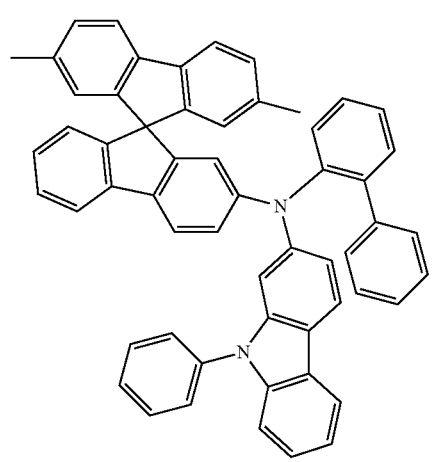
L2
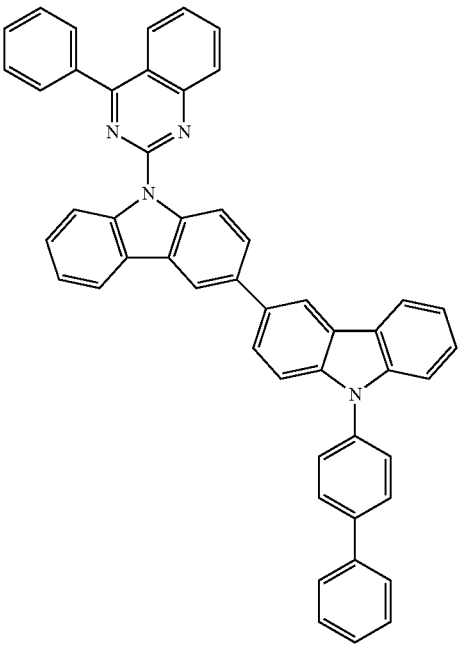
E20
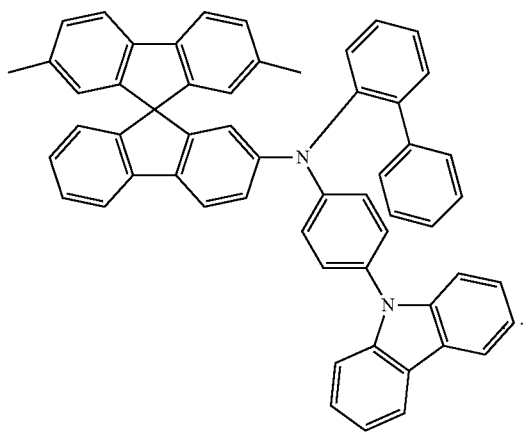

L3
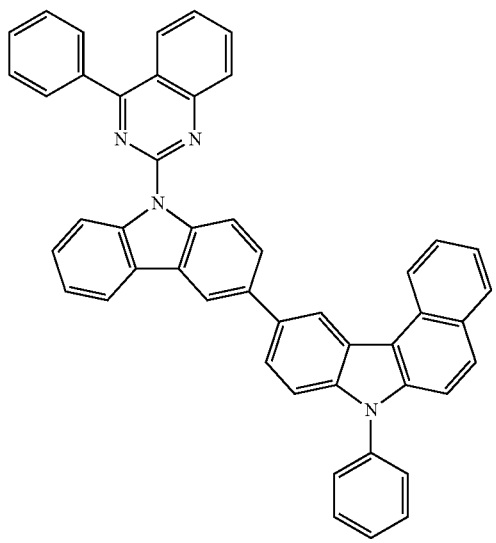
L4
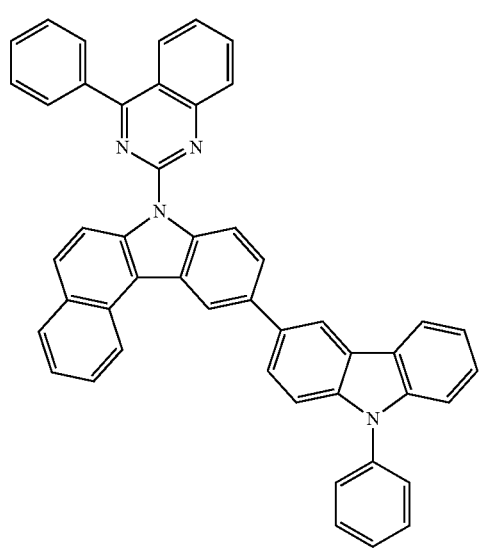
L5
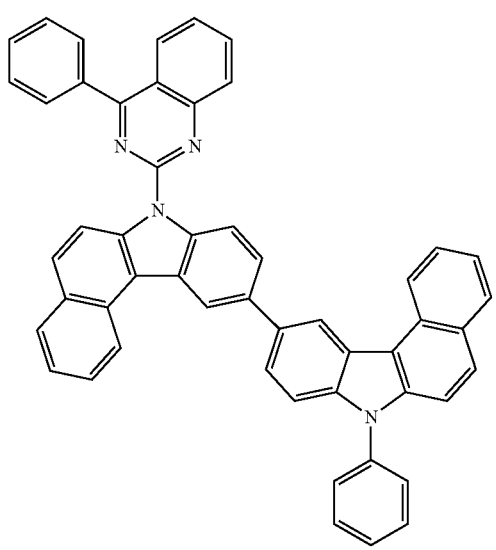
L6
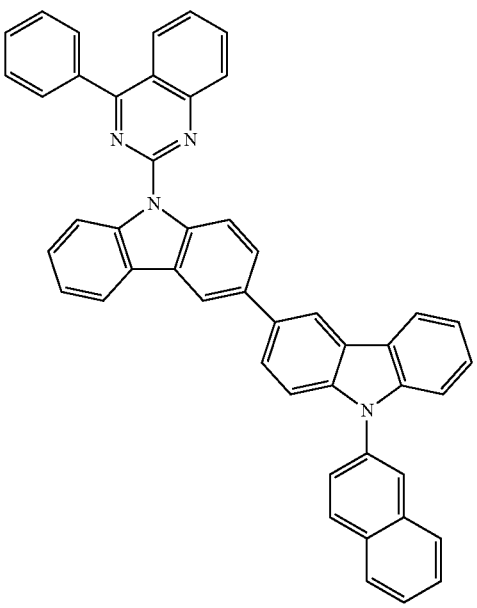
L7
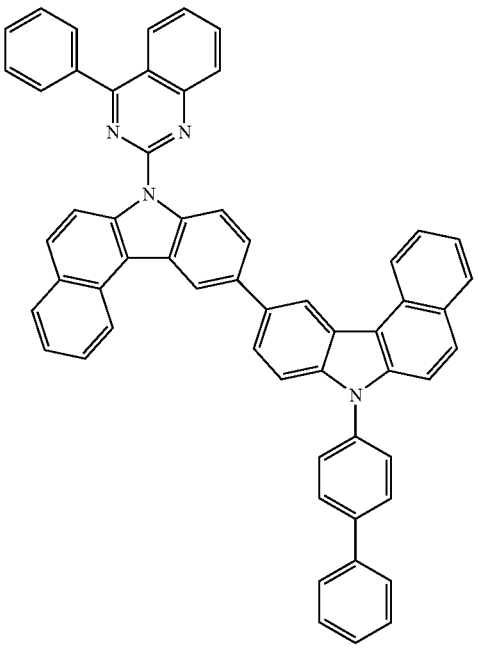

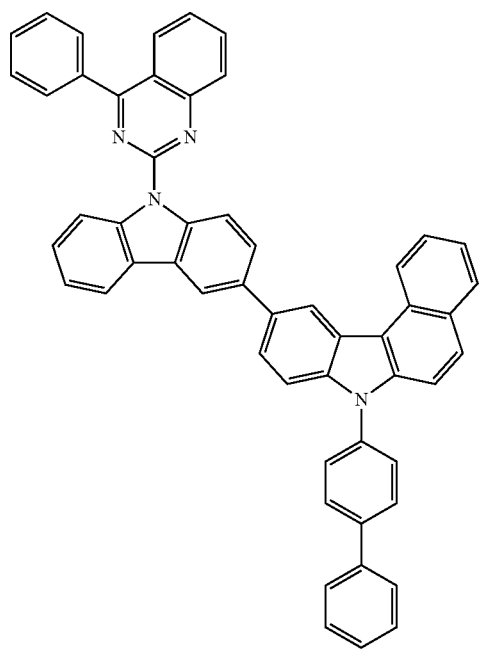

L8

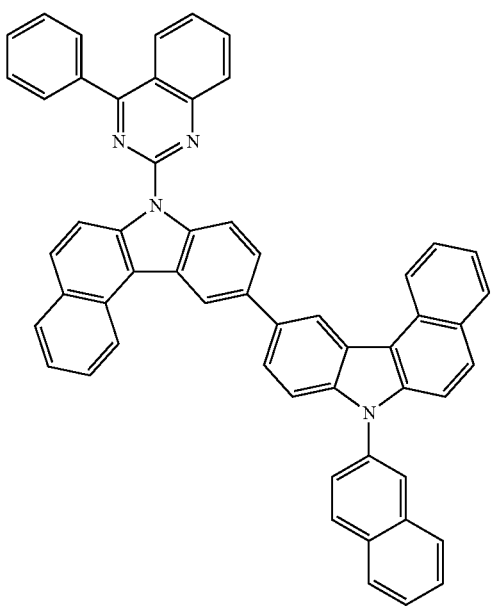

L9

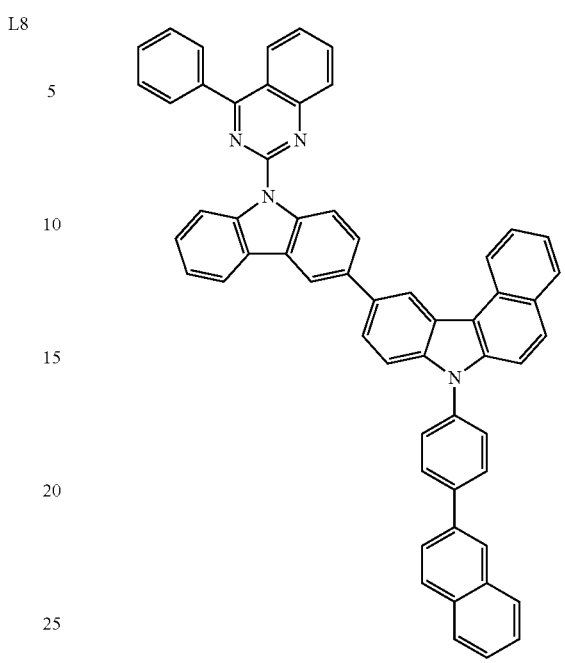

L10

L11

In one exemplary aspect, the P-type red host and the N-type red host in the lower middle EML 940A may be admixed with a weight ratio, but is not limited to, about 1:9 to about 9:1, for example, about 2:8 to about 8:2 or about 7:3 to about 3:7.

The red dopant (third dopant) may include at least one of red phosphorescent material, red fluorescent material and red delayed fluorescent material. In one exemplary aspect, the red phosphorescent material may be selected from, but is not limited to, the following phosphorescent materials having the structure of Formula 12:

[Formula 12]

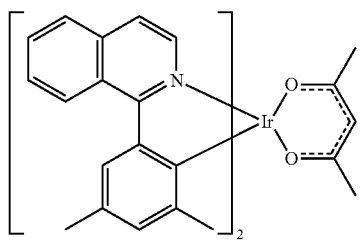
M1

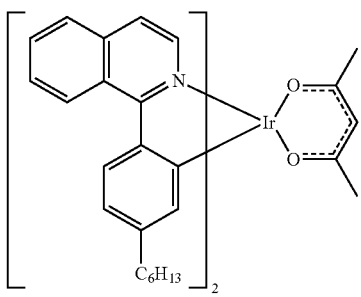
M2

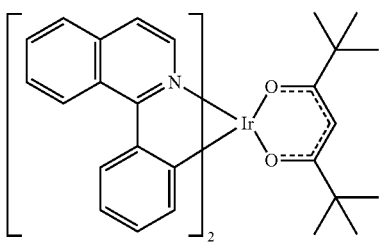
M3

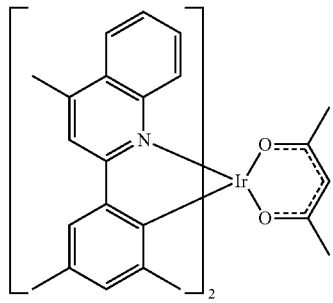
M4

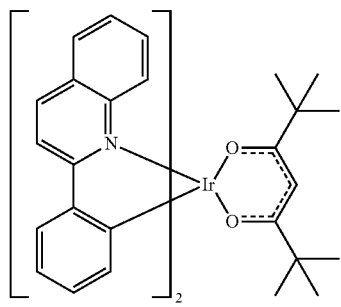
M5

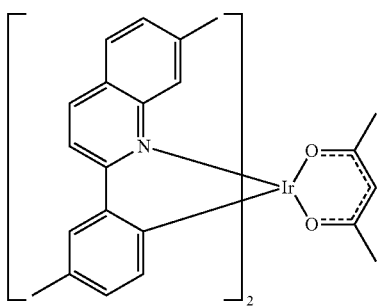
M6

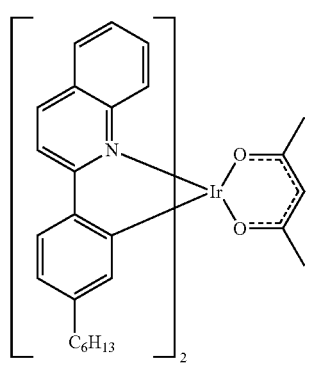
M7

The contents of the red dopant in the lower middle EML 940A may be, but is not limited to, about 1 wt % to about 10 wt %, for example, about 1 wt % to about 5 wt %.

The upper middle EML 940B may be the green EML. In this case, the upper middle EML 940B may include green host (fourth host) and green dopant (fourth dopant). In one exemplary aspect, the fourth host may include a P-type green host (hole-type green host) and an N-type green host (electron-type green host).

As an example, the P-type green host may be selected from, but is not limited to, the following biscarbazole-based organic compounds having the structure of Formula 13, and the N-type green host may be selected from, but is not limited to, the following triazine-based organic compounds having the structure of Formula 14:

[Formula 13]

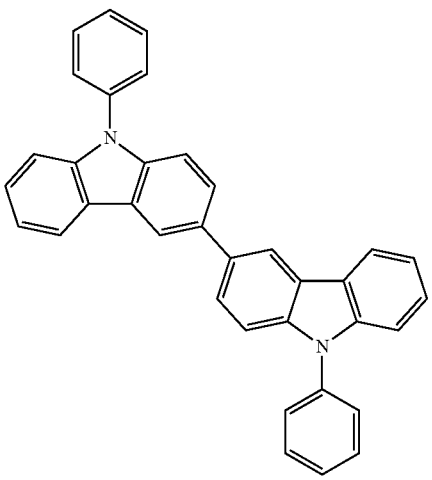
P1

-continued
P2
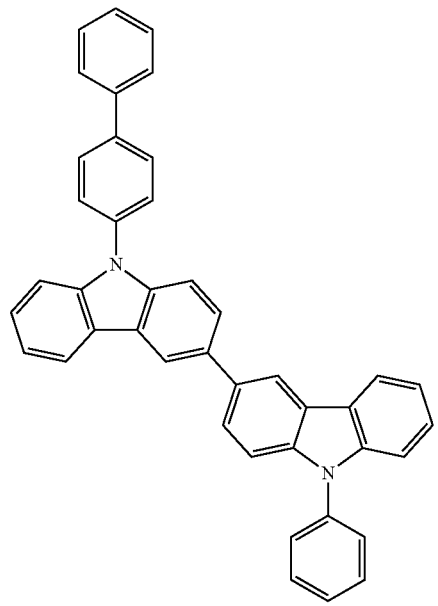
P3
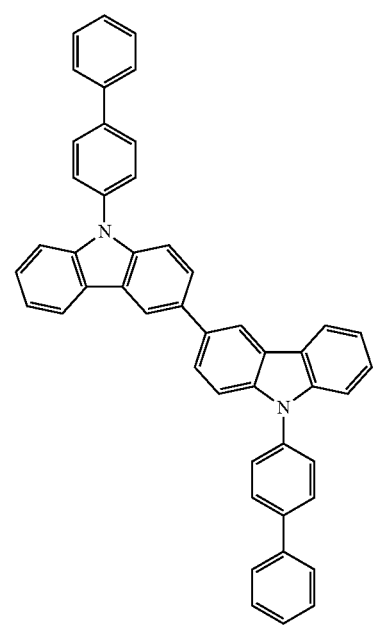
-continued
P4
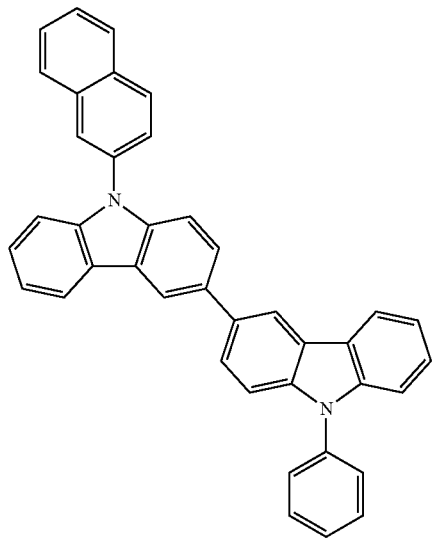
P5
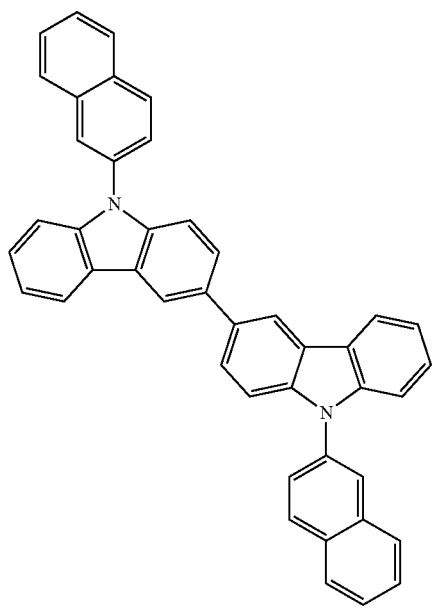

P6
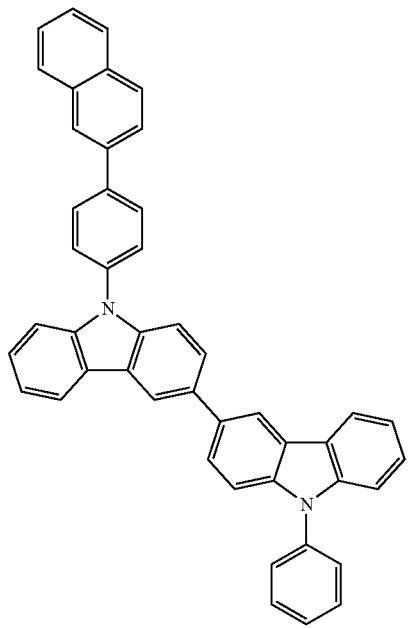
P7
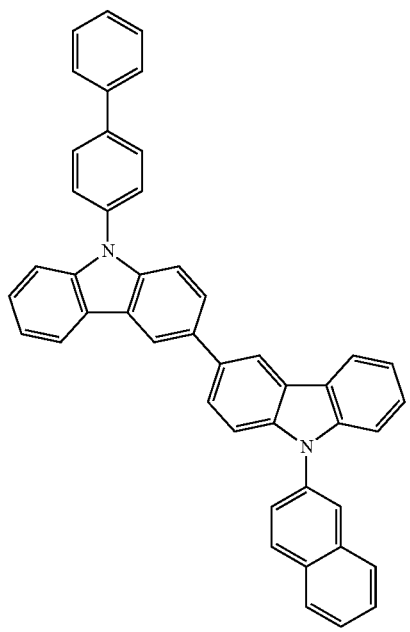
P8
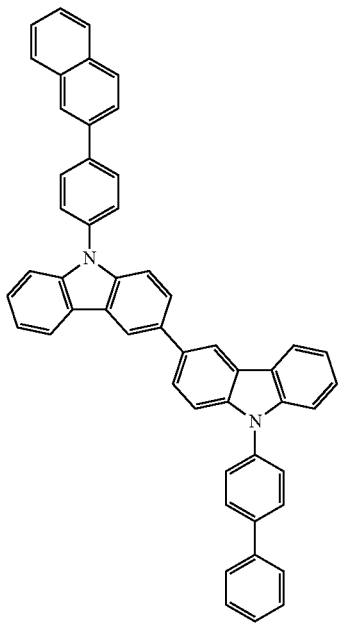
P9
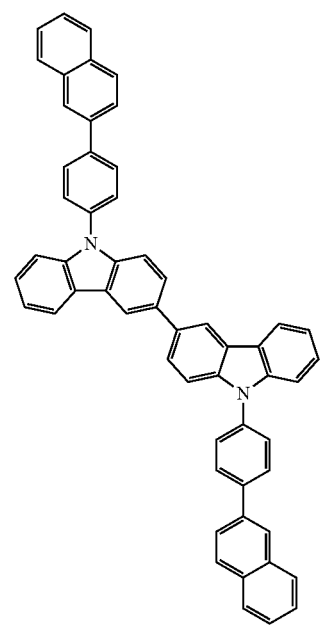
[Formula 14]
Q1
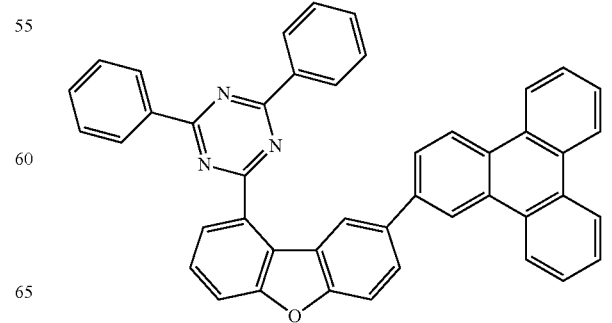

Q2
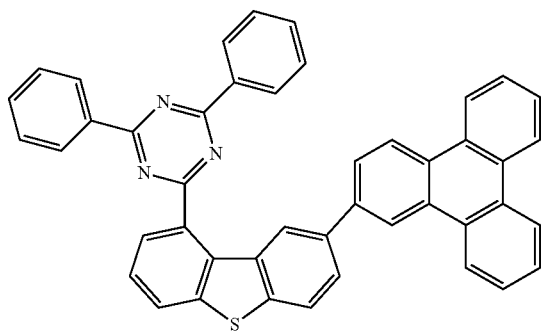
Q3
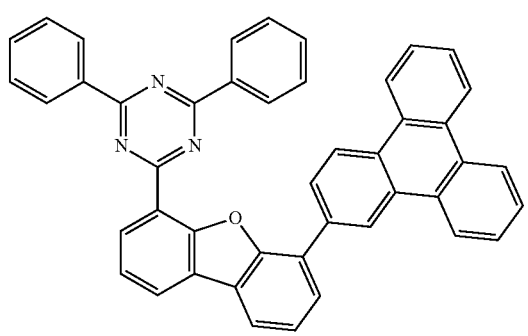
Q4
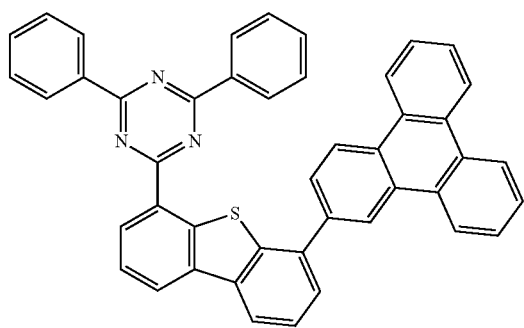
Q5
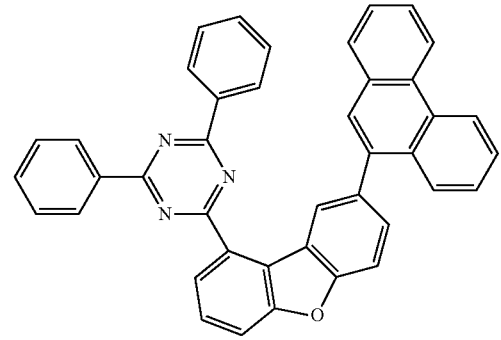
Q6
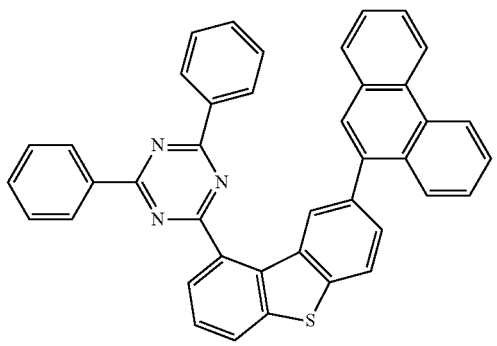
Q7
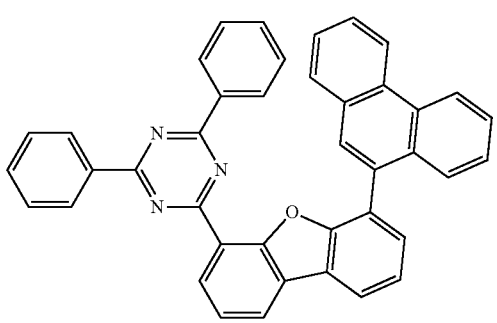
Q8
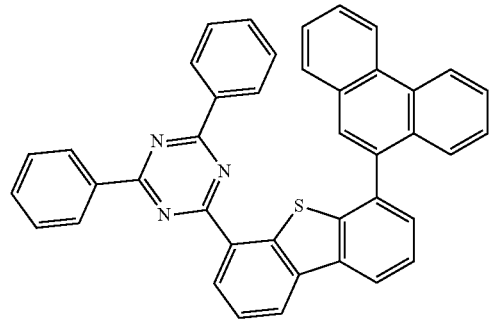
Q9
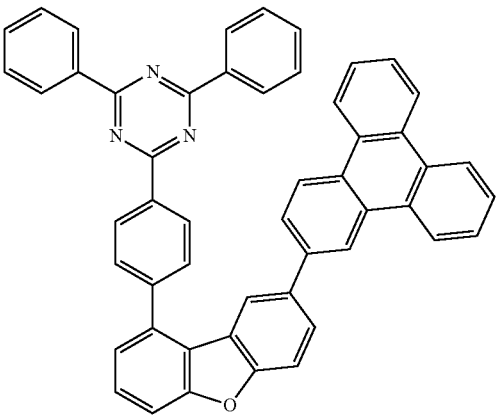

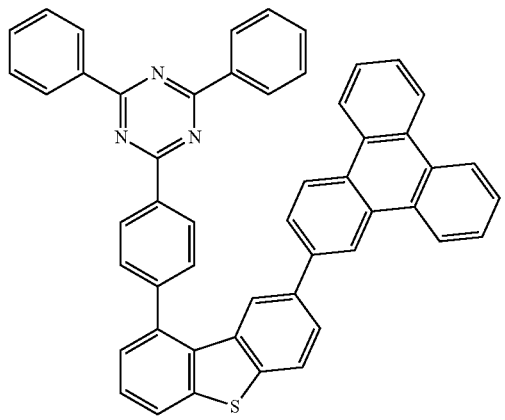
Q10
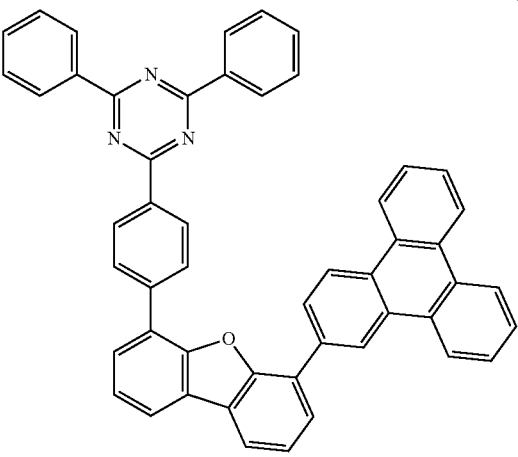
Q13
Q11
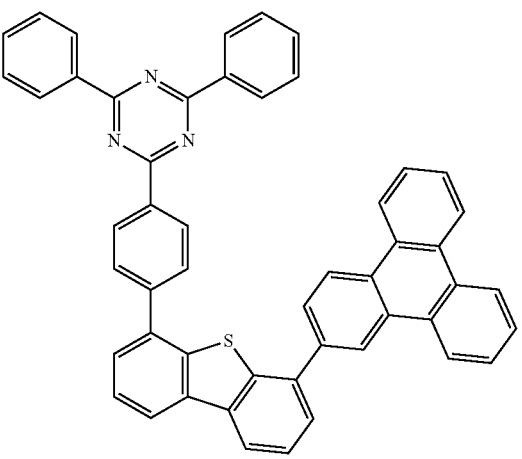
Q14
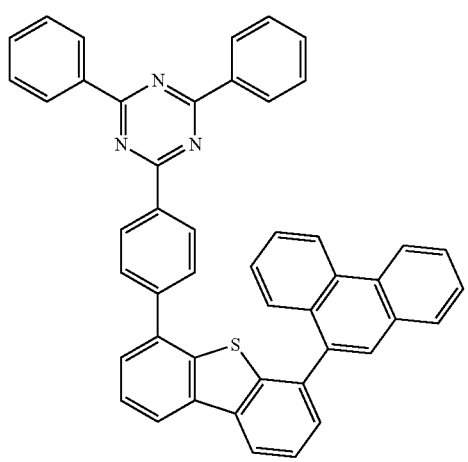
Q12
Q15

Q16

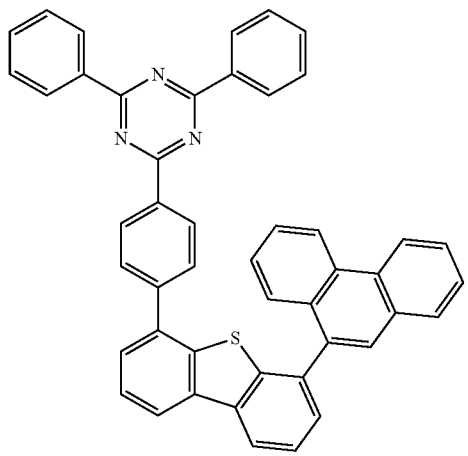

In one exemplary aspect, the P-type green host and the N-type green host in the upper middle EML 940B may be admixed with a weight ratio, but is not limited to, about 1:9 to about 9:1, for example, about 2:8 to about 8:2 or about 7:3 to about 3:7.

The green dopant (fourth dopant) may include at least one of green phosphorescent material, green fluorescent material and green delayed fluorescent material. In one exemplary aspect, the green phosphorescent material may be selected from, but is not limited to, the following phosphorescent materials having the structure of Formula 15:

[Formula 15]

S1

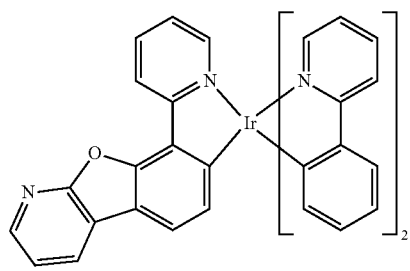

S2

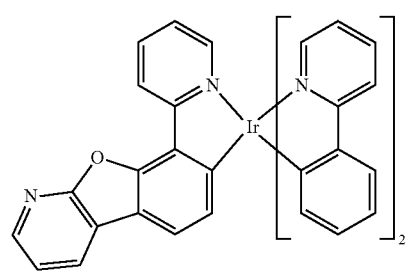

S3

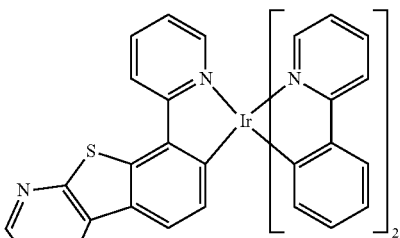

S4

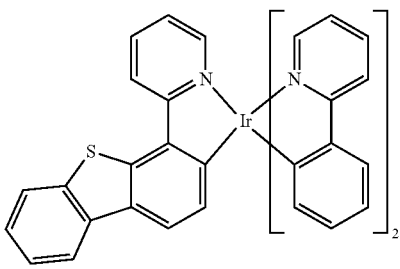

The contents of the green dopant in the upper middle EML 940B may be, but is not limited to, about 1 wt % to about 10 wt %, for example, about 1 wt % to about 5 wt %.

In this aspect, each of the ETL1 850, the ETL2 950, the ETL3 1050, the N-CGL1 880 and the N-CGL2 980 includes the first electron transport material 852, the second electron transport material 952, the third electron transport material 1050, the first N-type charge generation material 882, and the second N-type charge generation material 982, respectively, at least one of which may be the organic compound having the structure of Formulae 1 to 4. Accordingly, the OLED D3 can lower its driving voltage and improve its luminous property.

In FIG. 6, the OLED D3 has a tandem structure with three emitting parts. The OLED may further include additional emitting part and charge generation layer. Alternatively, one of the first and third emitting parts 800 and 1000 each of which includes the EML1 840 and the EML3 1040, respectively, is omitted so that the OLED D3 has a double-stack structure.

Figure 7:
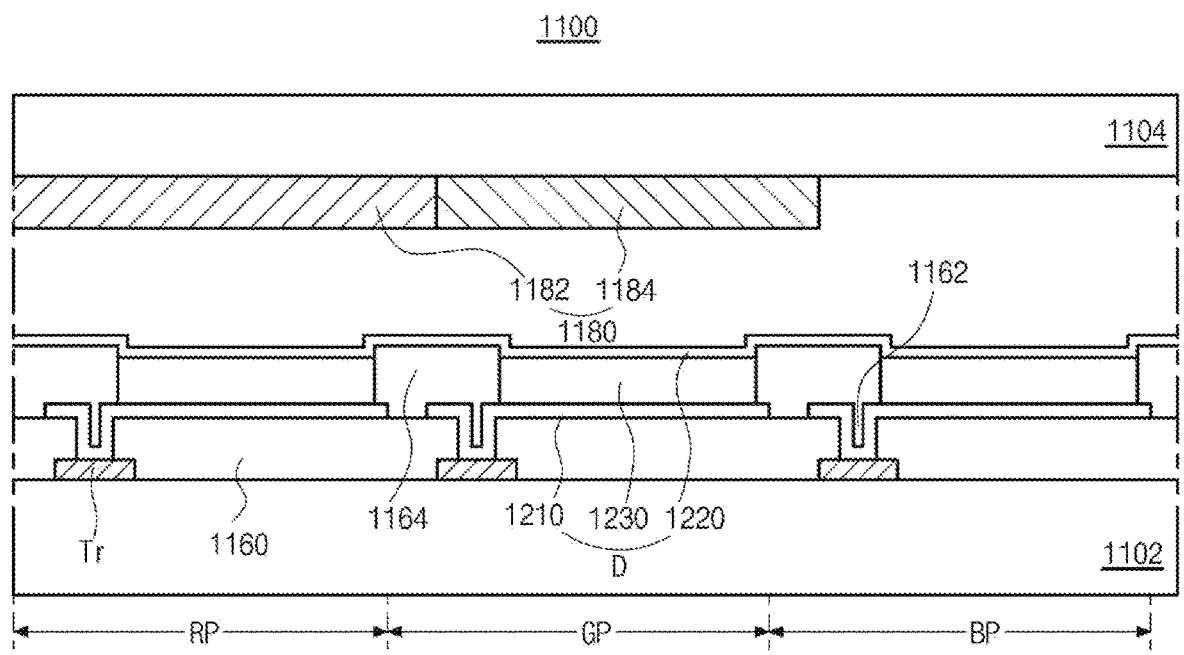
FIG. 7 is a schematic cross-sectional view illustrating an organic light emitting display device as an example of an organic light emitting device in accordance with still another exemplary aspect of the present disclosure.

In addition, an organic light emitting device in accordance with the present disclosure may include a color conversion layer. FIG. 7 is a schematic cross-sectional view illustrating an organic light emitting display device in still another exemplary aspect of the present disclosure.

As illustrated in FIG. 7, the organic light emitting display device 1100 comprises a first substrate 1102 that defines each of a red pixel region RP, a green pixel region GP and a blue pixel region BP, a second substrate 1104 facing the first substrate 1102, a thin film transistor Tr over the first substrate 1102, an organic light emitting diode (OLED) D disposed between the first and second substrates 1102 and 1104 and emitting blue (B) light and a color conversion layer 1180 disposed between the OLED D and the second substrate 1104. Although not shown in FIG. 7, a color filter layer may be disposed between the second substrate 1104 and the respective color conversion layer 1180.

The thin film transistor Tr is disposed over the first substrate 1102 correspondingly to each of the red pixel region RP, the green pixel region GP and the blue pixel region BP. A passivation layer 1160, which has a drain contact hole 1162 exposing one electrode, for example a drain electrode, constituting the thin film transistor Tr, is formed with covering the thin film transistor Tr over the whole first substrate 1102.

The OLED D, which includes a first electrode 1210, an emissive layer 1230 and the second electrode 1220, is disposed over the passivation layer 1160. The first electrode 1110 may be connected to the drain electrode of the thin film transistor Tr through the drain contact hole 1162. In addition, a bank layer 1164 covering edges of the first electrode 1210 is formed at the boundary between the red pixel region RP, the green pixel region GP and the blue pixel region BP. In this case, the OLED D may have a structure of FIG. 3 or FIG. 4 and can emit blue (B) light. The OLED D is disposed in each of the red pixel region RP, the green pixel region GP and the blue pixel region BP to provide blue (B) light.

The color conversion layer 1180 may include a first color conversion layer 1182 corresponding to the red pixel region RP and a second color conversion layer 1184 corresponding to the green pixel region GP. As an example, the color conversion layer 1180 may include an inorganic luminescent material such as quantum dot (QD).

The blue (B) light emitted from the OLED D in the red pixel region RP is converted into red (R) color light by the first color conversion layer 1182 and the blue (B) light emitted from the OLED D in the green pixel region GP is converted into green (G) color light by the second color conversion layer 1184. Accordingly, the organic light emitting display device 1100 can implement a color image.

In addition, when the light emitted from the OLED D is displayed through the first substrate 1102, the color conversion layer 1180 may be disposed between the OLED D and the first substrate 1102.

Synthesis Example 1: Synthesis of Compound D1

(1) Synthesis of Intermediate A

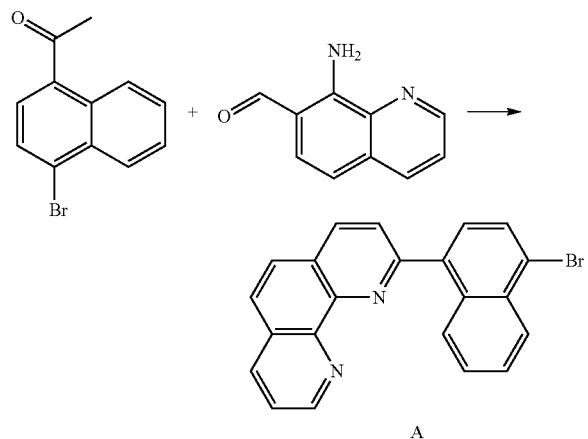

1-bromo-4-acetylnaphthalene (14.5 g, 0.058 mmol), 8-aminoquinoline-7-carb aldehyde (10 g, 0.058 mmol), absolute ethanol (800 ml) and KOH (13 g, 0.232 mol) were put into a round bottom flask, and then the solution was refluxed for 15 hours. After the reactants were cooled to a room temperature (RT), the reactants were extracted with $CH_2Cl_2/H_2O$ ($CH_2Cl_2$, 150 ml) three times to recover an organic layer. The organic layer was concentrated under reduced pressure, and then recrystallized with ethyl acetate (EtOAc) to give the pure Intermediate A (10.5 g, yield: 47%).

(2) Synthesis of Intermediate B

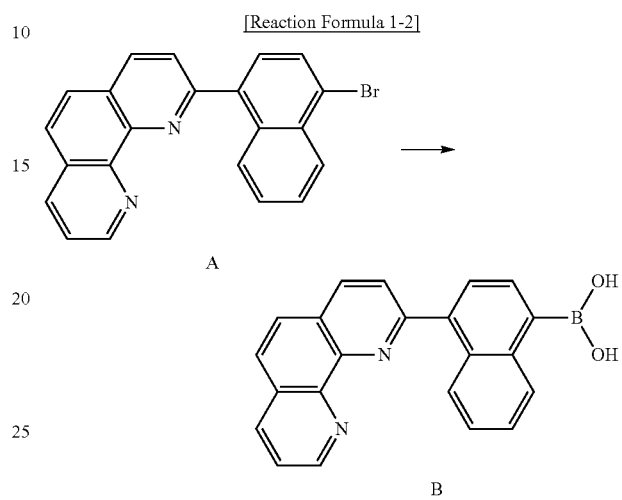

The Intermediate A (10 g, 0.026 mol), bis(pinacolato)diborn (7.9 g, 0.04 mol), [1,1'-bis(diphenylphosphino)ferrocene]dichloropalladium(II) (pd(dppf)Cl$_2$, 1.1 g, 0.2 mol), potassium acetate (KOAc, 9.2 g, 0.09 mol) and 1,4-dioxane (200 ml) were put into a round bottom flask, and then the solution was refluxed for 12 hours. After the reactants were cooled to a room temperature, the reactants were filtered with celite and then washed with CHCl$_3$ (150 ml) five times. The filtrate was concentrated under reduced pressure and recrystallized with EtOAc to give the pure Intermediate B (7.9 g, 0.023 mol, yield: 88%).

(3) Synthesis of Intermediate C

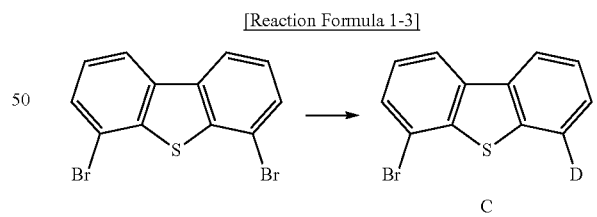

4,6-diboromobenzothiophene (10.0 g, 0.029 mol) dissolved in dry THF (250 ml) was put into a round bottom flask, and then n-BuLi (n-butyllithium, 1.6 M in hexane 20 ml, 0.032 mol) was added slowly into the solution at −78° C. under nitrogen atmosphere, and then the solution was stirred for 30 minutes. D$_2$O (1.0 ml, 0.055 mol) was added into the reaction mixtures, then, the reaction mixture was raised to RT, and was stirred again for 1 hour. The reaction mixture was purified with silica column chromatography (eluent: CH$_2$Cl$_2$) and then solvent was removed to give the pure Intermediate C (7.7 g, 0.029 mol, yield: >99%).

(4) Synthesis of Compound D1

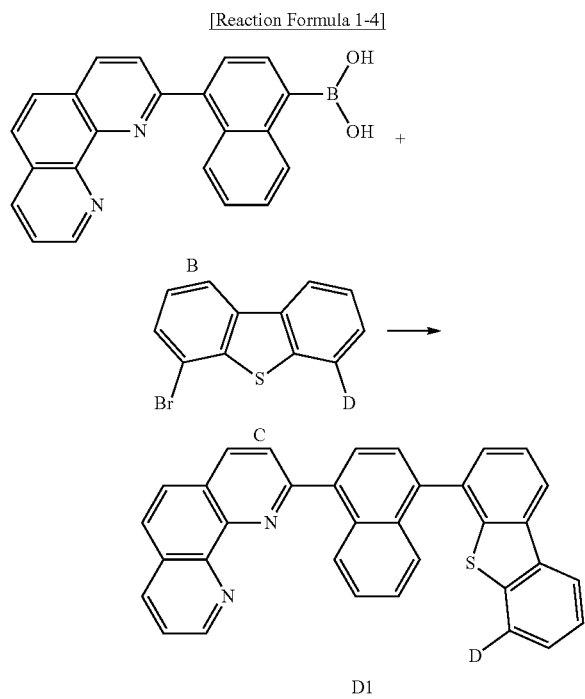

The Intermediate B (7.0 g, 0.02 mol), the Intermediate C (5.32 g, 0.02 mol), Tetrakis(triphenylphosphine)Palladium (0) (Pd(PPh$_3$)$_4$, 0.9 g, 0.1 mmol), K$_2$CO$_3$ (8.3 g, 0.06 mol) dissolved in a mixed solvent of toluene/EtOH (100 ml/40 ml) were put into a round bottom flask, and the solution was refluxed for 12 hours. After the reaction mixture was cooled to RT, and reaction solution was filtered to obtain a crude product. The crude product was dissolved in CH$_2$Cl$_2$, and the solution was died with MgSO$_4$ to remove the solvent. The crude product was purified with silica column chromatography (eluent: CHCl$_3$) to give pure Compound D1 (6.9 g, 0.014 mol, yield: 70%).

Synthesis Example 2: Synthesis of Compound D2

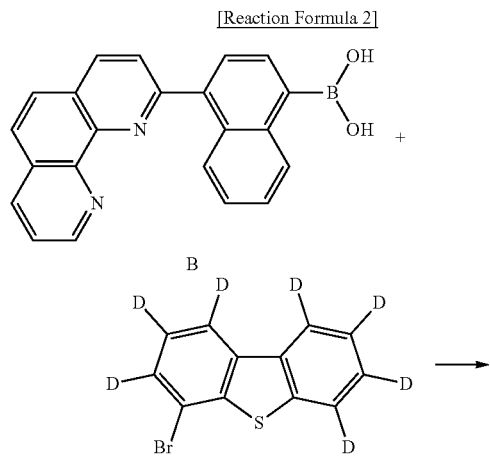

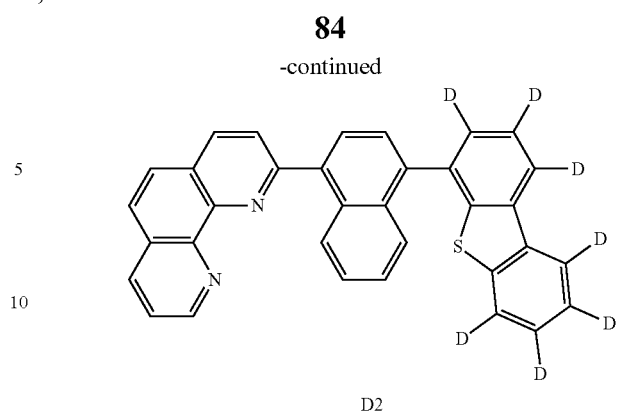

The pure Compound D2 (6.7 g, 0.014 mol, yield: 70%) was obtained by repeating the synthetic process of the Compound D1 except that the Intermediate B (7.0 g, 0.02 mol) and 4-bromodibenzothiophene-d7 (5.4 g, 0.02 mol) were used as the reactants.

Synthesis Example 3: Synthesis of Compound D6

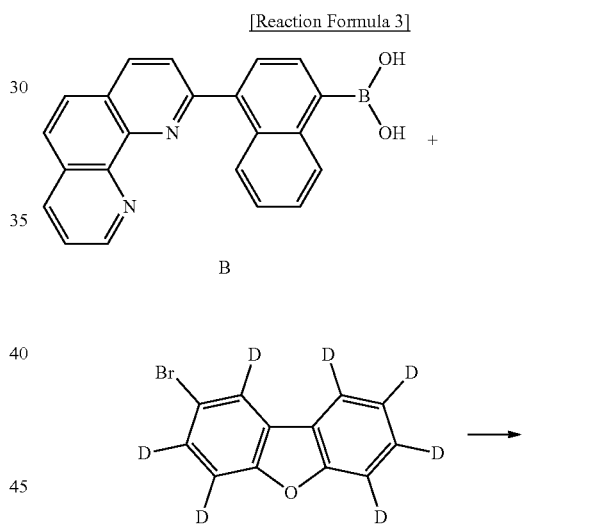

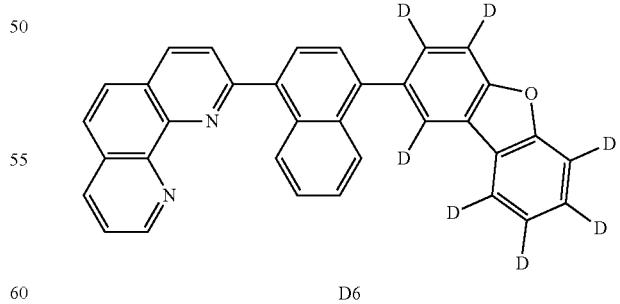

The pure Compound D6 (6.3 g, 0.013 mol, yield: 81%) was obtained by repeating the synthetic process of the Compound D1 except that the Intermediate B (5.7 g, 0.016 mol) and 2-bromodibenzothiophene-d7 (4.5 g, 0.017 mol) were used as the reactants.

Synthesis Example 4: Synthesis of Compound D7

(1) Synthesis of Intermediate D

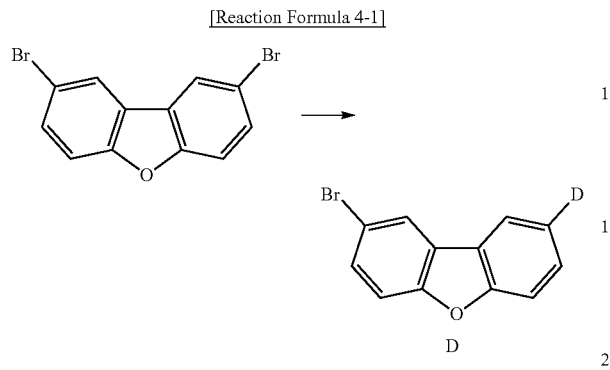

2,8-dibromodibenzofuran (10.0 g, 0.031 mol) dissolved in dry THF (250 ml) was put into a round bottom flask, n-BuLi (1.6 M in hexane 20 ml, 0.032 mol) was added slowly into the solution at −78° C. under nitrogen atmosphere, and then the solution was stirred for 30 minutes. $D_2O$ (1.0 ml, 0.055 mol) was added into the reaction mixtures, then, the reaction mixture was raised to RT, and was stirred again for 1 hour. The reaction mixture was purified with silica column chromatography (eluent: $CH_2Cl_2$) and then solvent was removed to give the pure Intermediate D (7.5 g, 0.30 mol, yield: 97%).

(2) Synthesis of Compound D7

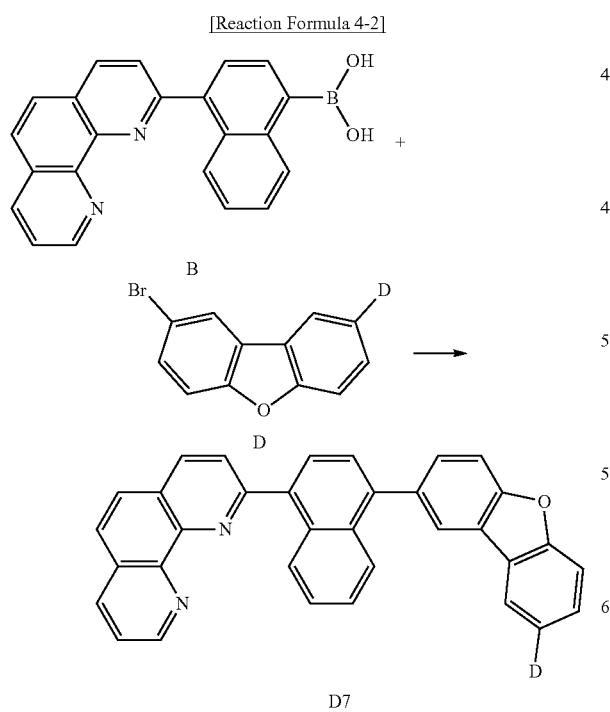

The pure Compound D7 (6.7 g, 0.014 mol, yield: 70%) was obtained by repeating the synthetic process of the Compound D1 except that the Intermediate B (7.0 g, 0.02 mol) and the Intermediate D (6.8 g, 0.02 mol) were used as the reactants.

Synthesis Example 5: Synthesis of Compound D9

(1) Synthesis of Intermediate E

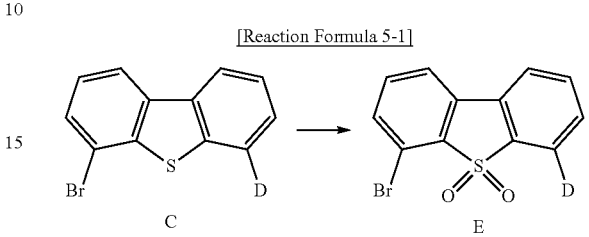

The Intermediate C (6.2 g, 0.023 mol) dissolved in acetic acid (250 ml) was put into a round bottom flask under nitrogen atmosphere, and then the solution was stirred. $H_2O_2$ (30 wt % in $H_2O$, 15.0 ml, 0.147 mol) was added into the solution, the solution was stirred at RT for 30 minutes and refluxed for 12 hours. The reaction mixture was cooled to RT, distilled water (300 ml) was added into the reaction mixture to obtain a solid, and then the solid was filtered under reduced pressure. Distilled water (300 ml) and $H_2O_2$ (30 wt % in $H_2O$, 15.0 ml) were added into the reaction mixture, the solution was stirred at RT for 1 hour and was filtered under reduced pressure to give the pure Intermediate E (6.0 g, 0.020 mol, yield: 87%).

(2) Synthesis of Compound D9

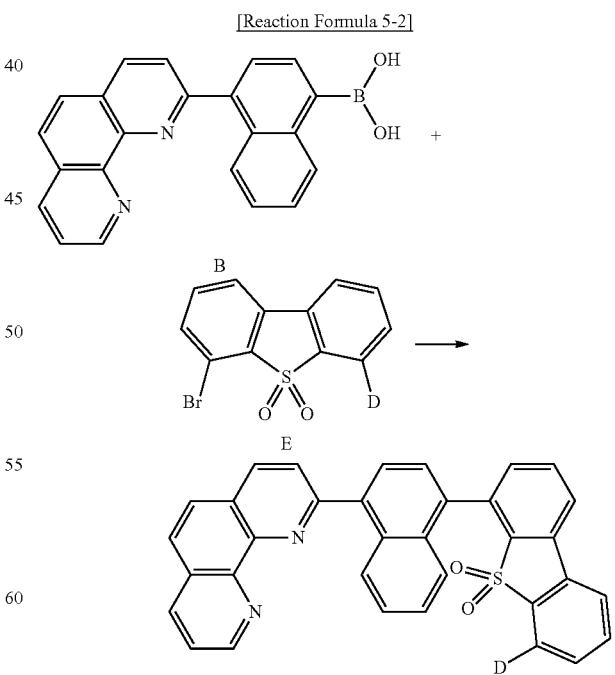

Compound D9 (3.8 g, 0.0073 mol, yield: 66%) was obtained by repeating the synthetic process of the Compound D1 except that the Intermediate B (3.8 g, 0.011 mol) and the Intermediate E (3.5 g, 0.012 mol) were used as the reactants.

Synthesis Example 6: Synthesis of Compound D11

(1) Synthesis of Intermediate F

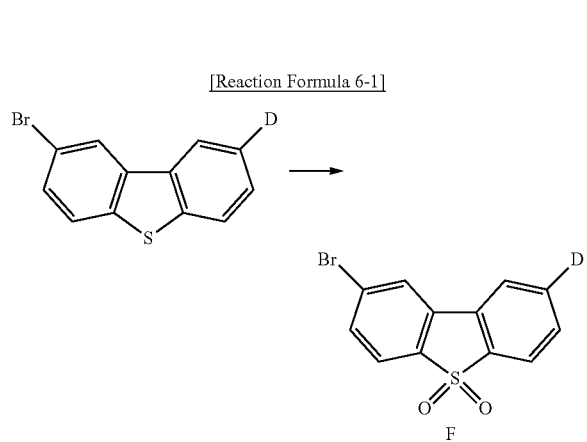

The pure Intermediate F (6.9 g, 0.020 mol, yield: 87%) was obtained by repeating the synthetic process of the Intermediate E except that 2-bromo-6-deuterium-dibenzothiophene (6.2 g, 0.023 mol) was used as the reactant.

(2) Synthesis of Compound D11

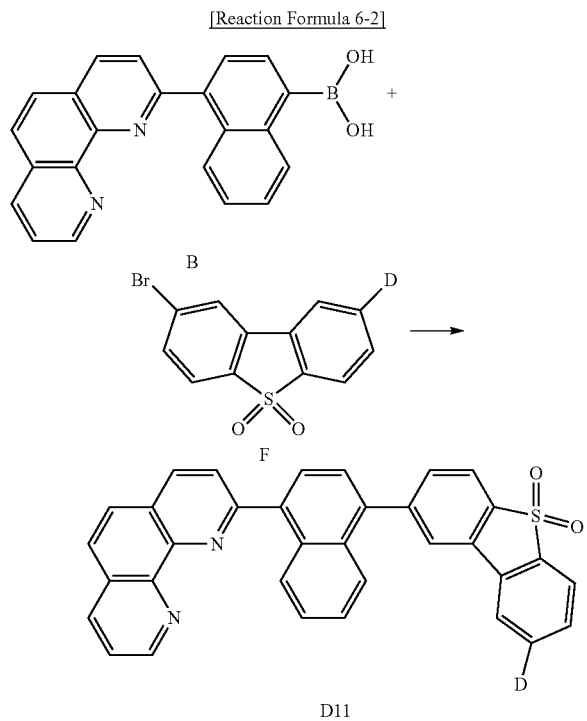

Compound D11 (3.8 g, 0.0073 mol, yield: 66%) was obtained by repeating the synthetic process of the Compound D1 except that the Intermediate B (3.8 g, 0.011 mol) and the Intermediate F (3.5 g, 0.012 mol) were used as the reactants.

Synthesis Example 7: Synthesis of Compound D12

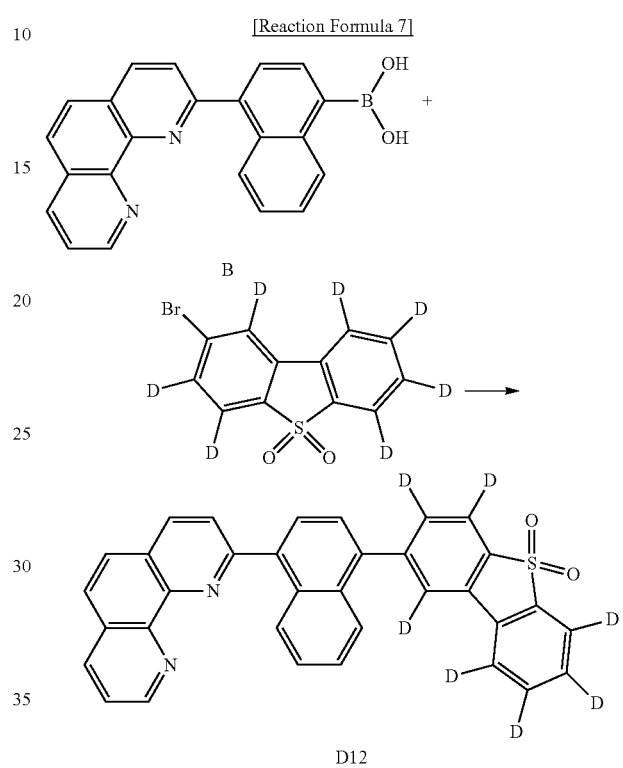

Compound D12 (7.4 g, 0.013 mol, yield: 70%) was obtained by repeating the synthetic process of the Compound D1 except that the Intermediate B (3.8 g, 0.011 mol) and 2-bromodibenzothiophene dioxide-d7 (6.0 g, 0.020 mol) were used as the reactants.

Comparative Synthesis Example 1: Synthesis of Compound Ref. 2

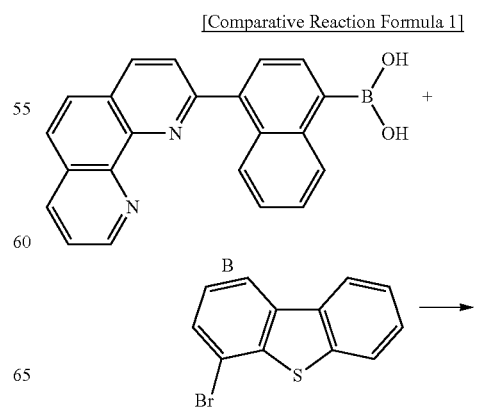

-continued

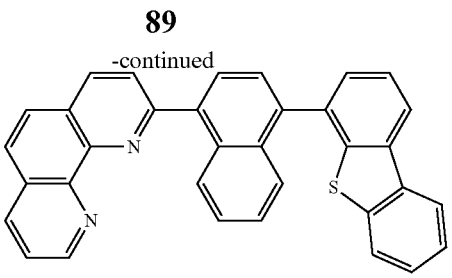

Ref. 2

The pure Compound Ref. 2 (7.2 g, 0.015 mol, yield: 75%) was obtained by repeating the synthetic process of the Compound D1 except that the Intermediate B (7.0 g, 0.02 mol) and 4-bromodibenzofuran (5.0 g, 0.02 mol) were used as the reactants.

Comparative Synthesis Example 2: Synthesis of Compound Ref. 3

(1) Synthesis of Intermediate G

[Comparative Reaction Formula 2-1]

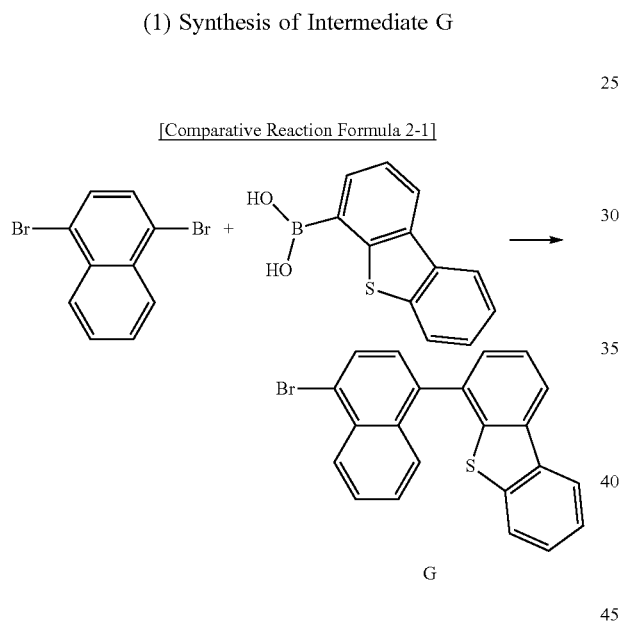

G

The pure Intermediate G (9.3 g, 0.024 mol, yield: 89%) was obtained by repeating the synthetic process of the Compound D1 except that 1,4-dibromonaphthalene (8.0 g, 0.028 mol) and dibenzothiophen-4-yl boronic acid (6.1 g, 0.027 mol) were used as the reactants.

(2) Synthesis of Intermediate H

[Reaction Formula 2-2]

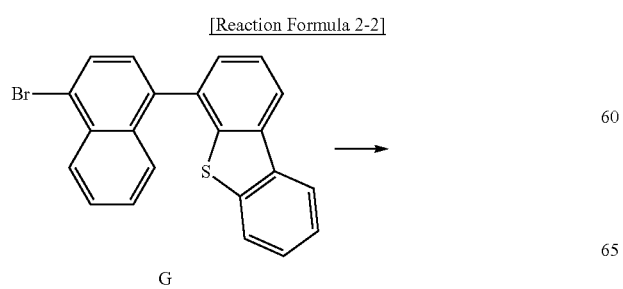

G

-continued

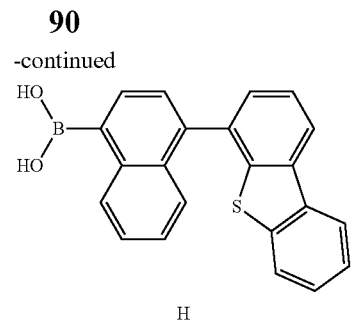

H

The pure Intermediate H (7.5 g, 0.021 mol, yield: 91%) was obtained by repeating the synthetic process of the Intermediate B except that the Intermediate G (9.0 g, 0.023 mol) was used as the reactant.

(3) Synthesis of Compound Ref 3

[Comparative Reaction Formula 2-3]

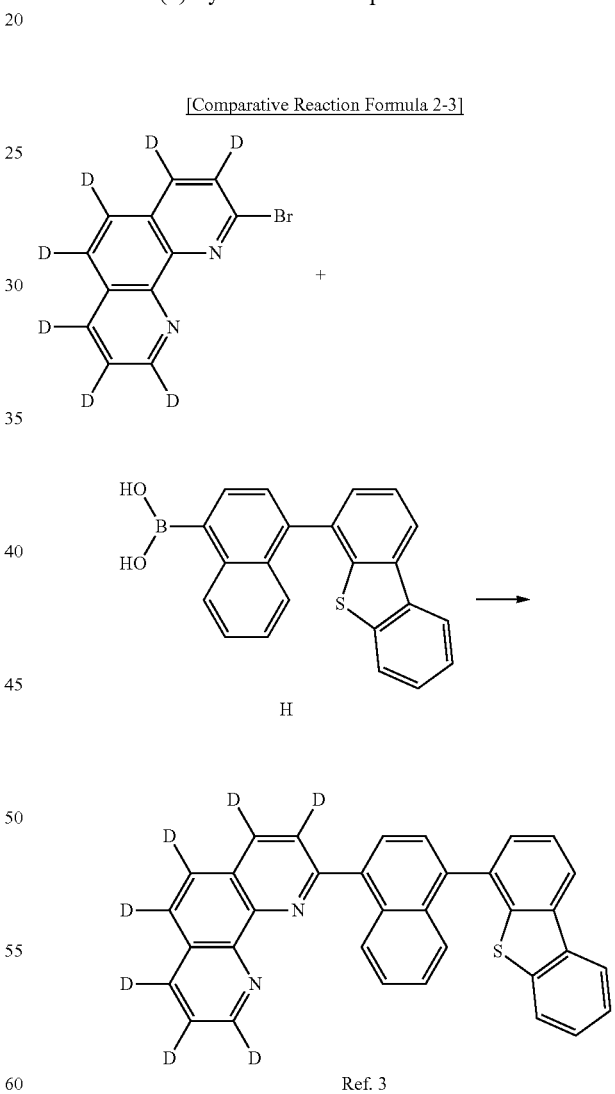

Ref. 3

The pure Compound Ref 3 (4.8 g, 0.0097 mol, yield: 81%) was obtained by repeating the synthetic process of the Compound D1 except that 2-bromophenanthroline-d7 (3.3 g, 0.012 mol) and the Intermediate H (4.4 g, 0.012 mol) were used as the reactants.

Comparative Synthesis Example 3: Synthesis of Compound Ref. 4

(1) Synthesis of Intermediate I

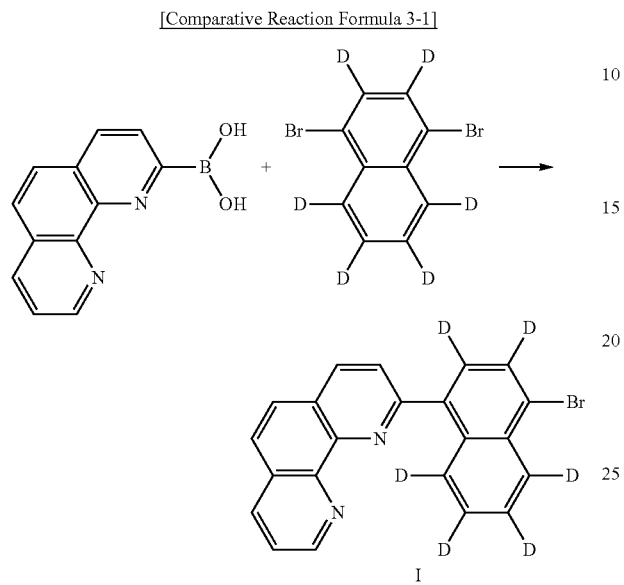

[Comparative Reaction Formula 3-1]

The Intermediate I (10.4 g, 0.0266 mol, yield: 82%) was obtained by repeating the synthetic process of the Compound D1 except that phenanthroline-2-yl boronic acid (8.1 g, 0.036 mol) and 1,4-dibromo-naphthalene-d6 (9.5 g, 0.033 mol) were used as the reactants.

(2) Synthesis of Intermediate J

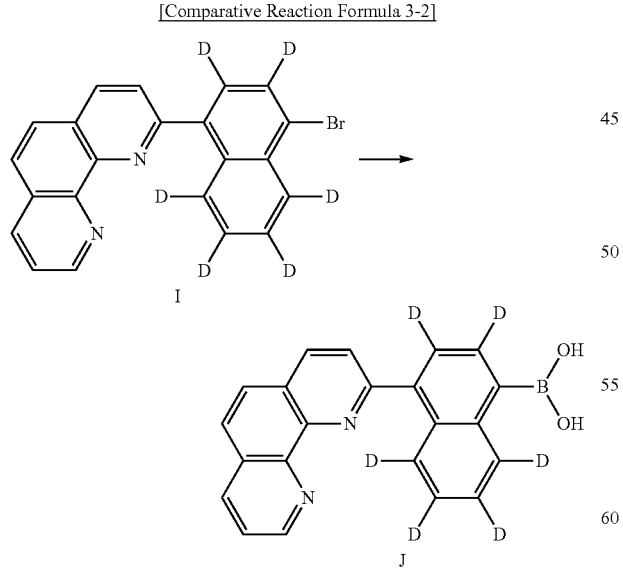

[Comparative Reaction Formula 3-2]

The pure Intermediate J (8.4 g, 0.0236 mol, yield: 89%) was obtained by repeating the synthetic process of the Intermediate B except that the Intermediate I (10.4 g, 0.0266 mol) was used as the reactant.

(3) Synthesis of Compound Ref 4

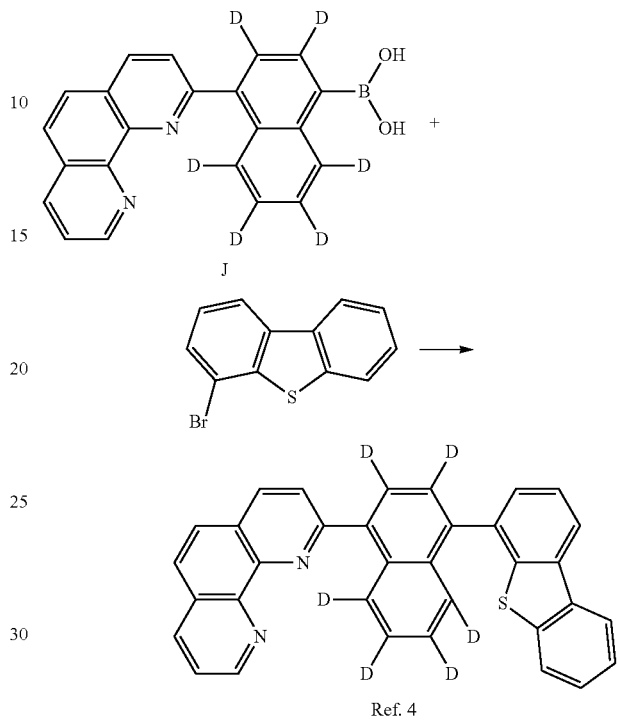

[Comparative Reaction Formula 3-3]

Ref. 4

The pure Compound Ref. 4 (6.3 g, 0.013 mol, yield: 81%) was obtained by repeating the synthetic process of the Compound D1 except that the Intermediate J (5.7 g, 0.016 mol) and 4-bromodibenzothiophene (4.5 g, 0.017 mol) were used as the reactants.

Comparative Synthesis Example 4: Synthesis of Compound Ref. 5

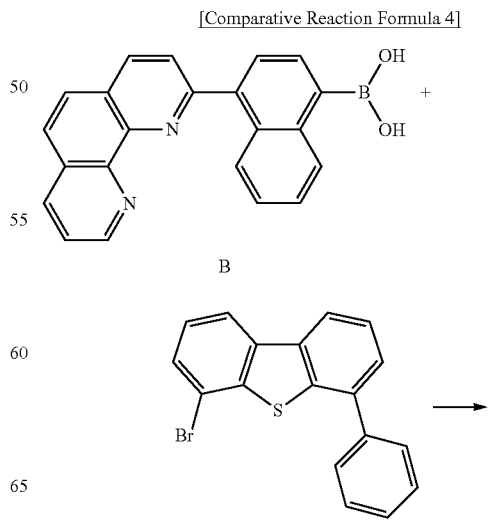

[Comparative Reaction Formula 4]

B

93

-continued

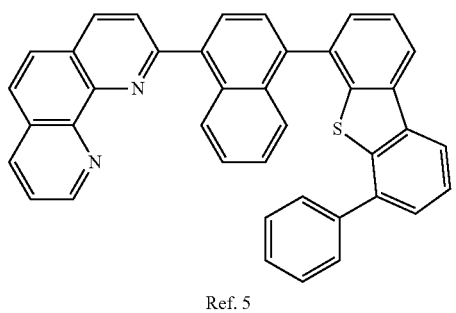

Ref. 5

The pure Compound Ref. 5 (7.2 g, 0.015 mol, yield: 75%) was obtained by repeating the synthetic process of the Compound D1 except that the Intermediate B (7.0 g, 0.02 mol) and 4-bromo-5-phenyl-dibenzothiophene (6.8 g, 0.02 mol) were used as the reactants.

Comparative Synthesis Example 5: Synthesis of Compound Ref. 6

(1) Synthesis of Intermediate K

[Comparative Reaction Formula 5-1]

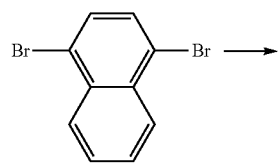

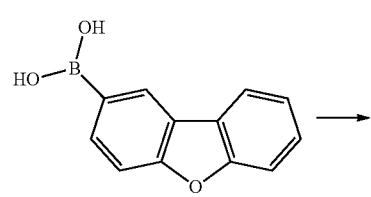

K

The Intermediate K (9.3 g, 0.025 mol, yield: 83%) was obtained by repeating the synthetic process of the Intermediate G, except that 1,4-dibromonaphthalene (9.6 g, 0.034 mol) and dibenzofuran-2-boronic acid (6.4 g, 0.030 mol) were used as the reactants.

94

(2) Synthesis of Intermediate L

[Comparative Reaction Formula 5-2]

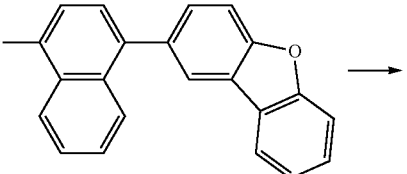

K

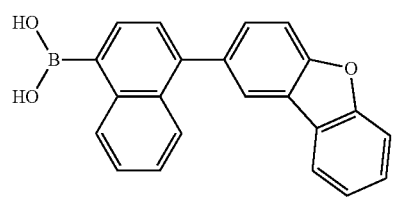

L

The pure Intermediate L (7.1 g, 0.021 mol, yield: 84%) was obtained by repeating the synthetic process of the Intermediate B except that the Intermediate K (9.3 g, 0.025 mol) was used as the reactant.

(3) Synthesis of Compound Ref 6

[Comparative Reaction Formula 5-3]

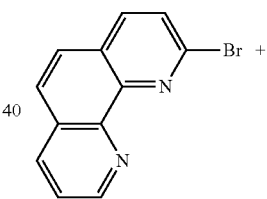

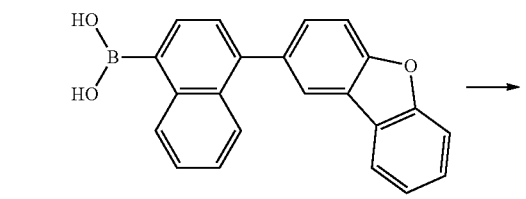

L

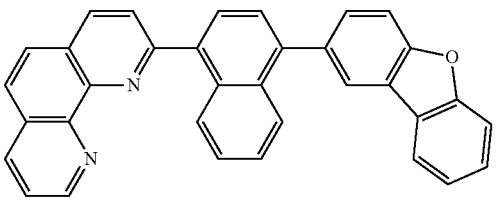

Ref. 6

The pure Compound Ref 6 (6.7 g, 0.0142 mol, yield: 71%) was obtained by repeating the synthetic process of the Compound D1 except that 2-bromophenanthroline (5.2 g, 0.02 mol) and the Intermediate L (6.8 g, 0.02 mol) were used as the reactants.

Comparative Synthesis Example 6: Synthesis of Compound Ref. 7

(1) Synthesis of Intermediate M

[Comparative Reaction Formula 6-1]

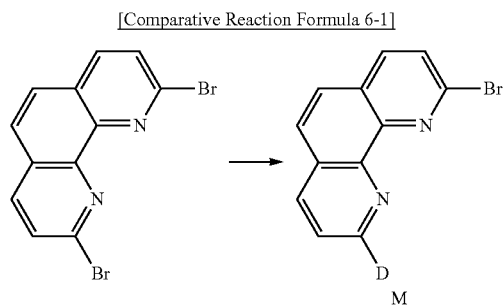

The pure Intermediate M (7.6 g, 0.029 mol, yield: 97%) was obtained by repeating the synthetic process of the Intermediate C except that 2,9-dibromophenanthroline (10.0 g, 0.030 mol) was used as the reactant.

(2) Synthesis of Compound Ref 7

[Comparative Reaction Formula 6-2]

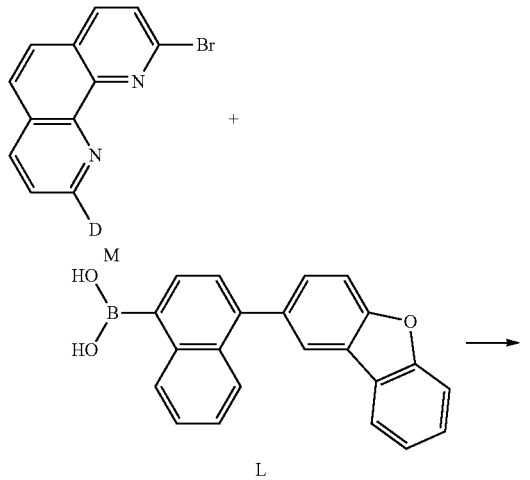

Ref. 7

The pure Compound Ref. 7 (7.1 g, 0.015 mol, yield: 75%) was obtained by repeating the synthetic process of the Compound D1 except that the Intermediate M (5.2 g, 0.02 mol) and the Intermediate L (6.8 g, 0.02 mol) were used as the reactants.

Comparative Synthesis Example 7: Synthesis of Compound Ref. 8

[Comparative Reaction Formula 7]

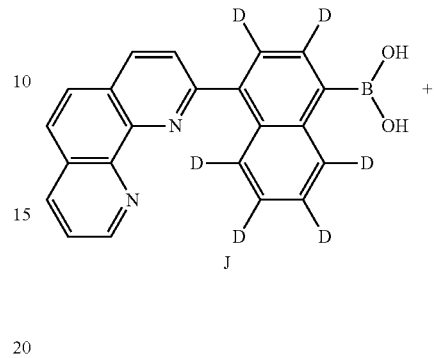

J

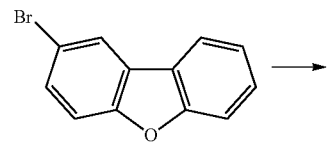

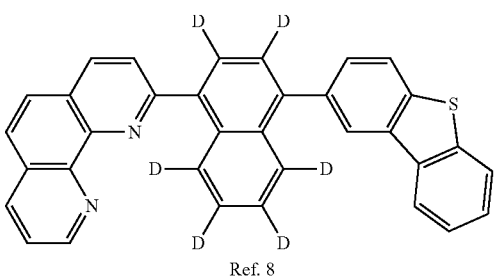

Ref. 8

The pure Compound Ref. 8 (6.3 g, 0.013 mol, yield: 81%) was obtained by repeating the synthetic process of the Compound D1 except that the Intermediate J (5.7 g, 0.016 mol) and 2-bromodibenzofuran (4.5 g, 0.017 mol) were used as the reactants.

Comparative Synthesis Example 8: Synthesis of Compound Ref. 9

(1) Synthesis of Intermediate N

[Comparative Reaction Formula 8-1]

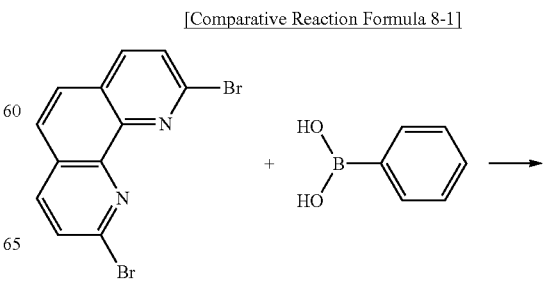

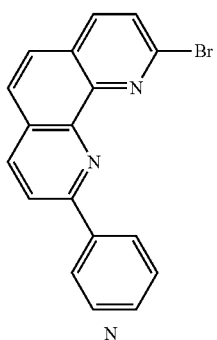

The pure Intermediate N (8.8 g, 0.026 mol, yield: 87%) was obtained by repeating the synthetic process of the Compound D1 except that 2,9-bromophenanthroline (10.0 g, 0.030 mol) and phenyl boronic acid (3.6 g, 0.030 mol) were used as the reactants.

(2) Synthesis of Compound Ref 9

[Comparative Reaction Formula 8-2]

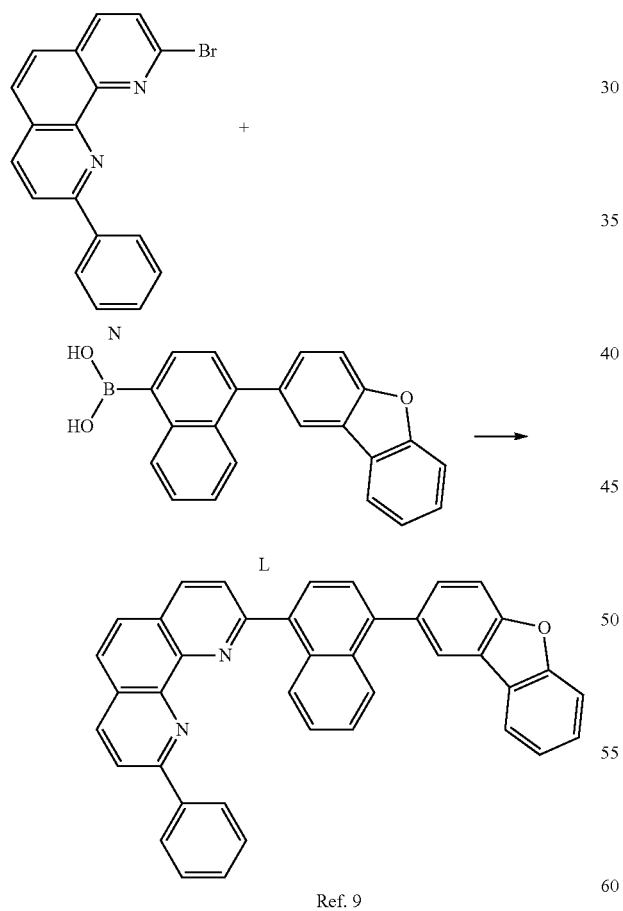

Ref. 9

The pure Compound Ref 9 (6.7 g, 0.0142 mol, yield: 71%) was obtained by repeating the synthetic process of the Compound D1 except that the Intermediate N (5.2 g, 0.02 mol) and the Intermediate L (6.8 g, 0.02 mol) were used as the reactants.

Comparative Synthesis Example 9: Synthesis of Compound Ref. 10

(1) Synthesis of Intermediate O

[Comparative Reaction Formula 9-1]

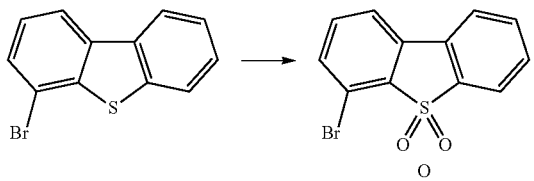

4-bromodibenzothiophene (8.0 g, 0.030 mol) dissolved in acetic acid (250 ml) was put into a round bottom flask under nitrogen atmosphere, and then the solution was stirred. $H_2O_2$ (30 wt % in $H_2O$, 15.0 ml, 0.147 mol) was added into the solution, the solution was stirred at RT for 30 minutes and refluxed for 12 hours. The reaction mixture was cooled to RT, distilled water (300 ml) was added into the reaction mixture to obtain a solid, and then the solid was filtered under reduced pressure. Distilled water (300 ml) and $H_2O_2$ (30 wt % in $H_2O$, 15.0 ml) were added into the reaction mixture, the solution was stirred at RT for 1 hour and was filtered under reduced pressure to give the pure Intermediate O (8.1 g, 0.027 mol, yield: 97%).

(2) Synthesis of Compound Ref 10

[Comparative Reaction Formula 9-2]

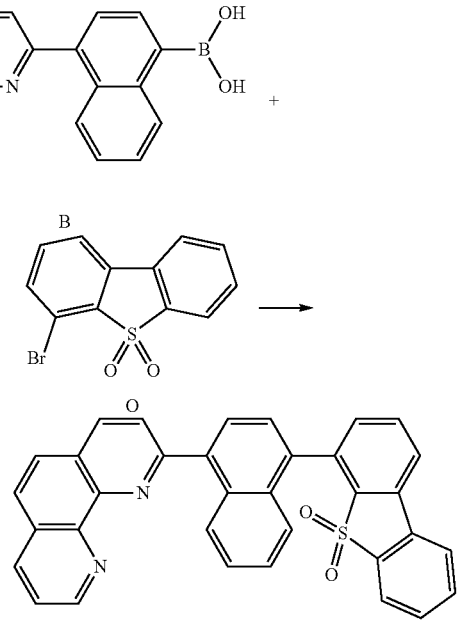

Ref. 10

The pure Compound Ref. 10 (4.3 g, 0.0083 mol, yield: 69%) was obtained by repeating the synthetic process of the Compound D1 except that the Intermediate B (4.5 g, 0.012 mol) and the Intermediate O (4.5 g, 0.015 mol) were used as the reactants.

Comparative Synthesis Example 10: Synthesis of Compound Ref. 11

(1) Synthesis of Intermediate P

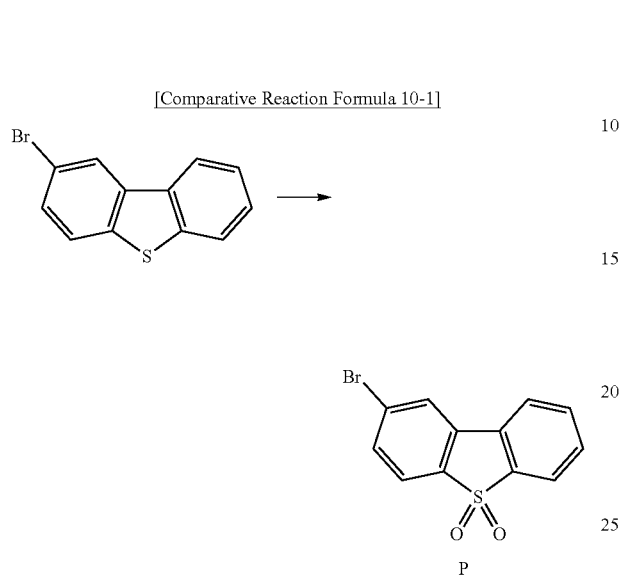

The pure Intermediate P (8.6 g, 0.029 mol, yield: 97%) was obtained by repeating the synthetic process of the Intermediate O except that 2-bromodibenzothiophene (8.0 g, 0.030 mol) was used as the reactant.

(2) Synthesis of Intermediate Q

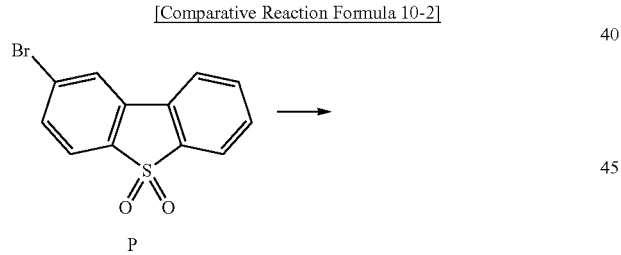

The pure Intermediate Q (7.4 g, 0.028 mol, yield: 93%) was obtained by repeating the synthetic process of the Intermediate B except that the Intermediate P (8.9 g, 0.030 mol) was used as the reactant.

(3) Synthesis of Intermediate R

[Comparative Reaction Formula 10-3]

The pure Intermediate R (10.3 g, 0.024 mol, yield: 89%) was obtained by repeating the synthetic process of the Intermediate G except that the 1,4-dibromonaphthalene (12.0 g, 0.042 mol) and the Intermediate Q (7.0 g, 0.027 mol) were used as the reactants.

(4) Synthesis of Compound Ref 11

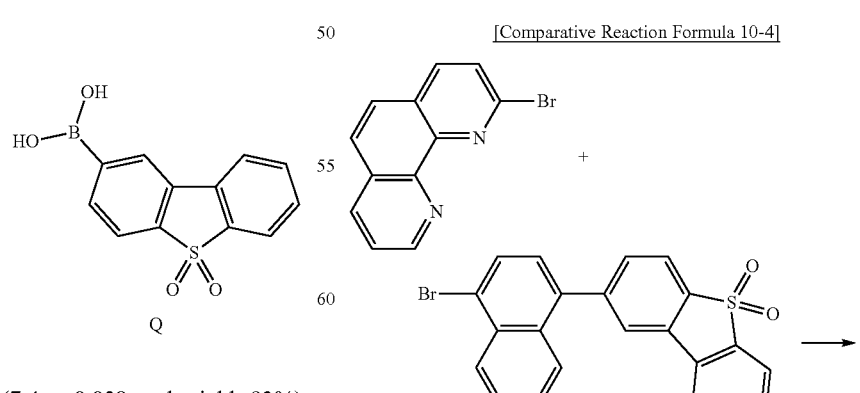

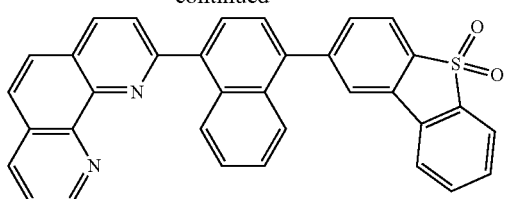

Ref. 11

The pure Compound Ref. 11 (5.4 g, 0.010 mol, yield: 63%) was obtained by repeating the synthetic process of the Compound D1 except that 2-bromophenanthroline (4.1 g, 0.016 mol) and the Intermediate R (5.9 g, 0.014 mol) were used as the reactants.

Comparative Synthesis Example 11: Synthesis of Compound Ref. 12

[Comparative Reaction Formula 11]

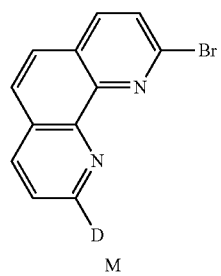

M

+

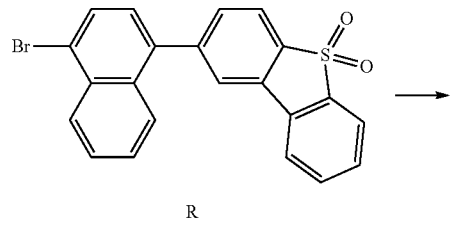

R

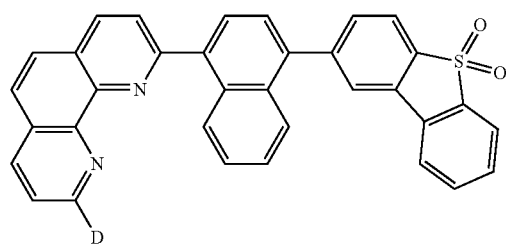

Ref. 12

The pure Compound Ref 12 (5.8 g, 0.011 mol, yield: 78%) was obtained by repeating the synthetic process of the Compound D1 except that the Intermediate M (4.2 g, 0.016 mol) and the Intermediate R (5.9 g, 0.014 mol) were used as the reactants.

Comparative Synthesis Example 12: Synthesis of Compound Ref. 13

[Comparative Reaction Formula 12]

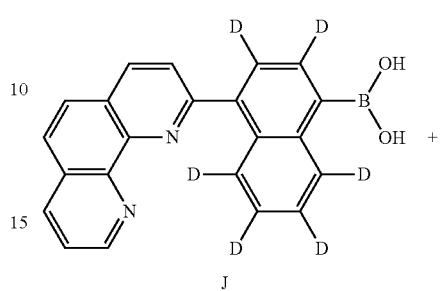

J

+

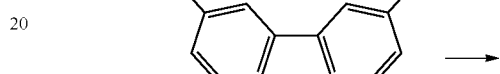

F

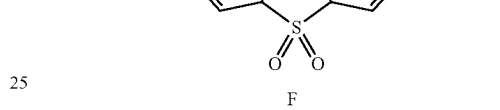

Ref. 13

The pure Compound Ref 13 (6.8 g, 0.013 mol, yield: 65%) was obtained by repeating the synthetic process of the Compound D1 except that the Intermediate J (7.0 g, 0.016 mol) and the Intermediate F (6.4 g, 0.022 mol) were used as the reactants.

Comparative Synthesis Example 13: Synthesis of Compound Ref. 14

(1) Synthesis of Intermediate S

[Comparative Reaction Formula 13-1]

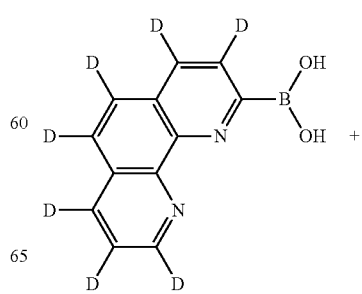

+

-continued

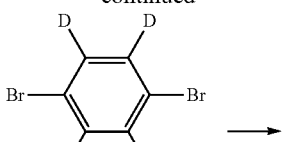

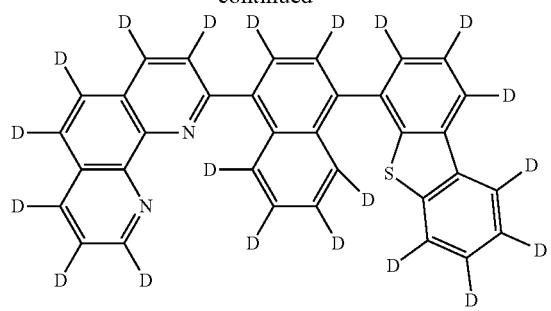

Ref. 14

The pure Compound Ref 14 (6.1 g, 0.012 mol, yield: 75%) was obtained by repeating the synthetic process of the Compound D1 except that the Intermediate S (6.5 g, 0.016 mol) and dibenzothiophen-4-yl boronic acid-d7 (4.0 g, 0.017 mol) were used as the reactants.

Comparative Synthesis Example 14: Synthesis of Compound Ref. 15

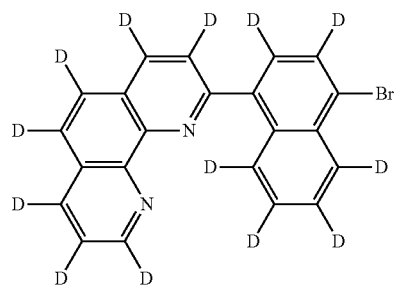

The pure Intermediate S (6.5 g, 0.016 mol, yield: 80%) was obtained by repeating the synthetic process of the Intermediate G except that 1,10-phenanthroline-2-boronic acid-d7 (4.6 g, 0.020 mol) and 1,4-dibromonaphthalene-d6 (5.8 g, 0.020 mol) were used as the reactants.

(2) Synthesis of Compound Ref 14

[Comparative Reaction Formula 13-2]

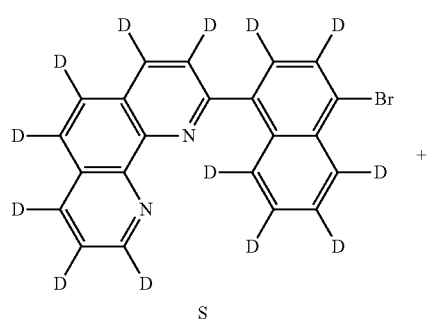

+

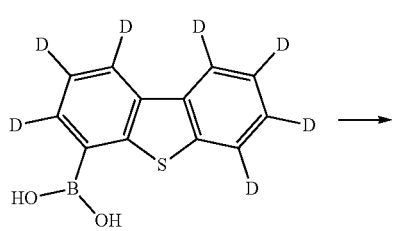

[Comparative Reaction Formula 14]

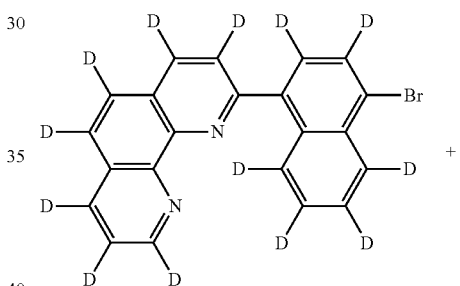

Ref. 15

The pure Compound Ref 15 (7.5 g, 0.014 mol, yield: 70%) was obtained by repeating the synthetic process of the Compound D1 except that the Intermediate S (6.5 g, 0.016 mol) and dibenzofuran-2-yl boronic acid-d7 (4.0 g, 0.018 mol) were used as the reactants.

Comparative Synthesis Example 15: Synthesis of Compound Ref. 16

[Comparative Reaction Formula 15]

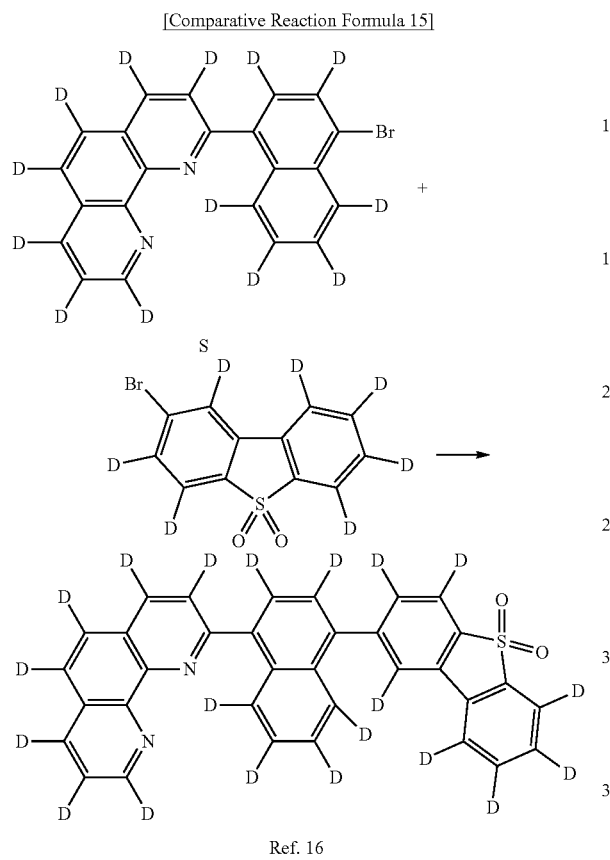

Ref. 16

The pure Compound Ref 16 (7.5 g, 0.014 mol, yield: 70%) was obtained by repeating the synthetic process of the Compound D1 except that the Intermediate S (8.0 g, 0.020 mol) and 2-bromodibenzothiophene dioxide-d7 (7.0 g, 0.023 mol) were used as the reactants.

Example 1 (Ex. 1): Fabrication of OLED

An organic light emitting diode having a tandem structure where the Compound D1 was applied as the host into an N-CGL was fabricated. A glass substrate onto which ITO coated as a thin film was washed UV ozone, mounted onto evaporation system and transferred to a vacuum chamber for depositing emissive layer. Subsequently, an emissive layer and a cathode were deposited by evaporation from a heating boat under about $10^{-7}$ Torr as the following order:

An HIL (HAT-CN, 50 Å); an HTL1 (NPB, 300 Å), an EML1 (Host 1 (97 wt %), Dopant 2 (3 wt %, 230 Å), an ETL1 (ZADN, 200 Å), an N-CGL (Compound D1 (98 wt %), Li (2 wt %), 120 Å), p-CGL (HAT-CN, 50 Å), an HTL2 (NPB, 450 Å), an EML2 (Host 1 (97 wt %), Dopant 2 (3 wt %), 230 Å), an ETL2 (ZADN, 300 Å), an EIL (LiF (50 wt %), Yb (50 wt %), 20 Å), a cathode (Ag:Mg=10:1 by weight, 130 Å).

After deposition of emissive layer and the cathode, the OLED was transferred from the deposition chamber to a dry box for film formation, followed by encapsulation using UV-curable epoxy and moisture getter.

Examples 2-7 (Ex. 2-7): Fabrication of OLED

An OLED was fabricated using the same procedure and the same material as in Example 1, except that Compound D2 (Ex. 2), Compound D6 (Ex. 3), Compound D7 (Ex. 4), Compound D9 (Ex. 5), Compound D11 (Ex. 6) and Compound D12 (Ex. 7), respectively, as the host in the N-CGL instead of Compound D1.

Comparative Example 1 (Ref 1): Fabrication of OLED

An OLED was fabricated using the same procedure and the same material as in Example 1, except the following Ref-1 as the host in the N-CGL instead of Compound D1.

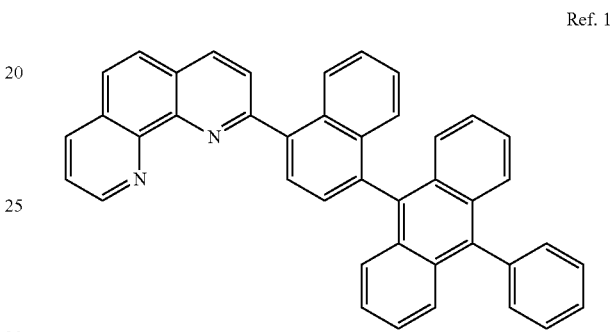

Ref. 1

Comparative Example 2-16 (Ref. 2-16): Fabrication of OLEDs

An OLED was fabricated using the same procedure and the same material as in Example 1, except Ref. 2 to Ref 16, respectively as the host in the N-CGL instead of Compound D1.

Experimental Example 1: Measurement of Luminous Properties of OLEDs

Each of the OLEDs, having 9 mm² of emission area, fabricated in Examples 1 to 7 and Comparative Examples 1 to 15 was connected to an external power source and then luminous properties for all the OLEDs were evaluated using a constant current source (KEITHLEY) and a photometer PR650 at room temperature. In particular, driving voltage (V), External quantum efficiency (EQE, relative value) and luminous lifespan ($LT_{95}$, relative value) at which the luminance was reduced to 95% from initial luminance was measured at a luminance of 1000 cd/m². The measurement results are indicated in the following Table 1.

TABLE 1

| Luminous Property of OLED | | | | |
|---|---|---|---|---|
| Sample | Compound | Voltage($\Delta$V) | EQE (%) | $LT_{95}$ (%) |
| Ref. 1 | Ref. 1 | 0.00 | 100 | 100 |
| Ref. 2 | Ref. 2 | −0.25 | 107 | 108 |
| Ref. 3 | Ref. 3 | −0.28 | 103 | 111 |
| Ref. 4 | Ref. 4 | −0.08 | 99 | 105 |
| Ref. 5 | Ref. 5 | 0.05 | 91 | 97 |
| Ref. 6 | Ref. 6 | −0.25 | 109 | 102 |
| Ref. 7 | Ref. 7 | −0.26 | 106 | 107 |
| Ref. 8 | Ref. 8 | −0.11 | 105 | 103 |

TABLE 1-continued

Luminous Property of OLED

| Sample | Compound | Voltage($\Delta V$) | EQE (%) | $LT_{95}$ (%) |
|---|---|---|---|---|
| Ref. 9 | Ref. 9 | 0.08 | 82 | 89 |
| Ref. 10 | Ref. 10 | 0.05 | 71 | 72 |
| Ref. 11 | Ref. 11 | 0.08 | 74 | 76 |
| Ref. 12 | Ref. 12 | 0.12 | 80 | 82 |
| Ref. 13 | Ref. 13 | 0.02 | 84 | 90 |
| Ref. 14 | Ref. 14 | −0.29 | 118 | 131 |
| Ref. 15 | Ref. 15 | −0.23 | 115 | 118 |
| Ref. 16 | Ref. 16 | −0.12 | 106 | 115 |
| Ex. 1 | D1 | −0.28 | 115 | 127 |
| Ex. 2 | D2 | −0.25 | 108 | 124 |
| Ex. 3 | D6 | −0.20 | 113 | 120 |
| Ex. 4 | D7 | −0.22 | 118 | 122 |
| Ex. 5 | D9 | −0.05 | 105 | 117 |
| Ex. 6 | D11 | 0.01 | 105 | 113 |
| Ex. 7 | D12 | −0.08 | 103 | 115 |

As indicated in Table 1, compared to the OLED fabricated in Ref. 1 where the N-CGL includes the Compound Ref 1 with an anthracene moiety, the OLEDs fabricated in Examples where the organic compound including the fused hetero aromatic moiety including oxygen or sulfur atom as a nuclear atom lowered their driving voltages and improved their luminous efficiency and luminous lifespan.

Compared to the OLEDs fabricated in Refs. 2, 6 and 10-11 where the N-CGL includes Compounds not deuterated in the whole molecule, the OLEDs fabricated in Examples where the N-CGL includes the organic compounds in which at least one nuclear carbon atom within the fused hetero aromatic moiety is deuterated showed equivalent driving voltages, but improved their luminous efficiency and luminous lifespan significantly.

In addition, compared to the OLEDs fabricated in Refs. 3-4, 7-8 and 12-13 where the N-CGL includes compounds in which the nuclear carbon atoms of the phenanthroline moiety or the center linker moiety, the OLEDs fabricated in Examples where the N-CGL includes the organic compounds in which at least one nuclear carbon atom within the fused hetero aromatic moiety is deuterated showed equivalent driving voltages, but improved their luminous efficiency and luminous lifespan significantly.

Moreover, compared to the OLEDs fabricated in Refs. 14-16 where the N-CGL includes compounds in which all the nuclear carbon atoms of the whole molecule, the OLEDs fabricated in Examples where the N-CGL includes the organic compound in which only at least one carbon atom with the fused hetero aromatic moiety is deuterated showed equivalent driving voltages and very similar luminous efficiency and luminous lifespan.

It will be apparent to those skilled in the art that various modifications and variations can be made in the present disclosure without departing from the scope of the invention. Thus, it is intended that the present disclosure cover the modifications and variations of the present disclosure provided they come within the scope of the appended claims.

The invention claimed is:

1. An organic compound having the following structure of Formula 1:

[Formula 1]

wherein $Ar_1$ is $C_6$-$C_{30}$ arylene or $C_3$-$C_{30}$ hetero arylene, each of the $C_6$-$C_{30}$ arylene or the $C_3$-$C_{30}$ hetero arylene is independently unsubstituted or substituted with at least one of a $C_1$-$C_{10}$ alkyl group, a $C_6$-$C_{20}$ aryl group and a $C_3$-$C_{20}$ hetero aryl group; A has the following structure of Formula 2; B has the following structure of Formula 3; and m is 0 or 1;

[Formula 2]

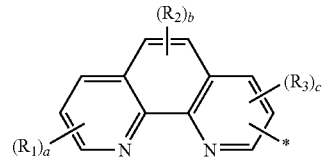

wherein each of $R_1$ to $R_3$ is independently protium, halogen, a cyano group, a $C_1$-$C_{20}$ alkyl group, a $C_1$-$C_{20}$ halo alkyl group, a $C_1$-$C_{20}$ alkoxy group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, the $C_1$-$C_{20}$ alkoxy group is unsubstituted or substituted with halogen, and each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group; each of a, b and c is a number of a substituent, a is an integer of 0 to 3, each of b and c is independently an integer of 0 to 2;

[Formula 3]

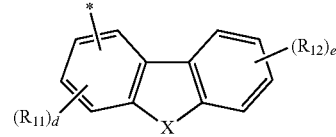

wherein X is O, S or $SO_2$; each of $R_{11}$ and $R_{12}$ is independently protium, deuterium, halogen, a cyano group, a $C_1$-$C_{20}$ alkyl group, a $C_1$-$C_{20}$ halo alkyl group, a $C_1$-$C_{20}$ alkoxy group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group, at least one of $R_{11}$ and $R_{12}$ is deuterium, $R_{11}$ is identical to or different from each other when d is two or more and $R_{12}$ is identical to or different from each other when e is two or more; each of d and e is a number of a substituent, d is an integer of 0 to 3 and e is an integer of 0 to 4, at least one of d and e is not 0.

2. The organic compound of claim 1, wherein $Ar_1$ in Formula 1 is selected from the following moieties:

A-1 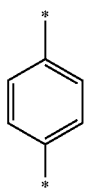
A-2 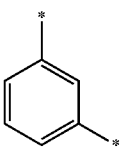
A-3 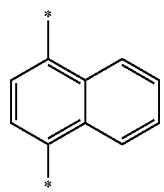
A-4 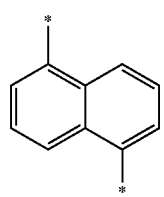
A-5 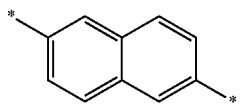
A-6 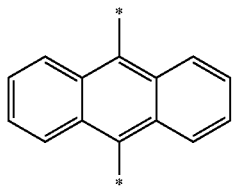
A-7 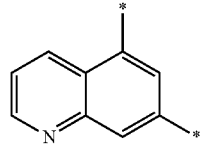
A-8 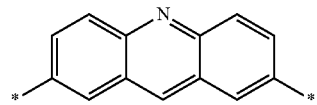
A-9 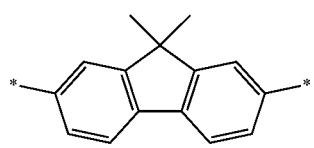
-continued
A-10 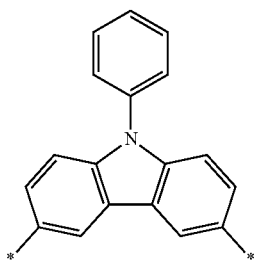
A-11 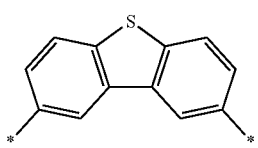
A-12 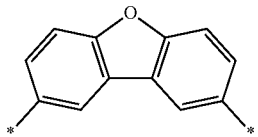
A-13 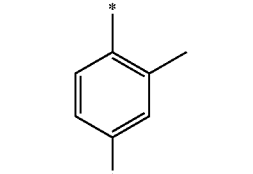
A-14 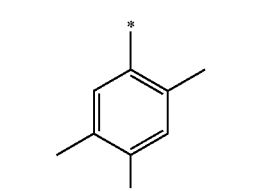
A-15 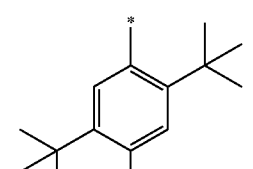
A-16 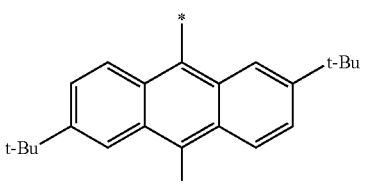
A-17 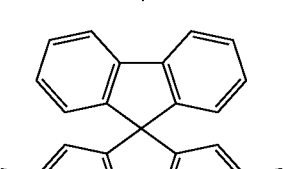
3. The organic compound of claim 1, wherein A in Formula 1 is selected from the following moieties:

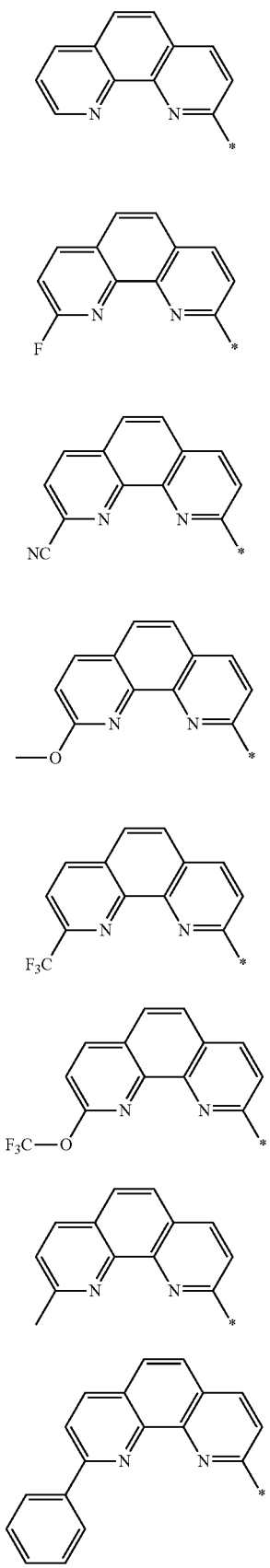
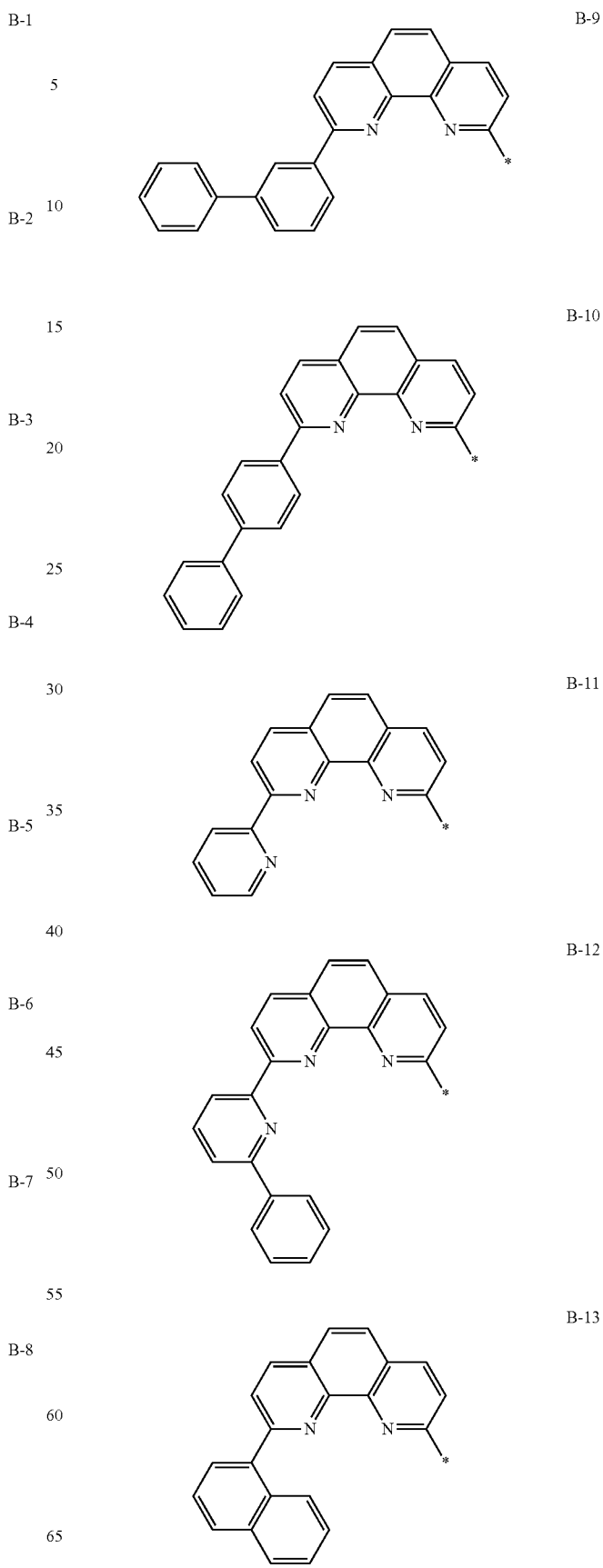

-continued
B-14
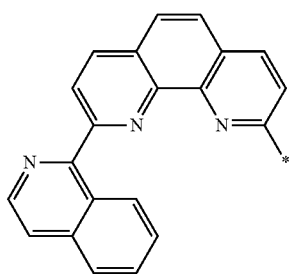
B-15
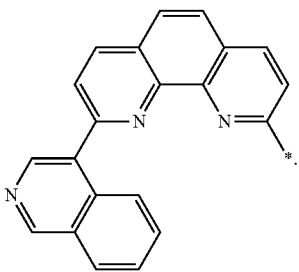
4. The organic compound of claim 1, wherein B in Formula 1 is selected from the following moieties:
C-1
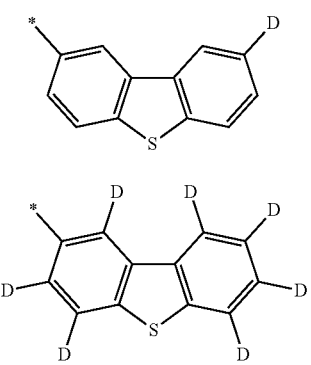
C-2
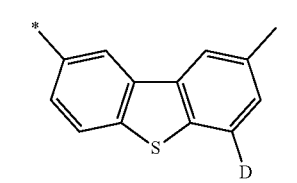
C-3
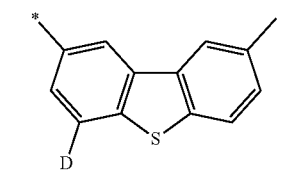
C-4
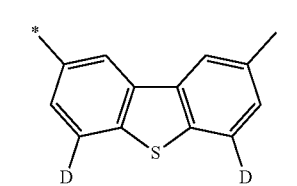
C-5
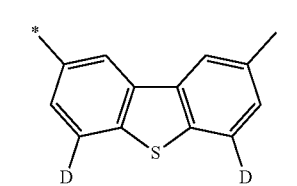
-continued
C-6
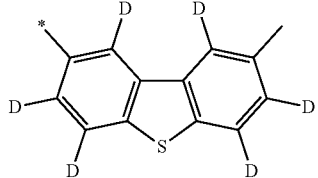
C-7
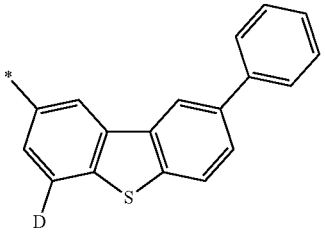
C-8
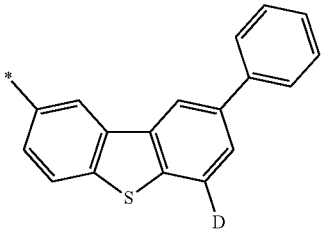
C-9
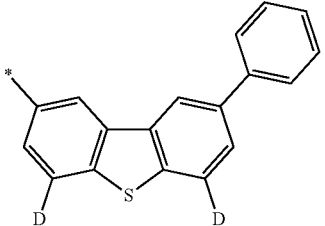
C-10
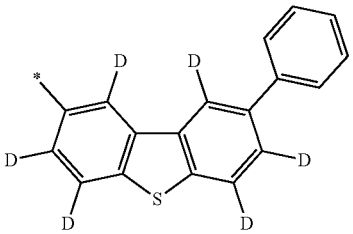
C-11
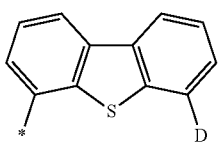
C-12
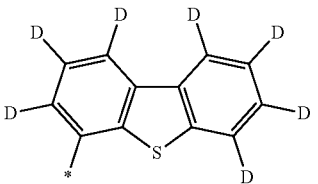

C-13
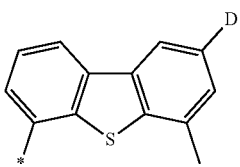
C-14
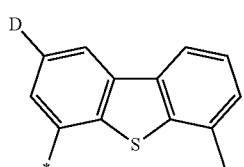
C-15
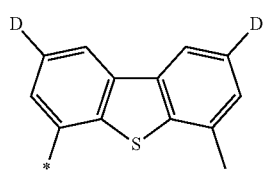
C-16
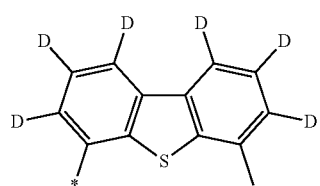
C-17
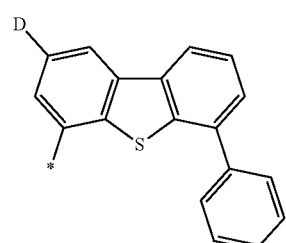
C-18
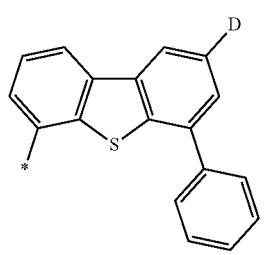
C-19
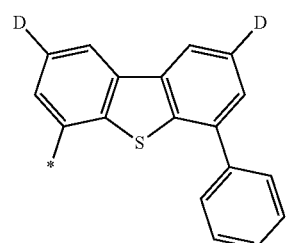
C-20
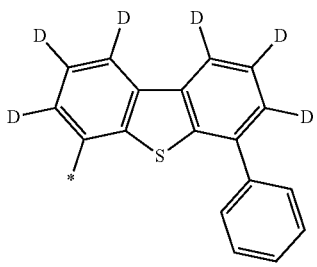
C-21
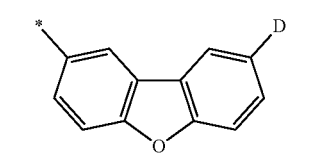
C-22
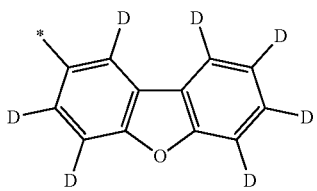
C-23
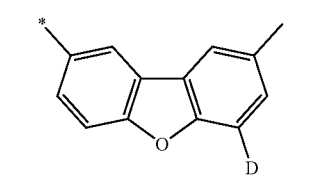
C-24
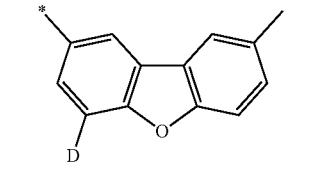
C-25
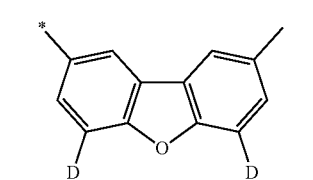
C-26
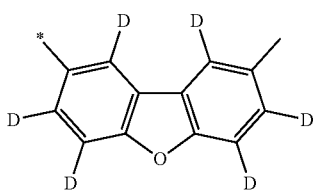
C-27
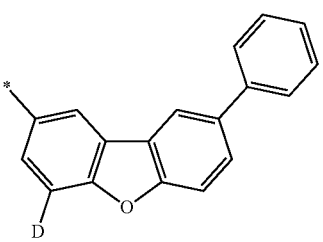

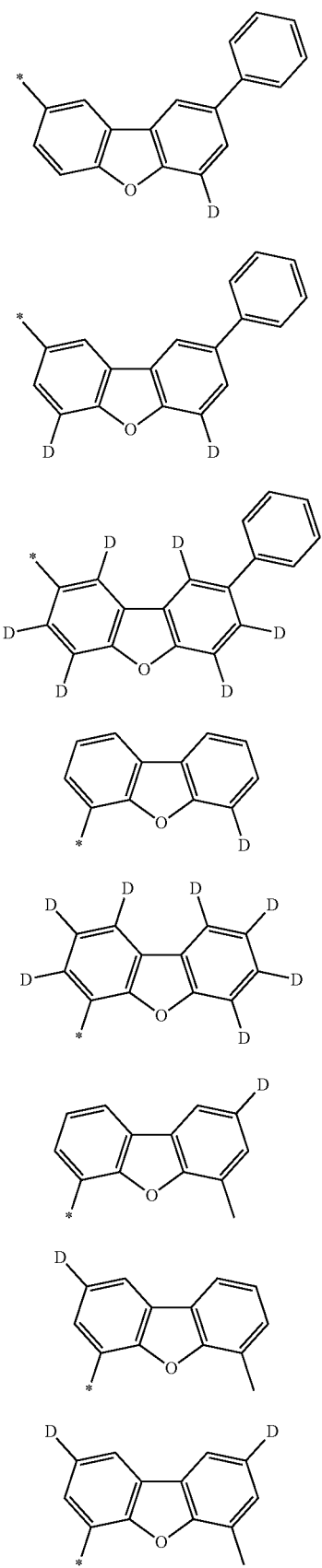
C-28
C-29
C-30
C-31
C-32
C-33
C-34
C-35
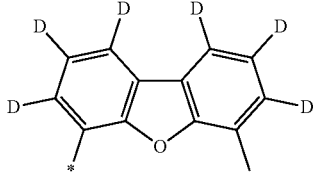
C-36
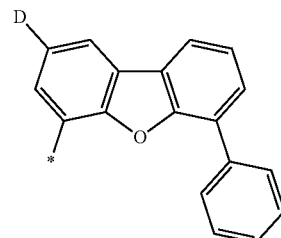
C-37
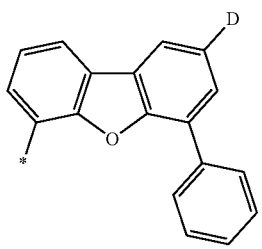
C-38
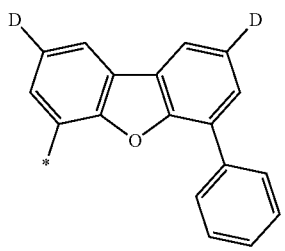
C-39
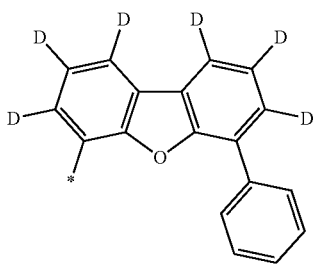
C-40
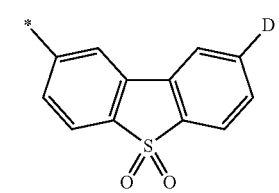
C-41
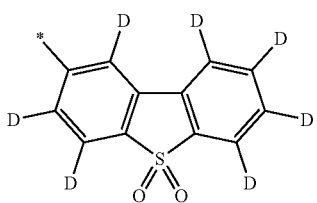
C-42

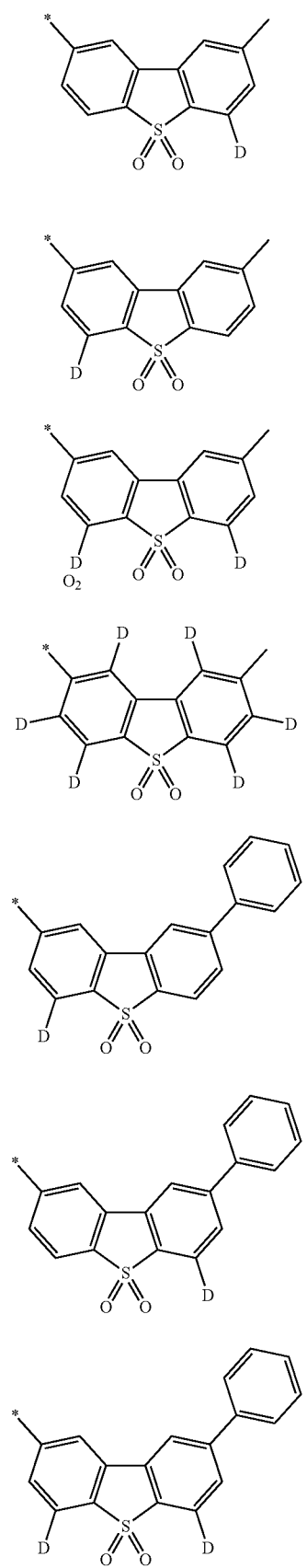
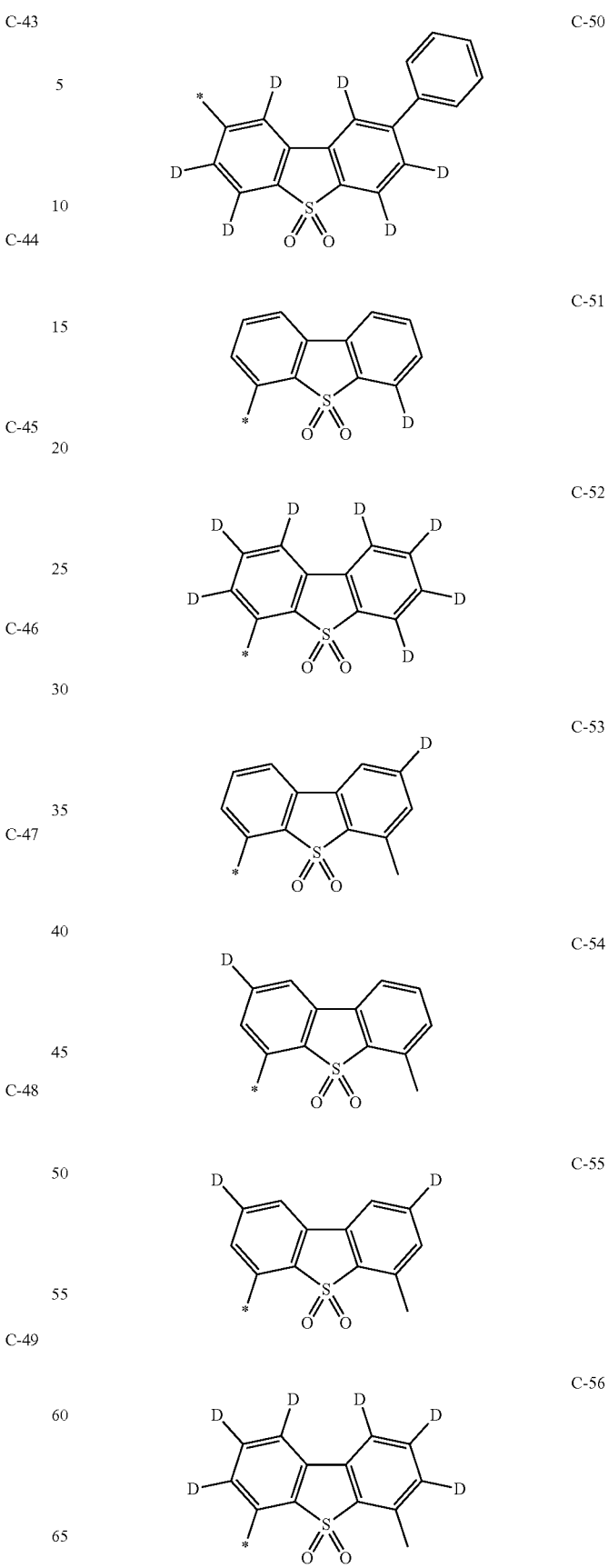

C-57 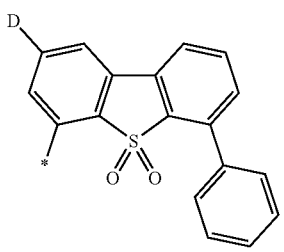
C-58 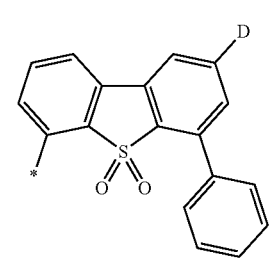
C-59 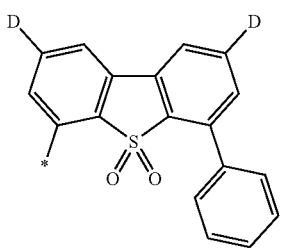
C-60 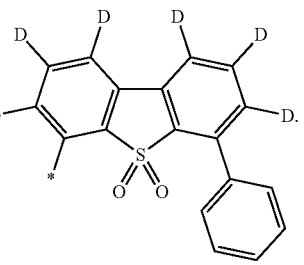
5. The organic compound of claim 1, wherein the organic compound is selected from the following compounds:
D1 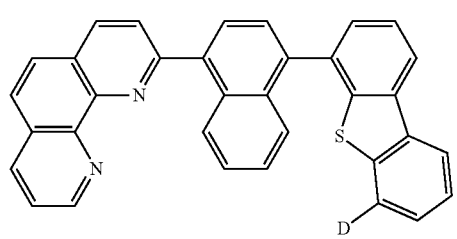
D2 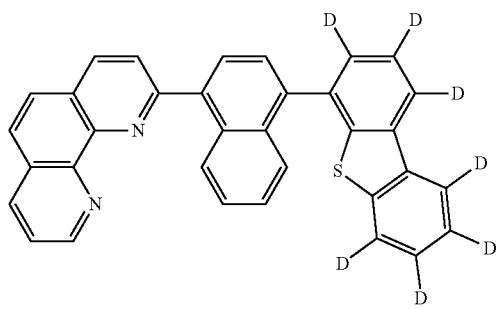
D3 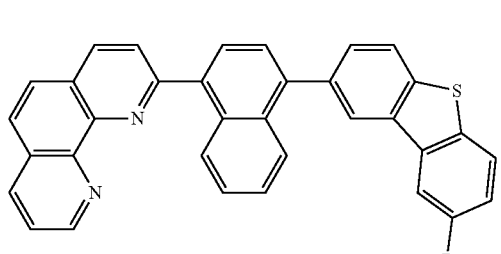
D4 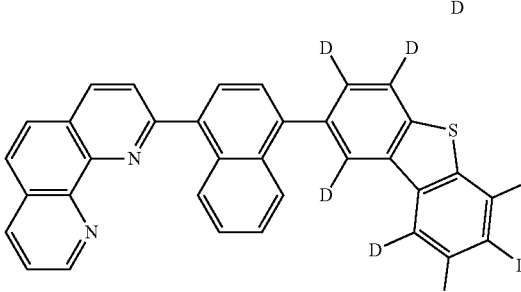
D5 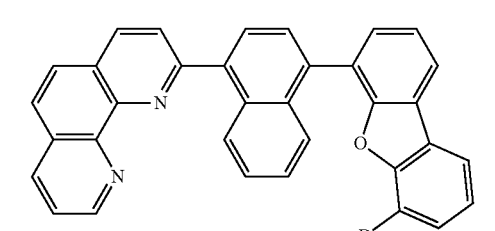
D6 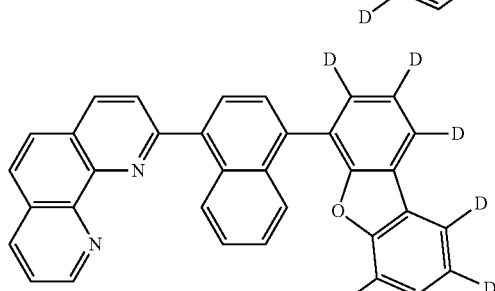
D7 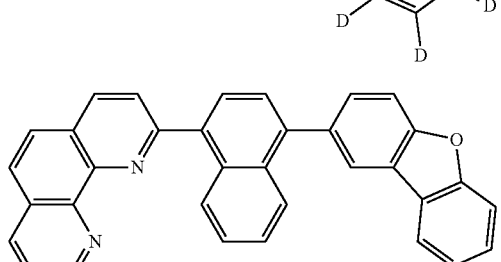

-continued

D8

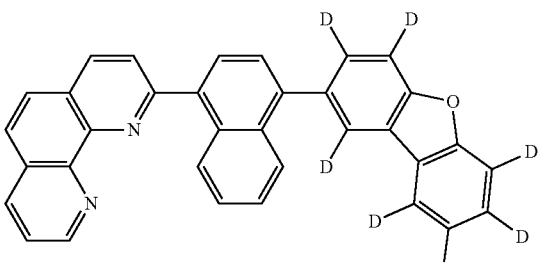

D9

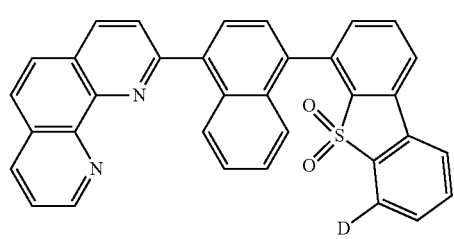

D10

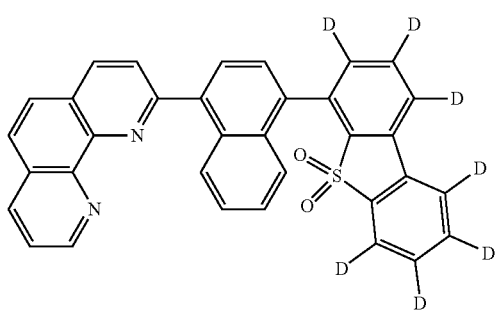

D11

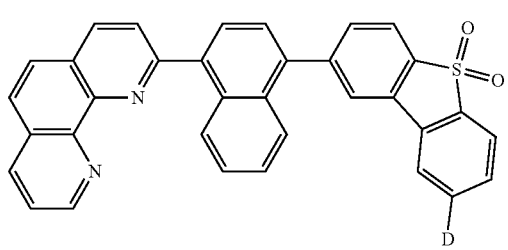

D12

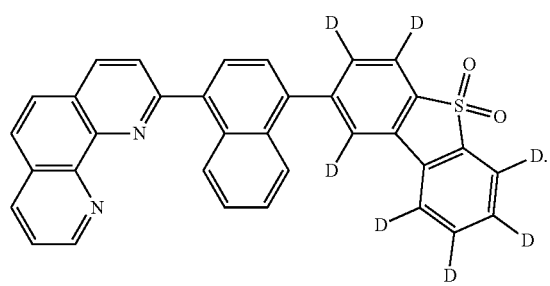

6. An organic light emitting diode, comprising:
a first electrode;
a second electrode facing the first electrode; and
an emissive layer disposed between the first electrode and the second electrode,
wherein the emissive layer includes at least one emitting material layer and at least one electron transport layer disposed between the at least one emitting material layer and the second electrode, and wherein the at least one electron transport layer includes an organic compound having the following structure of Formula 1:

[Formula 1]

wherein $Ar_1$ is $C_6$-$C_{30}$ arylene or $C_3$-$C_{30}$ hetero arylene; A has the following structure of Formula 2; B has the following structure of Formula 3; and m is 0 or 1;

[Formula 2]

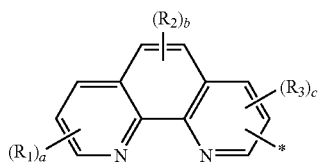

wherein each of $R_1$ to $R_3$ is independently protium, halogen, a cyano group, a $C_1$-$C_{20}$ alkyl group, a $C_1$-$C_{20}$ halo alkyl group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group; each of a, b and c is a number of a substituent, a is an integer of 0 to 3, each of b and c is independently an integer of 0 to 2;

[Formula 3]

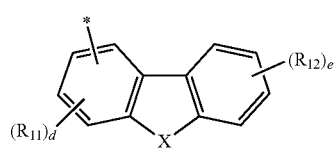

wherein X is O, S or SO; each of $R_{11}$ and $R_{12}$ is independently protium, deuterium, halogen, a cyano group, a $C_1$-$C_{20}$ alkyl group, a $C_1$-$C_{20}$ halo alkyl group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group, at least one of $R_n$ and $R_{12}$ is deuterium; each of d and e is a number of a substituent, d is an integer of 0 to 3 and e is an integer of 0 to 4, at least one of d and e is not 0.

7. The organic light emitting diode of claim 6, wherein $Ar_1$ in Formula 1 is selected from the following moieties:

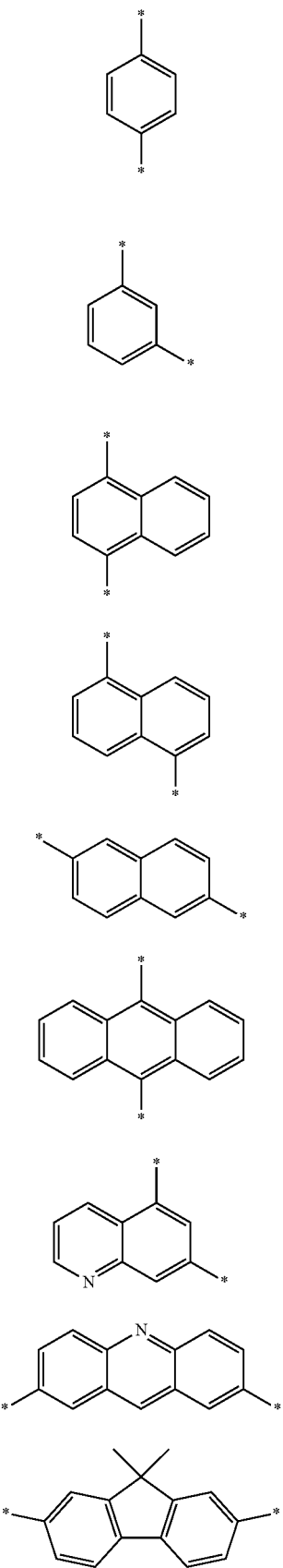
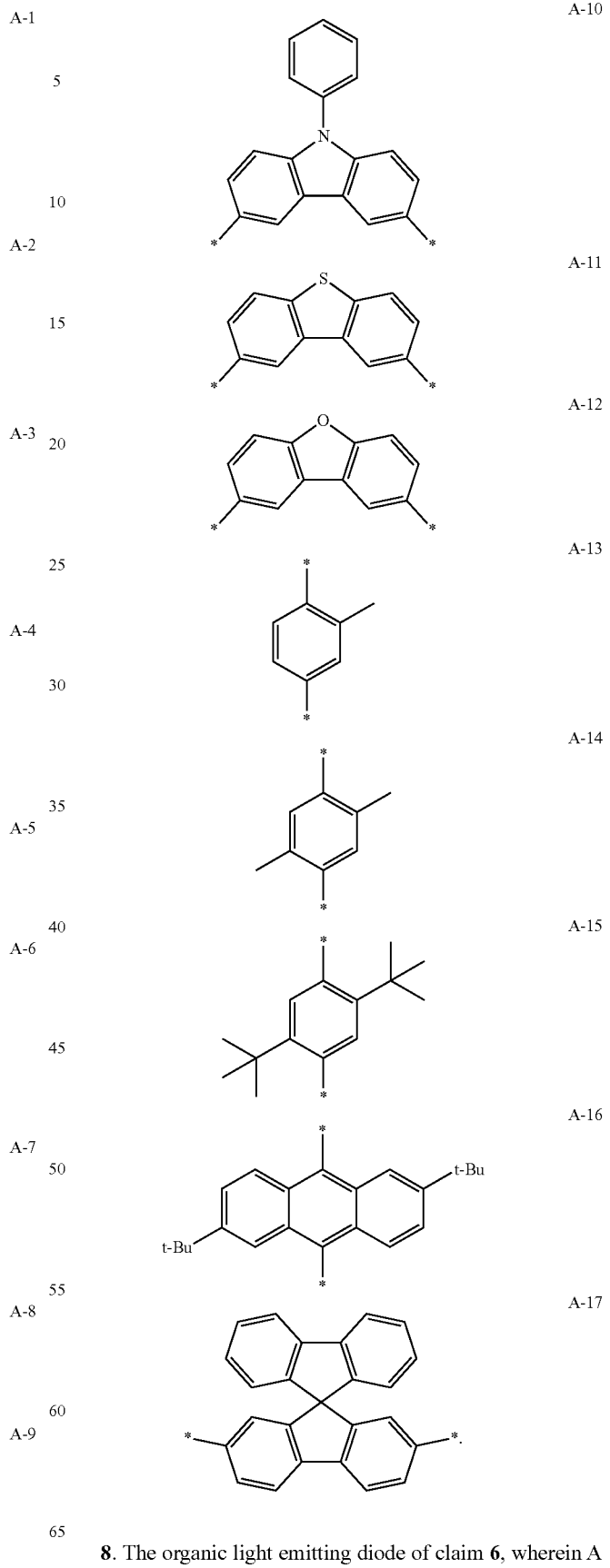
8. The organic light emitting diode of claim 6, wherein A in Formula 1 is selected from the following moieties:

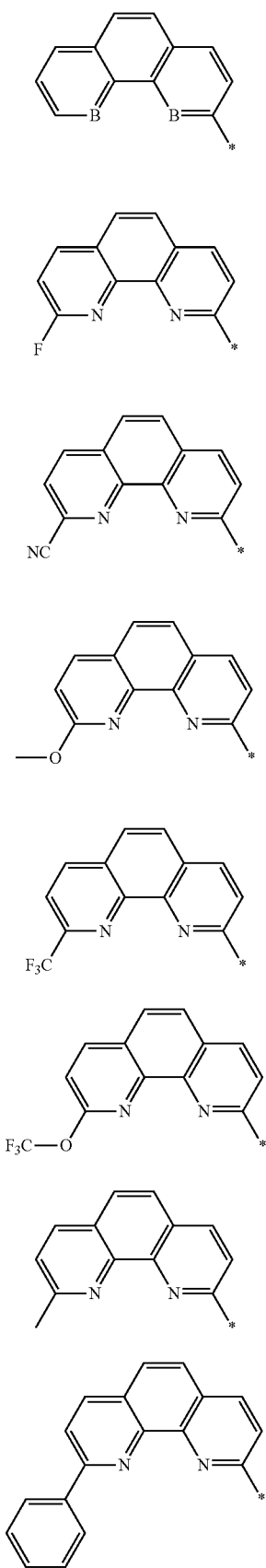
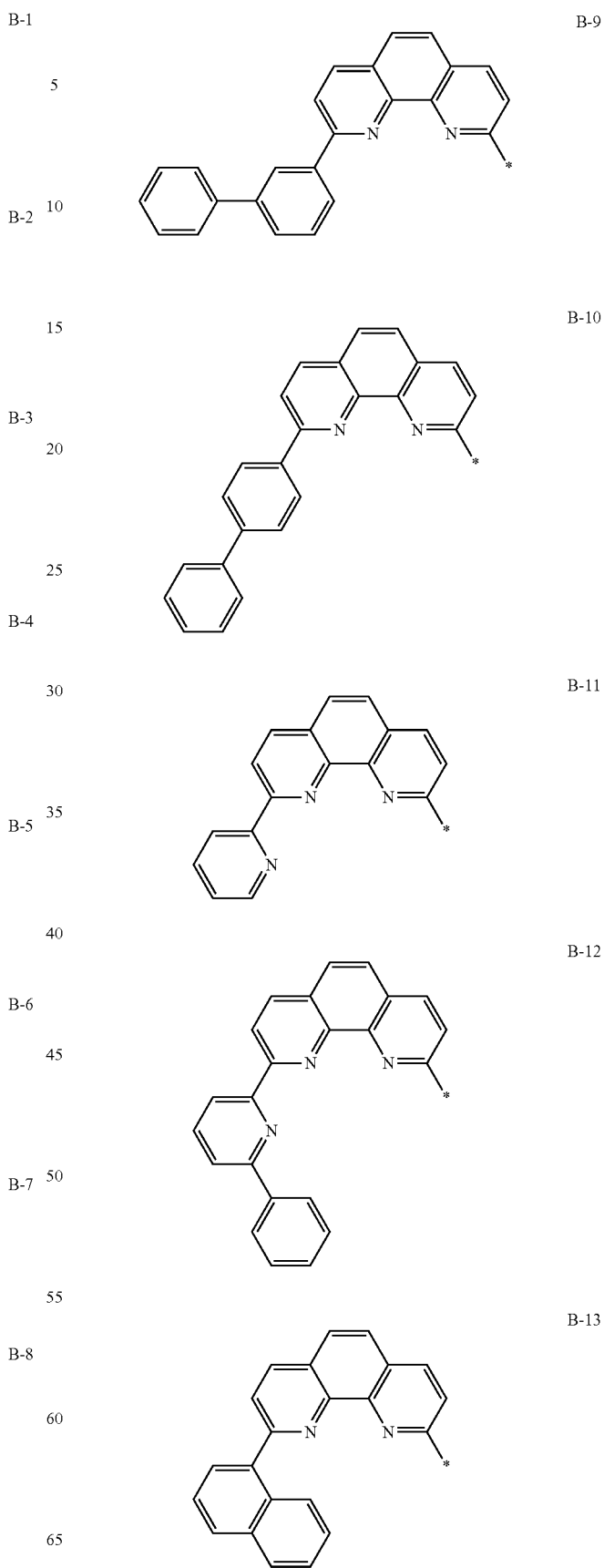

129
-continued
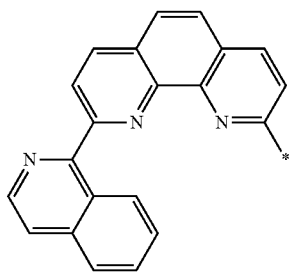
B-14
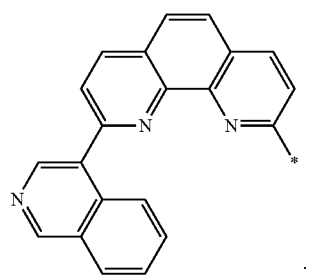
B-15
9. The organic light emitting diode of claim 6, wherein B in Formula 1 is selected from the following moieties:
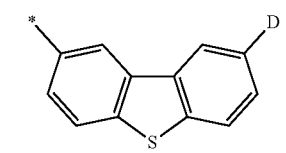
C-1
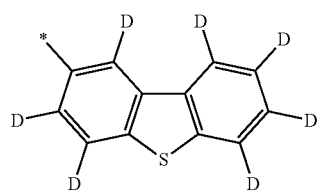
C-2
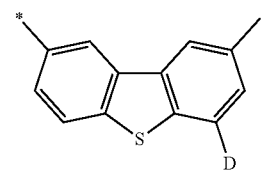
C-3
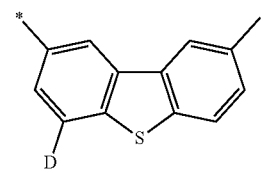
C-4
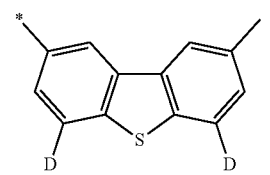
C-5
130
-continued
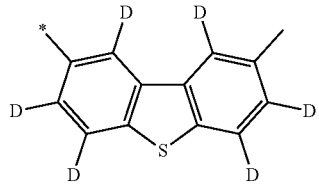
C-6
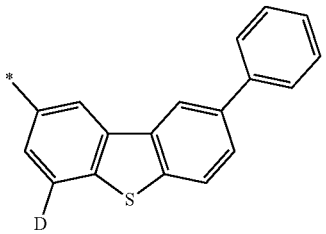
C-7
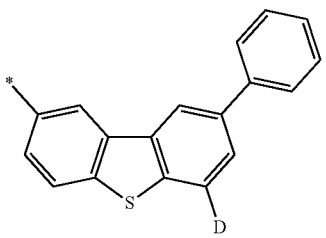
C-8
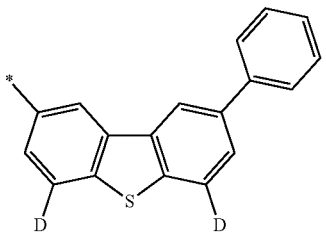
C-9
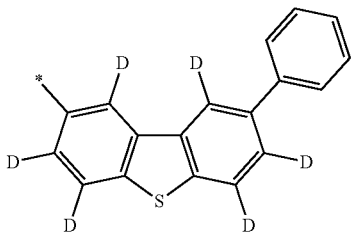
C-10
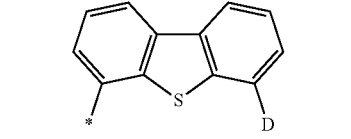
C-11
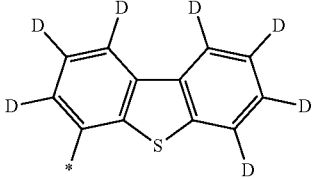
C-12

C-13 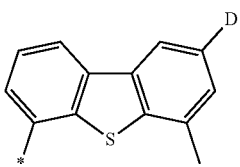
C-14 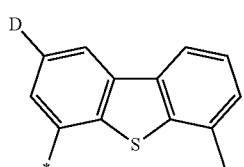
C-15 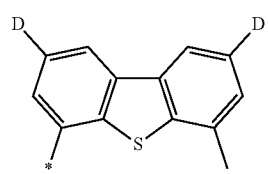
C-16 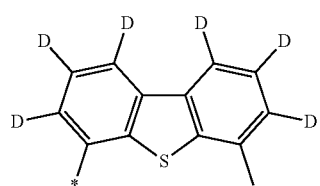
C-17 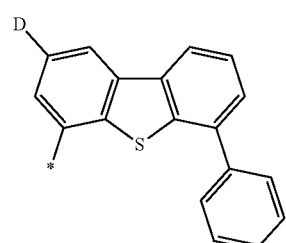
C-18 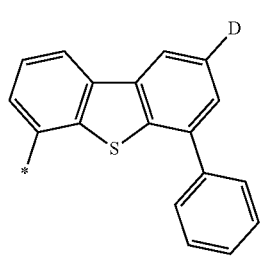
C-19 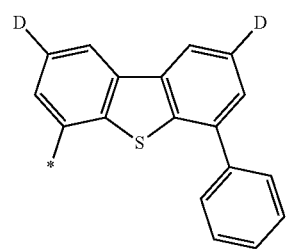
C-20 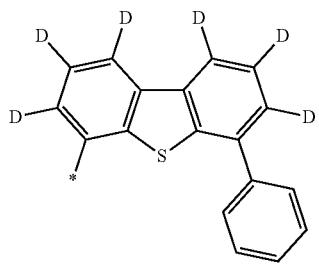
C-21 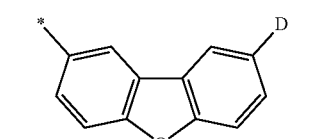
C-22 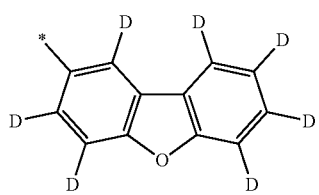
C-23 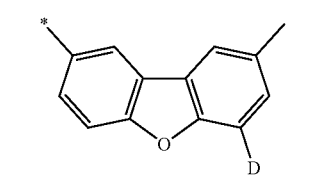
C-24 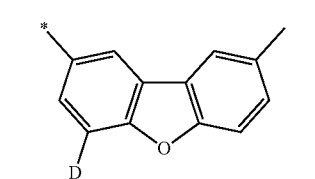
C-25 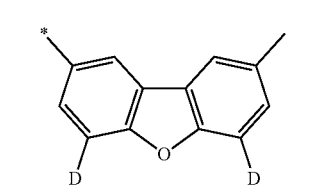
C-26
C-27
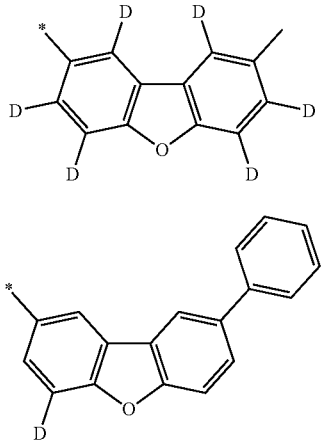

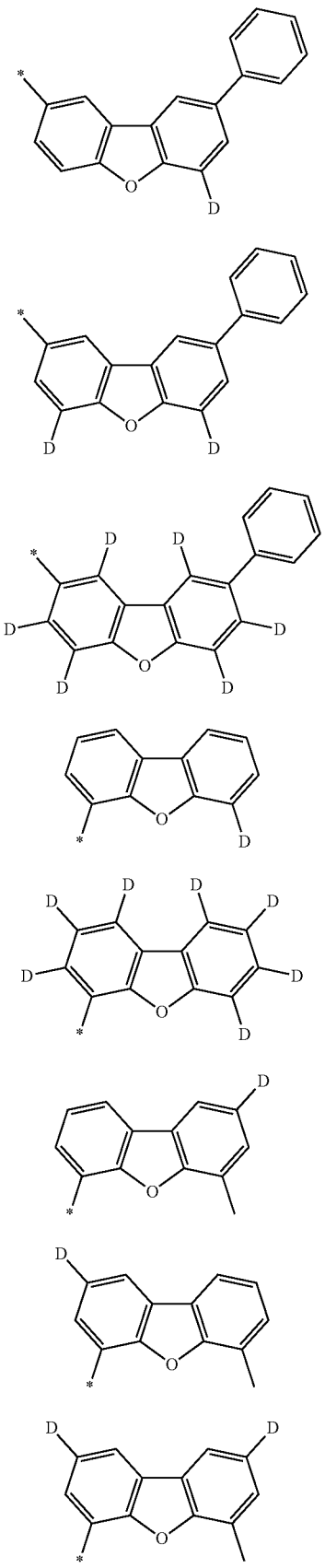
C-28
C-29
C-30
C-31
C-32
C-33
C-34
C-35
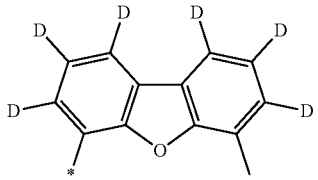
C-36
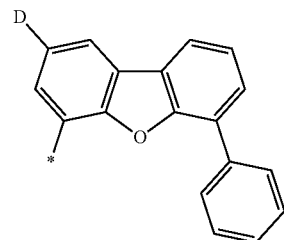
C-37
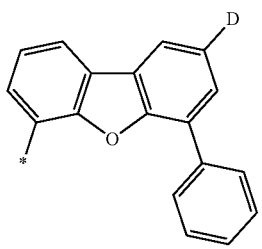
C-38
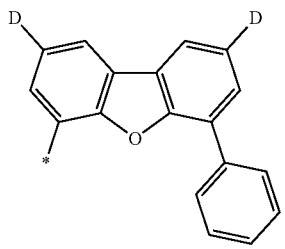
C-39
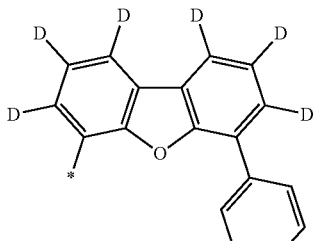
C-40
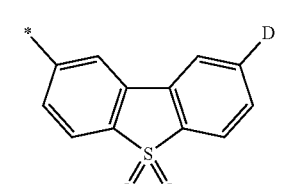
C-41
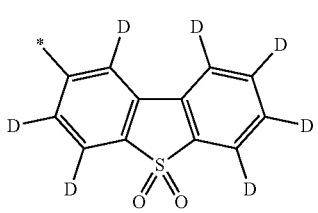
C-42

135
-continued
C-43
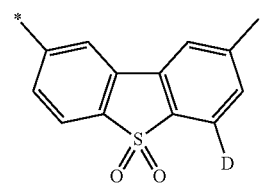
C-44
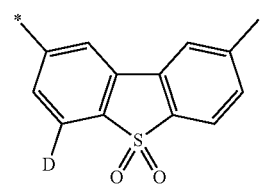
C-45
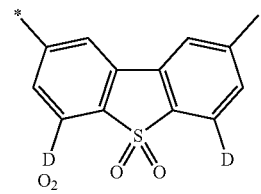
C-46
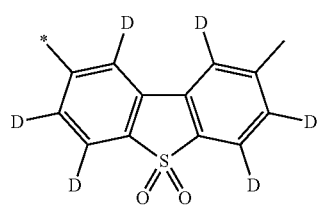
C-47
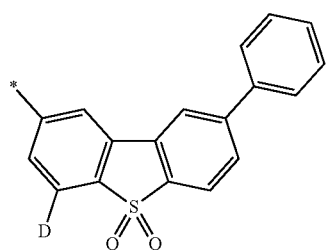
C-48
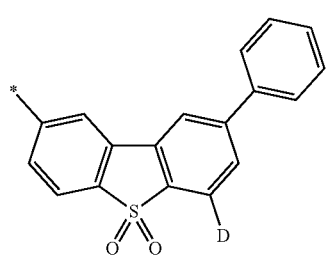
C-49
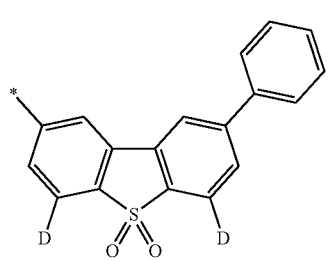
136
-continued
C-50
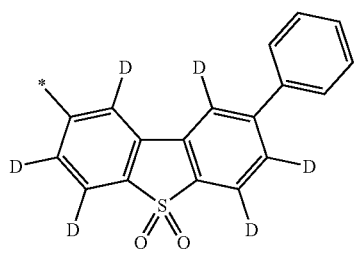
C-51
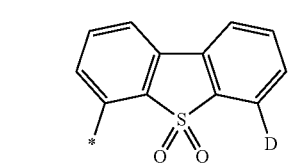
C-52
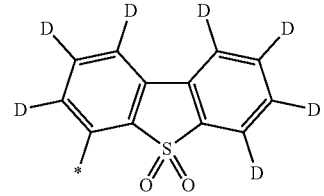
C-53
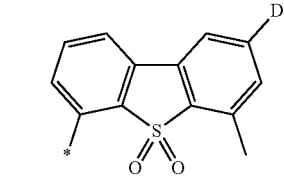
C-54
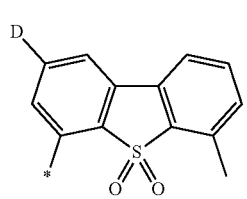
C-55
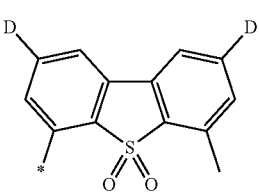
C-56
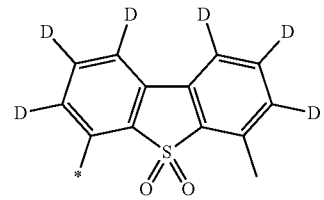

-continued

C-57
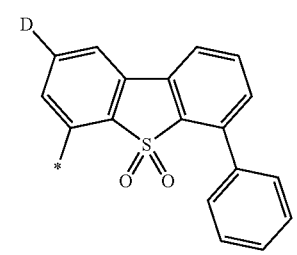

C-58
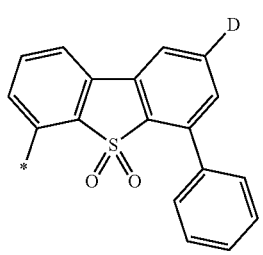

C-59
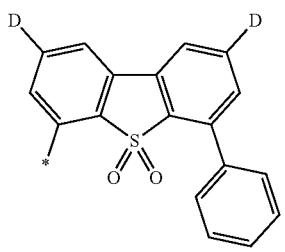

C-60
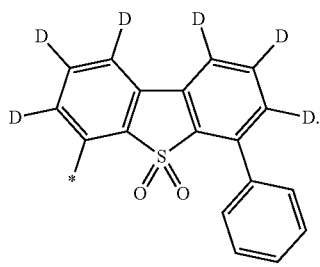

10. The organic light emitting diode of claim 6, the electron transport layer further includes at least one of an alkali metal and an alkaline earth metal.

11. An organic light emitting diode, comprising:
a first electrode;
a second electrode; and
an emissive layer disposed between the first electrode and the second electrode,
wherein the emissive layer includes a first emitting part disposed between the first electrode and the second electrode, a second emitting part disposed between the first emitting part and the second electrode and a charge generation layer disposed between the first emitting part and the second emitting part,
wherein the first emitting part includes a first emitting material layer and a first electron transport layer disposed between the first emitting material layer and the charge generation layer, and
wherein at least one of the first electron transport layer and the charge generation layer includes an organic compound having the following structure of Formula 1:

[Formula 1]

wherein $Ar_1$ is $C_6$-$C_{30}$ arylene or $C_3$-$C_{30}$ hetero arylene; A has the following structure of Formula 2; B has a following structure of Formula 3; and m is 0 or 1;

[Formula 2]

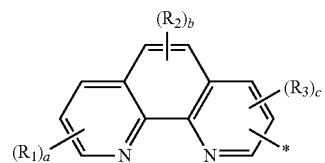

wherein each of $R_1$ to $R_3$ is independently protium, halogen, a cyano group, a $C_1$-$C_{20}$ alkyl group, a $C_1$-$C_{20}$ halo alkyl group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group; each of a, b and c is a number of a substituent, a is an integer of 0 to 3, each of b and c is independently an integer of 0 to 2;

[Formula 3]

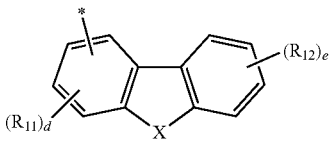

wherein X is O, S or SO; each of $R_{11}$ and $R_{12}$ is independently protium, deuterium, halogen, a cyano group, a $C_1$-$C_{20}$ alkyl group, a $C_1$-$C_{20}$ halo alkyl group, a $C_1$-$C_{20}$ alkyl amino group, a $C_5$-$C_{30}$ alicyclic group, a $C_4$-$C_{30}$ hetero alicyclic group, a $C_6$-$C_{30}$ aromatic group or a $C_3$-$C_{30}$ hetero aromatic group, each of the $C_6$-$C_{30}$ aromatic group and the $C_3$-$C_{30}$ hetero aromatic group is independently unsubstituted or substituted with at least one of a $C_1$-$C_{20}$ alkyl group, a $C_6$-$C_{20}$ aromatic group and a $C_3$-$C_{20}$ hetero aromatic group, at least one of $R_n$ and $R_{12}$ is deuterium; each of d and e is a number of a substituent, d is an integer of 0 to 3 and e is an integer of 0 to 4, at least one of d and e is not 0.

12. The organic light emitting diode of claim 11, wherein $Ar_1$ in Formula 1 is selected from the following moieties:

A-1
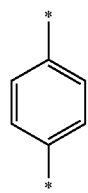

-continued
A-2
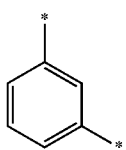
A-3
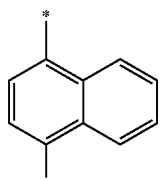
A-4
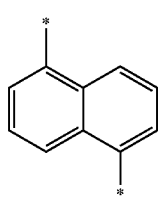
A-5
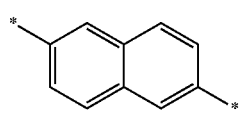
A-6
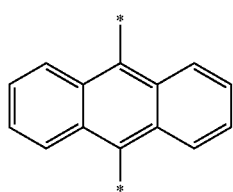
A-7
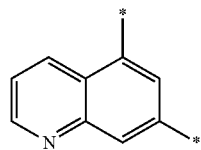
A-8
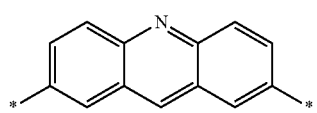
A-9
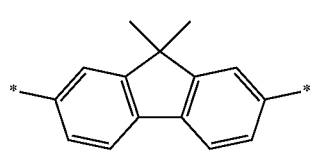
A-10
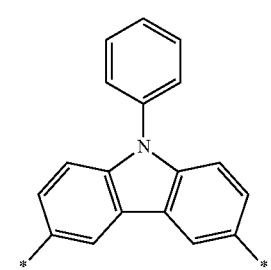
-continued
A-11
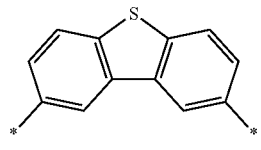
A-12
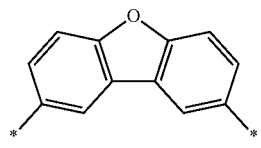
A-13
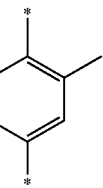
A-14
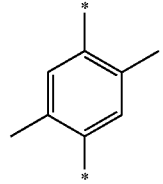
A-15
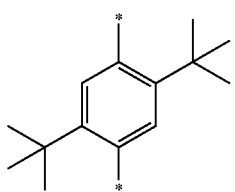
A-16
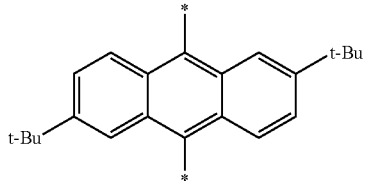
A-17
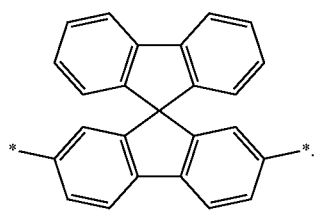
13. The organic light emitting diode of claim 11, wherein A in Formula 1 is selected from the following moieties:
B-1
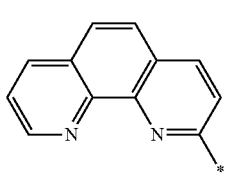

B-2
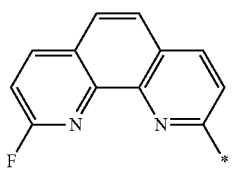
B-3
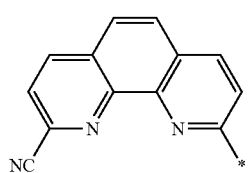
B-4
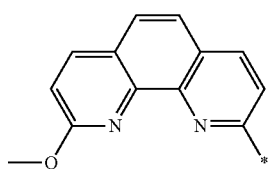
B-5
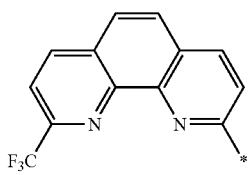
B-6
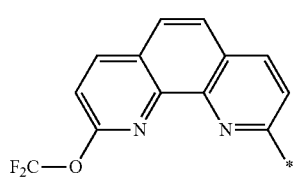
B-7
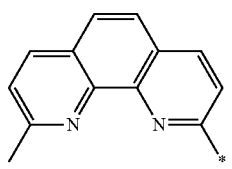
B-8
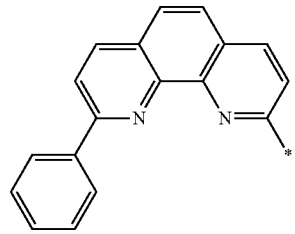
B-9
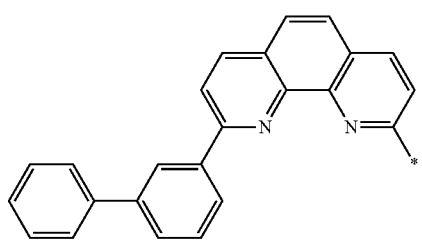
B-10
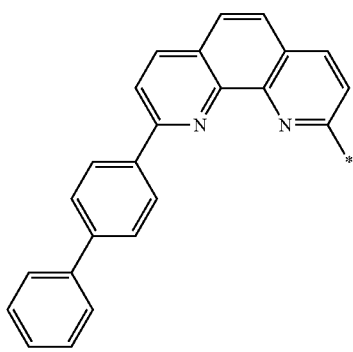
B-11
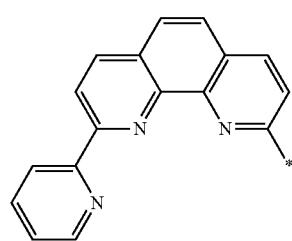
B-12
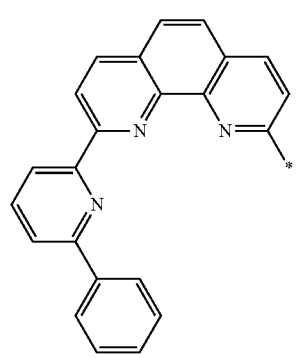
B-13
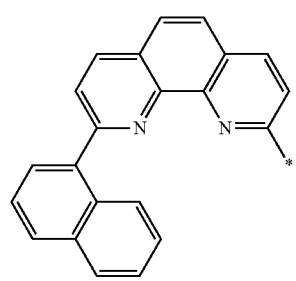
B-14
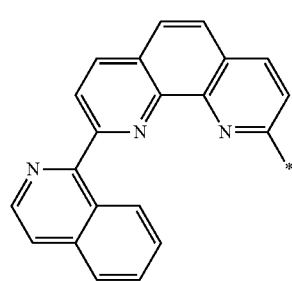

B-15
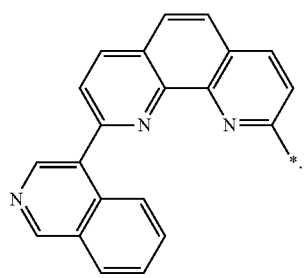
14. The organic light emitting diode of claim 11, wherein B in Formula 1 is selected from the following moieties:
C-1
C-2
C-3
C-4
C-5
C-6
C-7
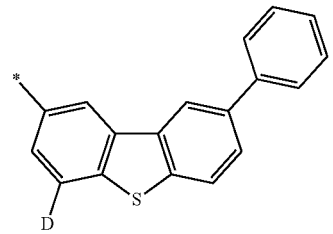
C-8
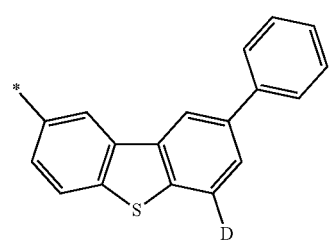
C-9
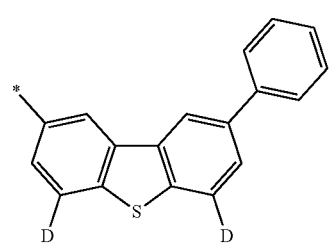
C-10
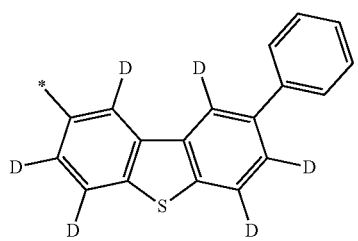
C-11
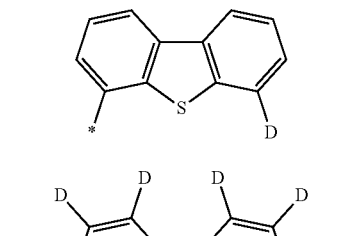
C-12
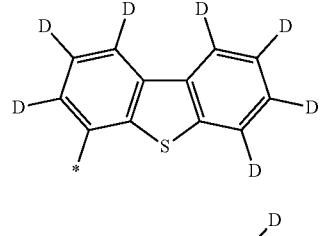
C-13
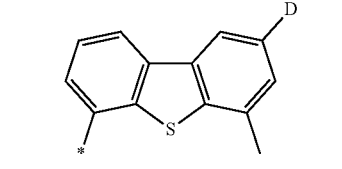

145
-continued
C-14
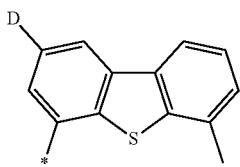
C-15
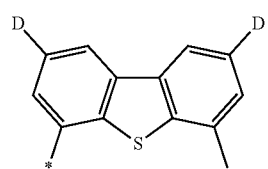
C-16
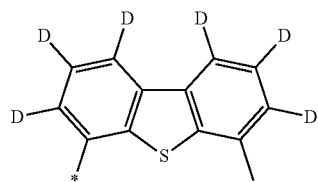
C-17
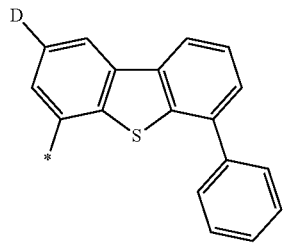
C-18
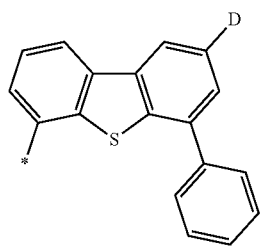
C-19
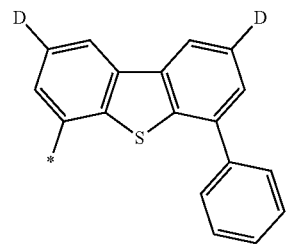
C-20
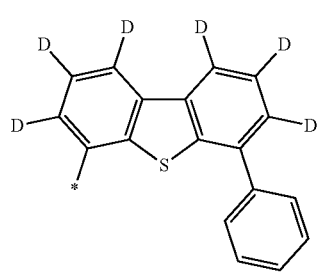
146
-continued
C-21
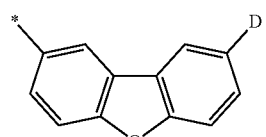
C-22
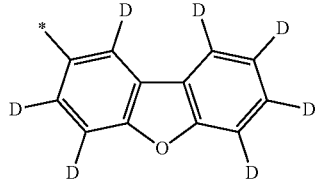
C-23
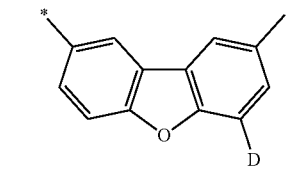
C-24
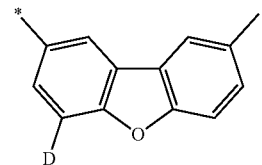
C-25
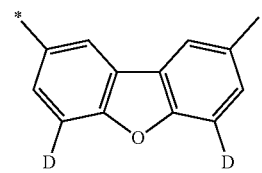
C-26
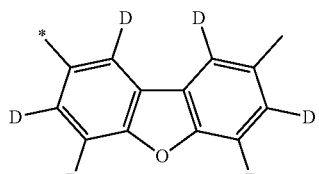
C-27
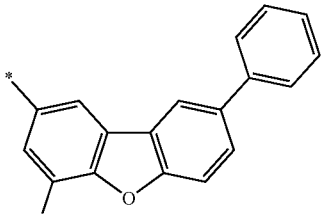
C-28
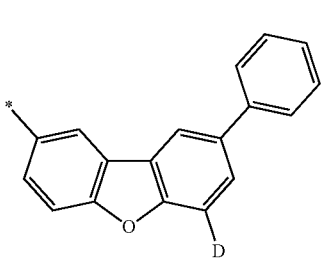

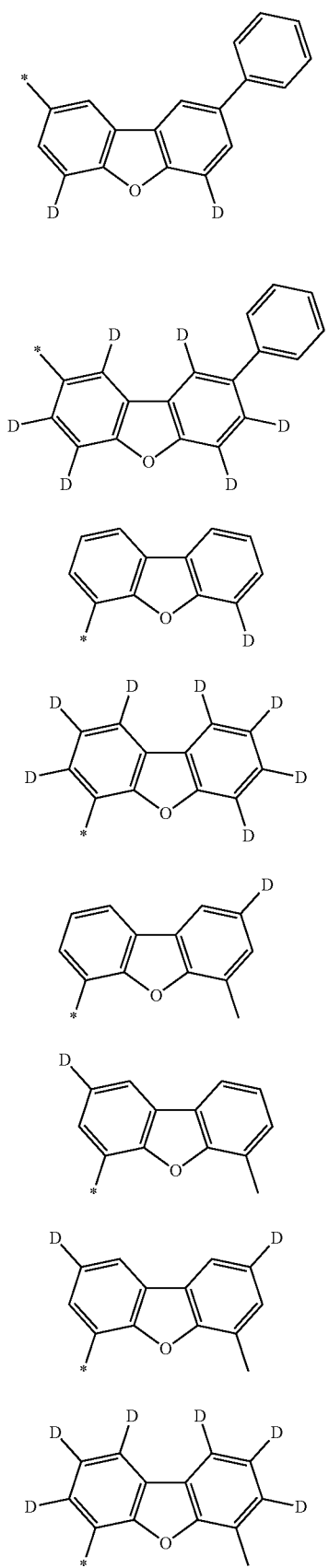
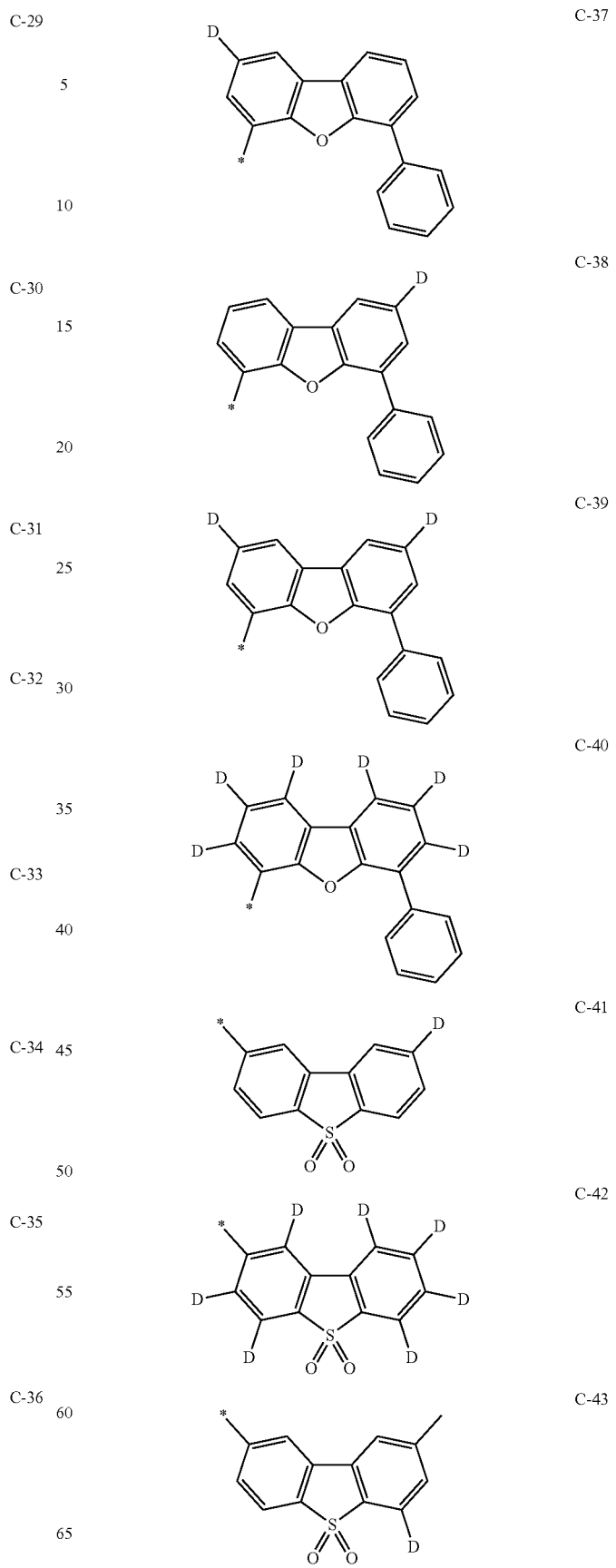

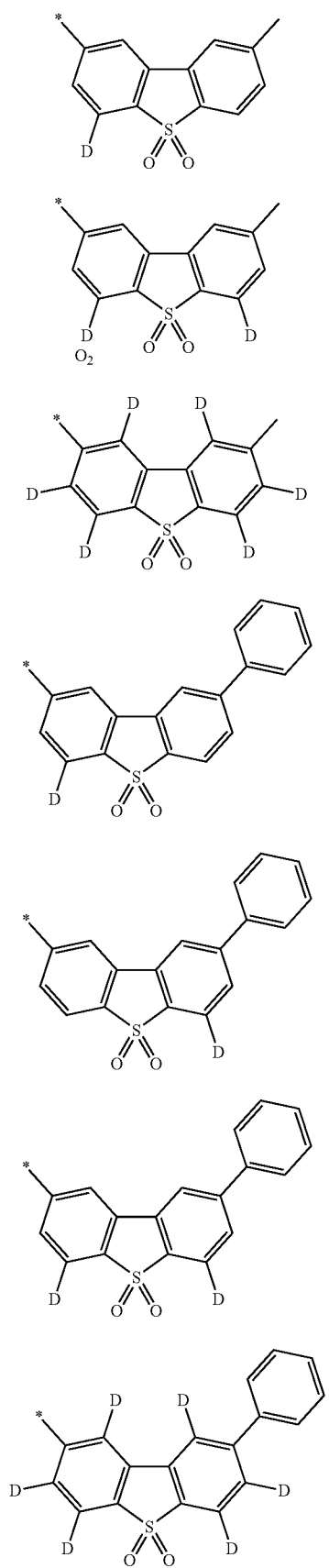
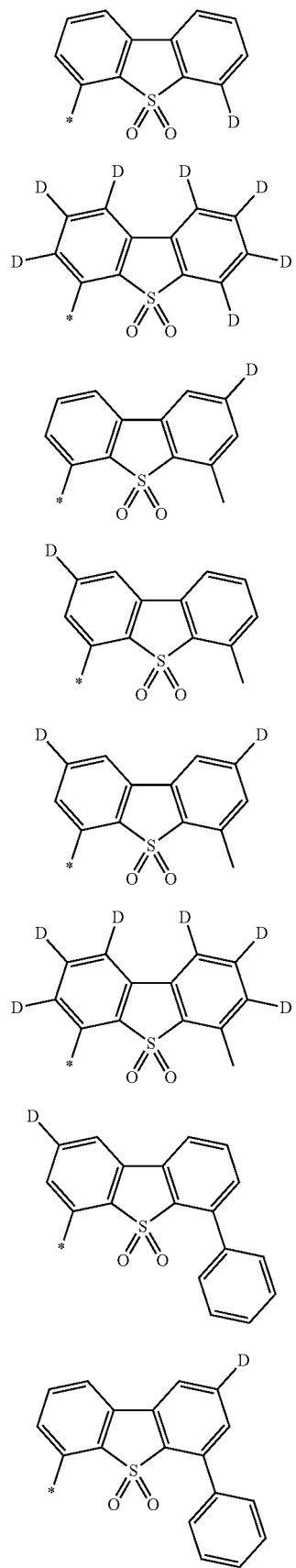

-continued

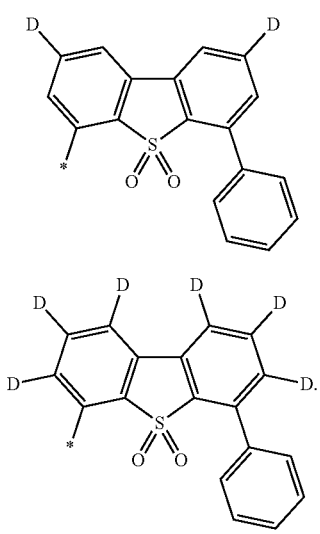

C-59

C-60

15. The organic light emitting diode of claim 11, wherein the charge generation layer includes an N-type charge generation layer disposed between the first emitting part and the second emitting part and a P-type charge generation layer disposed between the N-type charge generation layer and the second emitting part, and
wherein the N-type charge generation layer includes the organic compound.

16. The organic light emitting diode of claim 15 the N-type charge generation layer further includes at least one of an alkali metal and an alkaline earth metal.

17. The organic light emitting diode of claim 11, wherein the second emitting part includes a second emitting material layer and a second electron transport layer disposed between the second emitting material layer and the second electrode, and
wherein the second electron transport layer includes the organic compound.

18. The organic light emitting diode of claim 11, the emissive layer further includes a third emitting part disposed between the second emitting part and a second electrode and a second charge generation layer disposed between the second emitting part and the third emitting part, and
wherein the second charge generation layer includes the organic compound.

19. An organic light emitting device, comprising:
a substrate; and
an organic light emitting diode of claim 6 over the substrate.

20. An organic light emitting device, comprising:
a substrate; and
an organic light emitting diode of claim 11 over the substrate.

21. The organic light emitting device of claim 20, wherein the substrate defines a red pixel region, a green pixel region and a blue pixel region and the organic light emitting diode is located correspondingly to the red pixel region, the green pixel region and the blue pixel region, and the organic light emitting device further includes a color filter layer disposed between the substrate and the organic light emitting diode or over the organic light emitting diode correspondingly to the red pixel region, the green pixel region and the blue pixel region.

22. The organic light emitting device of claim 20, wherein the substrate defines a red pixel region, a green pixel region and a blue pixel region and the organic light emitting diode is located correspondingly to the red pixel region, the green pixel region and the blue pixel region, and the organic light emitting device further includes a color conversion layer disposed between the substrate and the organic light emitting diode or over the organic light emitting diode correspondingly to the red pixel region and the green pixel region.

* * * * *